(12) United States Patent
May et al.

(10) Patent No.: US 12,178,482 B2
(45) Date of Patent: Dec. 31, 2024

(54) ORTHOPAEDIC FIXATION DEVICES, SYSTEMS AND METHODS

(71) Applicant: Biomet Microfixation, LLC, Jacksonville, FL (US)

(72) Inventors: Justin James May, Leesburg, IN (US); Scott Steffensmeier, Winona Lake, IN (US); Jason F. Detweiler, Warsaw, IN (US)

(73) Assignee: Biomet Microfixation, LLC, Jacksonville, FL (US)

( * ) Notice: Subject to any disclaimer, the term of this patent is extended or adjusted under 35 U.S.C. 154(b) by 394 days.

(21) Appl. No.: 17/511,977

(22) Filed: Oct. 27, 2021

(65) Prior Publication Data

US 2022/0047309 A1 Feb. 17, 2022

Related U.S. Application Data

(62) Division of application No. 15/032,980, filed as application No. PCT/US2014/062441 on Oct. 27, 2014, now Pat. No. 11,253,299.

(Continued)

(51) Int. Cl.
*A61B 17/80* (2006.01)
*A61B 17/15* (2006.01)
(Continued)

(52) U.S. Cl.
CPC .......... *A61B 17/8023* (2013.01); *A61B 17/15* (2013.01); *A61B 17/1728* (2013.01); *A61B 17/7059* (2013.01); *A61B 17/8004* (2013.01); *A61B 17/8009* (2013.01); *A61B 17/8033* (2013.01); *A61B 17/8061* (2013.01); (Continued)

(58) Field of Classification Search
CPC ............ A61B 17/8023; A61B 17/7059; A61B 17/8004; A61B 17/8033; A61B 17/8061; A61B 17/8076; A61B 17/15; A61B 17/1728; A61B 17/8009; A61B 17/808
See application file for complete search history.

(56) References Cited

U.S. PATENT DOCUMENTS 3,812,961 A 5/1974 Carlson et al.
4,072,278 A 2/1978 Petersen
(Continued)

FOREIGN PATENT DOCUMENTS

EP 0512262 A1 11/1992
EP 3062747 A1 9/2016
(Continued)

OTHER PUBLICATIONS

"U.S. Appl. No. 14/524,922, Advisory Action mailed Dec. 14, 2018", 3 pgs.
(Continued)

*Primary Examiner* — Sameh R Boles
(74) *Attorney, Agent, or Firm* — SCHWEGMAN LUNDBERG & WOESSNER, P.A.

(57) ABSTRACT

A ratchet fastener includes a base including a fastening portion including threads and a ratchet portion including teeth and a ratchet wheel disposed in mating arrangement with the teeth. The ratchet fastener is configured to receive a tether. The ratchet wheel is configured to be rotated to tighten the tether.

16 Claims, 53 Drawing Sheets

Related U.S. Application Data

(60) Provisional application No. 62/039,672, filed on Aug. 20, 2014, provisional application No. 61/896,376, filed on Oct. 28, 2013.

(51) Int. Cl.
*A61B 17/17* (2006.01)
*A61B 17/70* (2006.01)
*A61B 17/56* (2006.01)
*A61B 17/68* (2006.01)

(52) U.S. Cl.
CPC ........ *A61B 17/8076* (2013.01); *A61B 17/808* (2013.01); *A61B 2017/564* (2013.01); *A61B 2017/681* (2013.01); *A61B 17/8057* (2013.01)

(56) References Cited

U.S. PATENT DOCUMENTS

| | | |
|---|---|---|
| 5,484,439 A | 1/1996 | Olson et al. |
| 5,507,801 A | 4/1996 | Gisin et al. |
| 5,827,286 A | 10/1998 | Incavo et al. |
| 5,849,012 A | 12/1998 | Abboudi |
| 5,894,843 A | 4/1999 | Benetti et al. |
| 5,925,049 A | 7/1999 | Gustilo et al. |
| 6,007,538 A | 12/1999 | Levin |
| 6,051,007 A | 4/2000 | Hogendijk et al. |
| 6,224,602 B1 | 5/2001 | Hayes |
| 6,355,036 B1 | 3/2002 | Nakajima |
| 6,471,706 B1 | 10/2002 | Schumacher et al. |
| 6,666,867 B2 | 12/2003 | Ralph et al. |
| 6,821,279 B2 | 11/2004 | Di Emidio |
| 6,872,210 B2 | 3/2005 | Hearn |
| 7,011,665 B2 | 3/2006 | Null et al. |
| 7,033,377 B2 | 4/2006 | Miller, III |
| 7,044,952 B2 | 5/2006 | Michelson |
| 7,048,739 B2 | 5/2006 | Konieczynski |
| 7,156,847 B2 | 1/2007 | Abramson |
| 7,166,109 B2 | 1/2007 | Biedermann et al. |
| 7,214,226 B2 | 5/2007 | Alleyne |
| 7,291,152 B2 | 11/2007 | Abdou |
| 7,479,143 B2 | 1/2009 | Suh |
| 7,540,874 B2 | 6/2009 | Trumble et al. |
| 7,604,638 B2 | 10/2009 | Jacene et al. |
| 7,621,914 B2 | 11/2009 | Ralph et al. |
| 7,635,364 B2 | 12/2009 | Barrall et al. |
| 7,641,675 B2 | 1/2010 | Lindemann et al. |
| 7,670,361 B2 | 3/2010 | Nesper et al. |
| 7,695,473 B2 | 4/2010 | Ralph et al. |
| 7,749,256 B2 | 7/2010 | Farris et al. |
| 7,776,047 B2 | 8/2010 | Fanger |
| 7,780,672 B2 | 8/2010 | Metzger et al. |
| 7,993,375 B2 | 8/2011 | Bae et al. |
| 8,029,543 B2 | 10/2011 | Young et al. |
| 8,128,628 B2 | 3/2012 | Freid et al. |
| 8,133,227 B2 | 3/2012 | Morales et al. |
| 8,206,390 B2 | 6/2012 | Lindemann |
| 8,257,355 B2 | 9/2012 | Chin et al. |
| 8,282,644 B2 | 10/2012 | Edwards |
| 8,348,949 B2 | 1/2013 | Butler et al. |
| 8,366,754 B2 | 2/2013 | Teague et al. |
| 8,388,663 B2 | 3/2013 | Bush, Jr. et al. |
| 8,435,265 B2 | 5/2013 | Konieczynski et al. |
| 8,486,079 B2 | 7/2013 | Heavener et al. |
| 8,518,089 B2 | 8/2013 | Gabele |
| 8,523,861 B2 | 9/2013 | Kiritsis |
| 8,585,742 B2 | 11/2013 | Windolf |
| 8,636,738 B2 | 1/2014 | Mcclintock et al. |
| 8,652,142 B2 | 2/2014 | Geissler |
| 10,226,290 B2 | 3/2019 | Steffensmeier et al. |
| 10,441,329 B2 | 10/2019 | May et al. |
| 11,234,744 B2 | 2/2022 | Steffensmeier et al. |
| 11,253,299 B2 | 2/2022 | May et al. |
| 11,344,345 B2 | 5/2022 | May et al. |
| 11,759,242 B2 | 9/2023 | May et al. |
| 2004/0015174 A1 | 1/2004 | Null |
| 2004/0097938 A1 | 5/2004 | Alleyne |
| 2004/0204710 A1 | 10/2004 | Patel et al. |
| 2005/0043732 A1 | 2/2005 | Dalton |
| 2005/0124990 A1 | 6/2005 | Teague et al. |
| 2005/0177163 A1 | 8/2005 | Abdou |
| 2006/0122606 A1 | 6/2006 | Wolgen |
| 2006/0235398 A1 | 10/2006 | Farris et al. |
| 2007/0288010 A1 | 12/2007 | Alleyne |
| 2009/0131987 A1 | 5/2009 | Matityahu |
| 2010/0057127 A1 | 3/2010 | Mcguire et al. |
| 2010/0076444 A1 | 3/2010 | Staehler et al. |
| 2010/0121328 A1 | 5/2010 | Reitzig et al. |
| 2010/0198221 A1 | 8/2010 | Hearn |
| 2010/0268242 A1 | 10/2010 | Ciccone et al. |
| 2010/0324566 A1 | 12/2010 | Rathbun |
| 2011/0004254 A1 | 1/2011 | Beger et al. |
| 2011/0034958 A1 | 2/2011 | Anderson et al. |
| 2011/0082459 A1 | 4/2011 | Aravot |
| 2011/0230885 A1 | 9/2011 | Weiner et al. |
| 2011/0238068 A1 | 9/2011 | Bernsteiner |
| 2012/0059418 A1* | 3/2012 | Denham ............ A61B 17/8869 606/232 |
| 2012/0109135 A1 | 5/2012 | Bailey |
| 2012/0136392 A1 | 5/2012 | Keegan et al. |
| 2012/0265203 A1 | 10/2012 | Angelucci et al. |
| 2012/0316562 A1 | 12/2012 | Costa |
| 2013/0090695 A1 | 4/2013 | Bernstein et al. |
| 2013/0204310 A1 | 8/2013 | Roman et al. |
| 2013/0253592 A1 | 9/2013 | Larche et al. |
| 2013/0282064 A1 | 10/2013 | Arnin |
| 2013/0304067 A1 | 11/2013 | Hess et al. |
| 2014/0039561 A1 | 2/2014 | Weiner et al. |
| 2014/0142638 A1 | 5/2014 | Goodwin et al. |
| 2014/0243837 A1* | 8/2014 | Mebarak ............ A61B 17/842 606/96 |
| 2015/0018830 A1 | 1/2015 | Knoepfle et al. |
| 2015/0045794 A1 | 2/2015 | Garcia et al. |
| 2015/0119887 A1 | 4/2015 | May et al. |
| 2016/0051297 A1 | 2/2016 | Steffensmeier et al. |
| 2016/0262812 A1 | 9/2016 | May et al. |
| 2018/0177510 A1 | 6/2018 | Whitaker et al. |
| 2019/0167320 A1 | 6/2019 | Steffensmeier et al. |
| 2020/0015869 A1 | 1/2020 | May et al. |
| 2022/0125492 A1 | 4/2022 | Steffensmeier et al. |
| 2022/0257293 A1 | 8/2022 | May et al. |

FOREIGN PATENT DOCUMENTS

| | | |
|---|---|---|
| EP | 3182905 A1 | 6/2017 |
| WO | WO-2015065915 A1 | 5/2015 |
| WO | WO-2015065915 A4 | 6/2015 |
| WO | WO-2016029008 A1 | 2/2016 |

OTHER PUBLICATIONS

"U.S. Appl. No. 14/524,922, Final Office Action mailed Oct. 3, 2018", 15 pgs.

"U.S. Appl. No. 14/524,922, Non Final Office Action mailed Feb. 8, 2019", 12 pgs.

"U.S. Appl. No. 14/524,922, Non Final Office Action mailed Mar. 9, 2018", 18 pgs.

"U.S. Appl. No. 14/524,922, Notice of Allowance mailed Jun. 3, 2019", 9 pgs.

"U.S. Appl. No. 14/524,922, Response filed May 8, 2019 to Non Final Office Action mailed Feb. 8, 2019", 14 pgs.

"U.S. Appl. No. 14/524,922, Response filed Jun. 8, 2018 to Non Final Office Action mailed Mar. 9, 2018", 19 pgs.

"U.S. Appl. No. 14/524,922, Response filed Sep. 12, 2017 to Restriction Requirement mailed Jul. 18, 2017", 2 pgs.

"U.S. Appl. No. 14/524,922, Response filed Nov. 30, 2018 to Final Office Action mailed Oct. 3, 2018", 16 pgs.

"U.S. Appl. No. 14/524,922, Restriction Requirement mailed Jul. 18, 2017", 6 pgs.

"U.S. Appl. No. 14/831,422, Advisory Action mailed Jul. 6, 2018", 3 pgs.

(56) References Cited

OTHER PUBLICATIONS

"U.S. Appl. No. 14/831,422, Final Office Action mailed Mar. 29, 2018", 14 pgs.
"U.S. Appl. No. 14/831,422, Non Final Office Action mailed Oct. 10, 2017", 12 pgs.
"U.S. Appl. No. 14/831,422, Notice of Allowance mailed Oct. 31, 2018", 6 pgs.
"U.S. Appl. No. 14/831,422, Response filed Jan. 8, 2018 to Non Final Office Action mailed Oct. 10, 2017", 9 pgs.
"U.S. Appl. No. 14/831,422, Response filed Jun. 27, 2018 to Final Office Action mailed Mar. 29, 2018", 8 pgs.
"U.S. Appl. No. 15/032,980, Final Office Action mailed Apr. 19, 2018", 7 pgs.
"U.S. Appl. No. 15/032,980, Final Office Action mailed Jun. 26, 2019", 6 pgs.
"U.S. Appl. No. 15/032,980, Final Office Action mailed Sep. 18, 2018", 8 pgs.
"U.S. Appl. No. 15/032,980, Non Final Office Action mailed Sep. 5, 2017", 7 pgs.
"U.S. Appl. No. 15/032,980, Non Final Office Action mailed Dec. 28, 2018", 7 pgs.
"U.S. Appl. No. 15/032,980, Notice of Allowance mailed Sep. 20, 2019", 5 pgs.
"U.S. Appl. No. 15/032,980, Notice of Allowance mailed Oct. 27, 2021", 5 pgs.
"U.S. Appl. No. 15/032,980, Preliminary Amendment filed Apr. 28, 2016", 5 pgs.
"U.S. Appl. No. 15/032,980, Response filed Mar. 27, 2019 to Non Final Office Action mailed Dec. 28, 2018", 7 pgs.
"U.S. Appl. No. 15/032,980, Response filed May 15, 2017 to Restriction Requirement mailed Apr. 4, 2017", 2 pgs.
"U.S. Appl. No. 15/032,980, Response filed Jul. 18, 2018 to Final Office Action mailed Apr. 19, 2018", 6 pgs.
"U.S. Appl. No. 15/032,980, Response filed Aug. 21, 2017 to Restriction Requirement mailed Jun. 23, 2017", 3 pgs.
"U.S. Appl. No. 15/032,980, Response filed Aug. 26, 2019 to Final Office Action mailed Jun. 26, 2019", 6 pgs.
"U.S. Appl. No. 15/032,980, Response filed Dec. 4, 2017 to Non Final Office Action mailed Sep. 5, 2017", 6 pgs.
"U.S. Appl. No. 15/032,980, Response filed Dec. 17, 2018 to Final Office Action mailed Sep. 18, 2018", 8 pgs.
"U.S. Appl. No. 15/032,980, Restriction Requirement mailed Apr. 4, 2017", 8 pgs.
"U.S. Appl. No. 15/032,980, Restriction Requirement mailed Jun. 23, 2017", 8 pgs.
"U.S. Appl. No. 16/263,100, Final Office Action mailed Mar. 8, 2021", 12 pgs.
"U.S. Appl. No. 16/263,100, Non Final Office Action mailed Jun. 14, 2021", 11 pgs.
"U.S. Appl. No. 16/263,100, Non Final Office Action mailed Nov. 2, 2020", 10 pgs.
"U.S. Appl. No. 16/263,100, Notice of Allowance mailed Sep. 27, 2021", 6 pgs.
"U.S. Appl. No. 16/263,100, Response filed Feb. 2, 2021 to Non Final Office Action mailed Nov. 2, 2020", 9 pgs.
"U.S. Appl. No. 16/263,100, Response filed May 18, 2021 to Final Office Action mailed Mar. 8, 2021", 13 pgs.
"U.S. Appl. No. 16/263,100, Response filed Sep. 14, 2021 to Non Final Office Action mailed Jun. 14, 2021", 12 pgs.
"U.S. Appl. No. 16/580,331, Non Final Office Action mailed Sep. 15, 2021", 7 pgs.
"U.S. Appl. No. 16/580,331, Notice of Allowance mailed Jan. 28, 2022", 7 pgs.
"U.S. Appl. No. 16/580,331, Response filed Dec. 14, 2021 to Non Final Office Action mailed Sep. 15, 2021", 7 pgs.
"U.S. Appl. No. 17/733,791, Preliminary Amendment filed Jun. 2, 2022", 5 pgs.
"European Application Serial No. 14859238.9, Communication Pursuant to Article 94(3) EPC mailed Aug. 16, 2019", 5 pgs.
"European Application Serial No. 14859238.9, Extended European Search Report mailed Apr. 12, 2017", 9 pgs.
"European Application Serial No. 14859238.9, Intention to Grant mailed Dec. 20, 2021", 103 pgs.
"European Application Serial No. 14859238.9, Response filed Nov. 9, 2017 to Extended European Search Report mailed Apr. 12, 2017", 49 pgs.
"European Application Serial No. 14859238.9, Response filed Dec. 17, 2019 to Communication Pursuant to Article 94(3) EPC mailed Aug. 16, 2019", 51 pgs.
"European Application Serial No. 14859238.9, Response to Communication pursuant to Rules 161(1) and 162 EPC filed Dec. 16, 2016", 5 pgs.
"European Application Serial No. 15834517.3, Extended European Search Report mailed Apr. 13, 2018", 9 pgs.
"European Application Serial No. 15834517.3, Noting of loss of rights mailed Dec. 20, 2018", 2 pgs.
"European Application Serial No. 15834517.3, Response to Communication pursuant to Rules 161(1) and 162 EPC filed Oct. 24, 2017", 8 pgs.
"International Application Serial No. PCT/US2014/062441, International Preliminary Report on Patentability mailed May 12, 2016", 8 pgs.
"International Application Serial No. PCT/US2014/062441, International Search Report mailed Mar. 25, 2015", 4 pgs.
"International Application Serial No. PCT/US2014/062441, Invitation to Pay Additional Fees mailed Jan. 14, 2015", 8 pgs.
"International Application Serial No. PCT/US2014/062441, Written Opinion mailed Mar. 25, 2015", 6 pgs.
"International Application Serial No. PCT/US2015/046098, International Preliminary Report on Patentability mailed Mar. 2, 2017", 7 pgs.
"International Application Serial No. PCT/US2015/046098, International Search Report mailed Nov. 23, 2015", 2 pgs.
"International Application Serial No. PCT/US2015/046098, Written Opinion mailed Nov. 23, 2015", 5 pgs.
U.S. Appl. No. 14/524,922 U.S. Pat. No. 10,441,329, filed Oct. 27, 2014, Orthopaedic Fixation Device, System and Method.
U.S. Appl. No. 16/580,331 U.S. Pat. No. 11,344,345, filed Sep. 24, 2019, Orthopaedic Fixation Device, System and Method.
U.S. Appl. No. 17/733,791, filed Apr. 29, 2022, Orthopaedic Fixation Device, System and Method.
U.S. Appl. No. 14/831,422 U.S. Pat. No. 10,226,290, filed Aug. 20, 2015, Implant Positioning Devices and Methods.
U.S. Appl. No. 16/263,100 U.S. Pat. No. 11,234,744, filed Jan. 31, 2019, Implant Positioning Devices and Methods.
U.S. Appl. No. 17/569,259, filed Jan. 5, 2022, Implant Positioning Devices and Methods.
U.S. Appl. No. 15/032,980 U.S. Pat. No. 11,253,299, filed Apr. 28, 2016, Orthopaedic Fixation Device, Systems and Methods.
"U.S. Appl. No. 17/569,259, Final Office Action mailed Sep. 8, 2023", 13 pgs.
"U.S. Appl. No. 17/569,259, Non Final Office Action mailed Apr. 10, 2023", 12 pgs.
"U.S. Appl. No. 17/569,259, Response filed May 25, 2023 to Non Final Office Action mailed Apr. 10, 2023", 10 pgs.
"U.S. Appl. No. 17/569,259, Response filed Nov. 6, 2023 to Final Office Action mailed Sep. 8, 2023", 10 pgs.
"U.S. Appl. No. 17/733,791, Notice of Allowance mailed May 12, 2023", 9 pgs.

\* cited by examiner

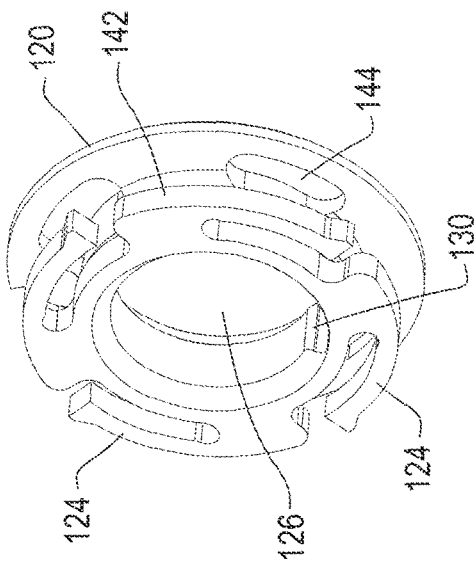
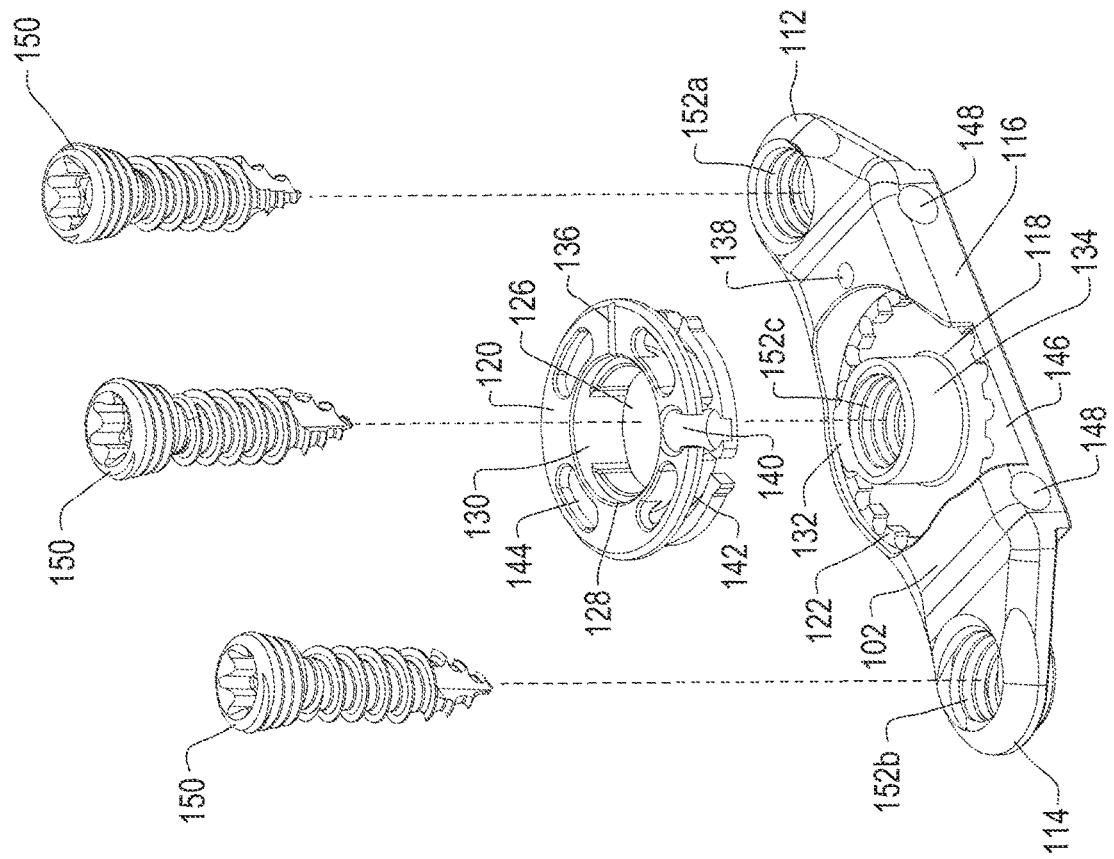

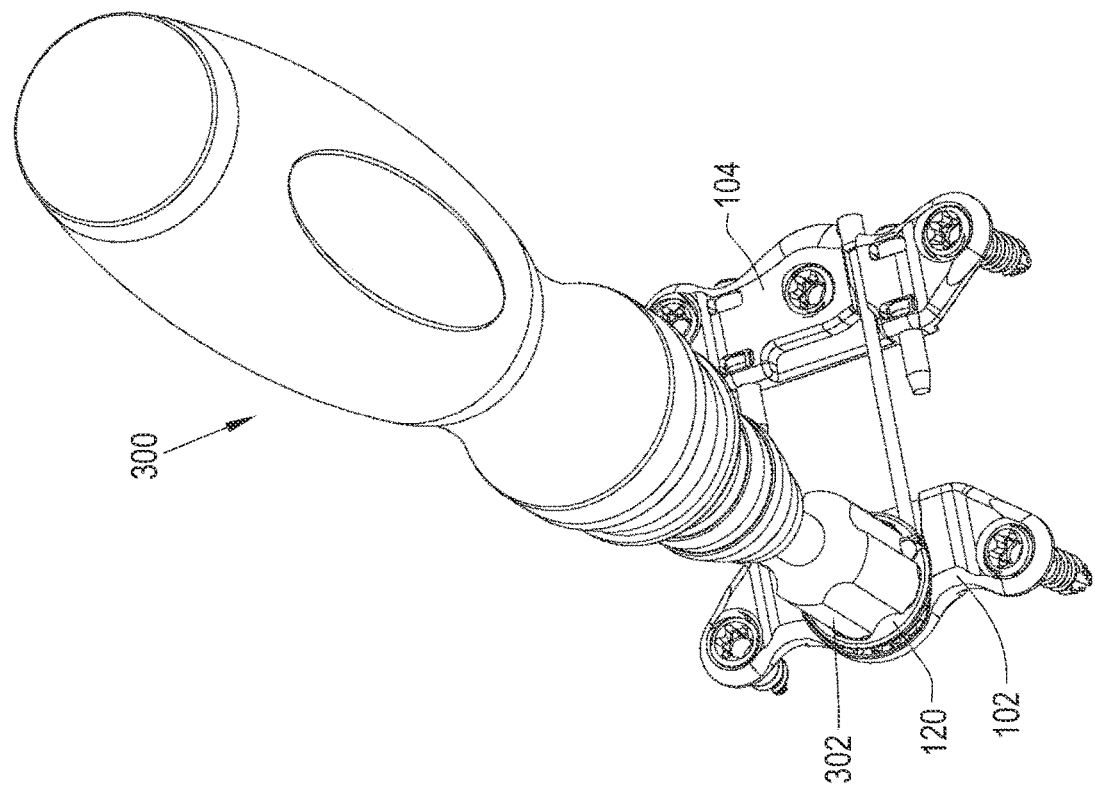

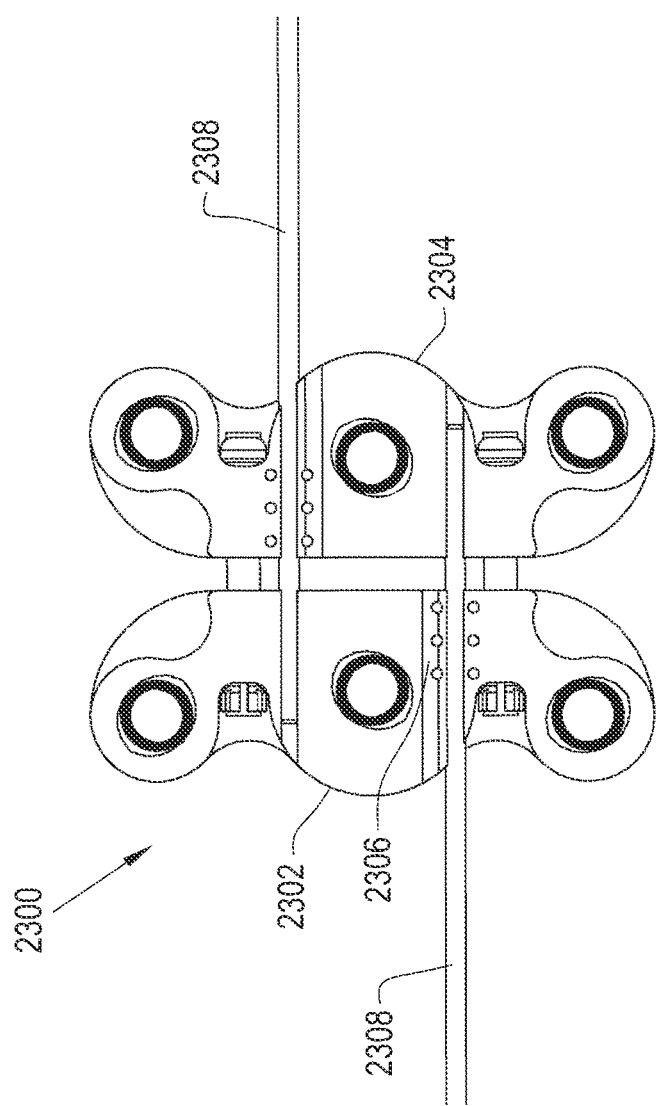

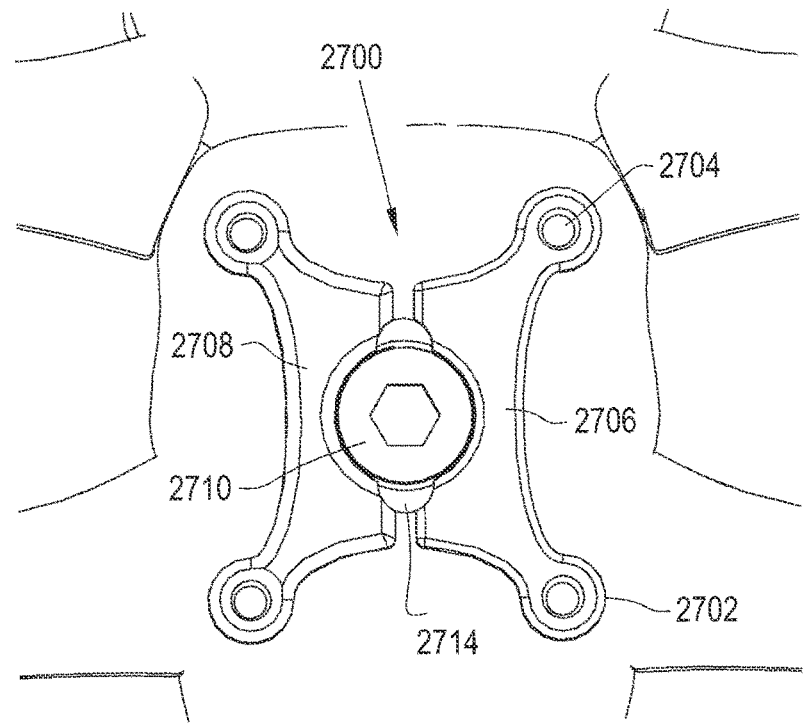
FIG. 54
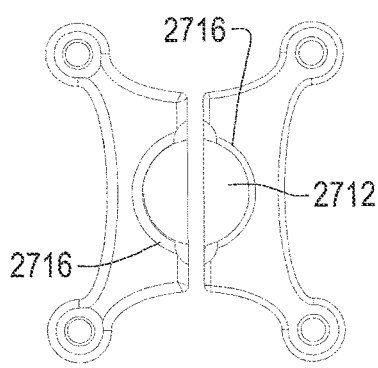 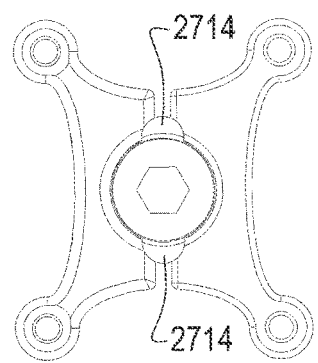 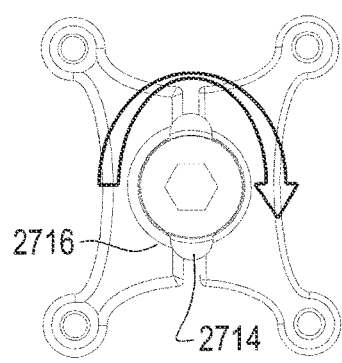
FIG. 55  FIG. 56  FIG. 57

ORTHOPAEDIC FIXATION DEVICES, SYSTEMS AND METHODS

CROSS REFERENCES TO RELATED APPLICATIONS

This is a division of U.S. patent application Ser. No. 15/032,980, entitled "ORTHOPAEDIC FIXATION DEVICES, SYSTEMS AND METHODS", filed Apr. 28, 2016, which is incorporated herein by reference. U.S. patent application Ser. No. 15/032,980 is a national stage entry of PCT/US2014/062441 filed on Oct. 27, 2014, which claims the benefit of U.S. Provisional Patent Application Ser. No. 61/896,376, filed Oct. 28, 2013, and U.S. Provisional Patent Application Ser. No. 62/039,672, filed Aug. 20, 2014, the contents of which are incorporated herein by reference in their entirety.

FIELD

The invention relates generally to orthopaedic fixation devices, systems and methods of such fixation, and particularly regarding use in bone fixation where adjacent sections of a bone, such as a resected bone, are intended to be rejoined.

BACKGROUND

In some surgical procedures involving bones, for instance, the procedure may involve separating a bone into portions, which are thereafter reunited. This happens, for instance, in entries into the chest cavity, as for heart surgery, where the sternum is required to be separated along its length (resected), in the transverse plane, or a combination of the two. There may be other instances where a bone has undergone fracturing through some trauma, and is thereafter to have portions rejoined for proper healing. While discussed herein largely in the context of bones, it will nonetheless be understood that aspects of the invention hereafter described may be applicable to other body parts.

The bones or skeletal tissue, or combinations of bone and tissue, can be held secure to one another in adjacency using a fixation device, or system. The system is desirably designed that in the event that subsequent surgery is required, as in an emergency reentry to the chest cavity, the fixation device may be opened quickly and easily with as little harm to the patient as possible. Many kinds of conventional fixation devices of the foregoing type include wires or cables that are organized to pull the bone portions together, laterally across a divide or fracture. These types of fixation devices can be relatively complex to emplace, and require more effort than desired to undue in the event of an emergency. They are also typically emplaced post-resection.

SUMMARY

A device for guiding separation of and rejoining opposed portions of a bone where the portions have been separated, as in a surgical procedure, is disclosed. In an embodiment, the device includes a first plate configured to be disposed on and coupled to the bone and a second plate configured to be disposed on and coupled to the bone and spaced a distance from the first plate. The space allows a cutting tool to be used to create a divide in the bone between the first and second plates. That is, in this form of the invention, the fixation device is emplaced before the bone is separated.

The first plate includes a first face, a ratchet mechanism on a top portion of the first plate facing away from the bone, and a first fastener aperture configured to receive a first fastener to couple the first plate to the bone. The second plate includes a second face configured to oppose and face the first face when the first and second plates are coupled to the bone, and a second fastener aperture configured to receive a second fastener to couple the second plate to the bone.

The device further includes a locking element that is engageable with the ratchet mechanism and the second plate. The locking element is configured to be coiled in response to operation of the ratchet mechanism to draw the first and second plates together to close the divide.

The ratchet mechanism in one form may include a ratchet recess in the top portion of the first plate and a ratchet wheel disposed in and removable from the ratchet recess. The ratchet recess includes a plurality of teeth around a circumference of the ratchet recess that extend radially inward towards a center of the ratchet recess. The ratchet wheel includes a pawl or pawl-like element configured to engage the ratchet teeth and allow the ratchet wheel to rotate in a first direction while preventing rotation in an opposite direction.

The first plate may further include a boss extending in an upward direction from a central portion of the ratchet recess, and a protrusion proximal to a top edge of the boss extending radially outward from a center of the boss, wherein the first fastener aperture extends through the boss. The ratchet wheel includes a central aperture having a ledge extending substantially circumferentially around the central aperture and extending radially inward toward a center of the central aperture. The central aperture is configured to receive the boss. A cut-out formed in the ledge is configured to allow the protrusion to pass through the central aperture when the cut-out and the protrusion are aligned, and the protrusion extends over the ledge when the ratchet wheel is disposed in the ratchet recess and the cut-out and the protrusion are misaligned.

The device may further include a pin configured to be inserted into a pin aperture extending through the second plate in a substantially perpendicular direction to the longitudinal axis of the second plate. The pin includes a deflectable prong and the second plate includes first and second prong receptacles. The first prong receptacle communicates with the pin aperture and is located distal to the second face. The second prong receptacle communicates with the pin aperture and is located proximal to the second face. The pin is in a first position in which an end of the pin is held within the pin aperture when the deflectable prong is engaged with the first prong receptacle; and a second position in which the end of the pin extends beyond the second face when the deflectable prong is engaged with the second prong receptacle.

The first plate may include a pin receptacle in the first face that is configured to align with the pin aperture and receive the end of the pin when the first and second plate are coupled to the bone and the divide is closed. The pin receptacle has a depth configured to cause the end of the pin to contact a bottom of the pin receptacle when the divide is closed to maintain the first and second plates spaced the distance apart.

It will be understood that the invention can be embodied in other configurations. While described in the context of two interengaging plates, these parts need not be plates per se, but could be in other shapes. Plates have been used in the current environment described hereafter, which is particular, but not limited, to a sternal resection. The sternum presents a rather planar outward facing surface, hence a plate-like structure for the device is particularly useful.

Conceptually, however, the broad concept is in one aspect to have two (or perhaps more) parts for the device that can be emplaced, either before or after the surgical separation (or break) across which the device will function to rejoin the separated parts. The device in this form has a ratchet mechanism which serves to draw the parts of the device together, and thus place the bone parts back into rough engagement. The ratchet mechanism could be located on an outward facing surface of the device, or could be formed internally, with a tool access area for turning the ratchet wheel. Preferably, the two (or more) parts of the fixation device also include one or more rigid element, such as rods or flanges for example, which will also span the distance across the divide and serve to further join the parts of the device, particularly against sheer forces (forces that would cause the parts to move relative to one another, either along the divide or into/out of the plane of the fixation device.

Another advantage of the invention in a preferred form is the ability to quickly separate the portions of the device in the event that the bones have to be re-separated post-fixation, as in an emergency procedure. In this form, a simple single cut needs to be made of the joinder element used with the ratchet mechanism, then the parts are movable laterally. To thereafter re-join the still emplaced parts, a new joinder element is used. The ratchet mechanism could be made replaceable to that end (pop-out pop-in), or conceivably could be designed simply to receive a new joinder element.

In other embodiment, other types of plates, fasteners, and ratchet type devices are disclosed herein.

BRIEF DESCRIPTION OF THE DRAWINGS

Embodiments of devices, systems, and methods are illustrated in the figures of the accompanying drawings which are meant to be exemplary and not limiting, in which like references are intended to refer to like or corresponding parts, and in which:

FIG. 3 illustrates a perspective view of a ratchet wheel of the first plate of FIG. 1 according to the disclosure;

FIG. 12 illustrates a tool for operating a ratchet wheel of the first plate according to the disclosure;

FIG. 50 illustrates a crimp lock type implantable fixation device according to the disclosure;

FIGS. 54-57 illustrate another implantable fixation device according to the disclosure;

DETAILED DESCRIPTION

While the embodiments described hereinafter are in the environment of an orthopaedic fixation device, system and method for use on the sternum, in particular, it should be appreciated that the disclosure has broader application. That could be, for instance, such as where bone or other body parts having suitable rigidity require closure or other relational organization, such as joining two opposing anatomical structures. This could be in the context of a traumatic break or other unintended separation, or as part of a surgical procedure. Thus, the present disclosure can have usefulness in contexts beyond fixation of bones which have been resected in surgery.

In general, the present disclosure relates to implantable fixation devices for rejoining opposed portions of a separated bone. Implantable is used in the sense that it is sub-cutaneous, but it is possible that applications leaving the fixation device external could be envisioned.

One such device which has been developed according to aspects of the invention in the context of joining two halves of the sternum, includes two corresponding plates that are configured to be aligned and coupled to a bone, such as a sternum, pre-resection of the bone or prior to cutting/separating the bone. The placement of the corresponding plates provides a gap between the edges of the plates that face one another allowing for and guiding a cutting tool for separating the bone. After the bone has been cut and the desired surgical procedure performed, the plates also assist in realigning and fixation of the bone portions. For example, at least one plate may include a ratchet mechanism that is configured to tighten a locking element and draw the two plates together and into alignment with one another.

Note here again, the fixation device could also be emplaced post-resection, although this is considered a less-advantageous use of the device as currently perceived. Also, the parts of the device need not be plates or planar elements, but this shape was considered most-desirable in the environment of a sternal rejoining device and system.

Figure 1:
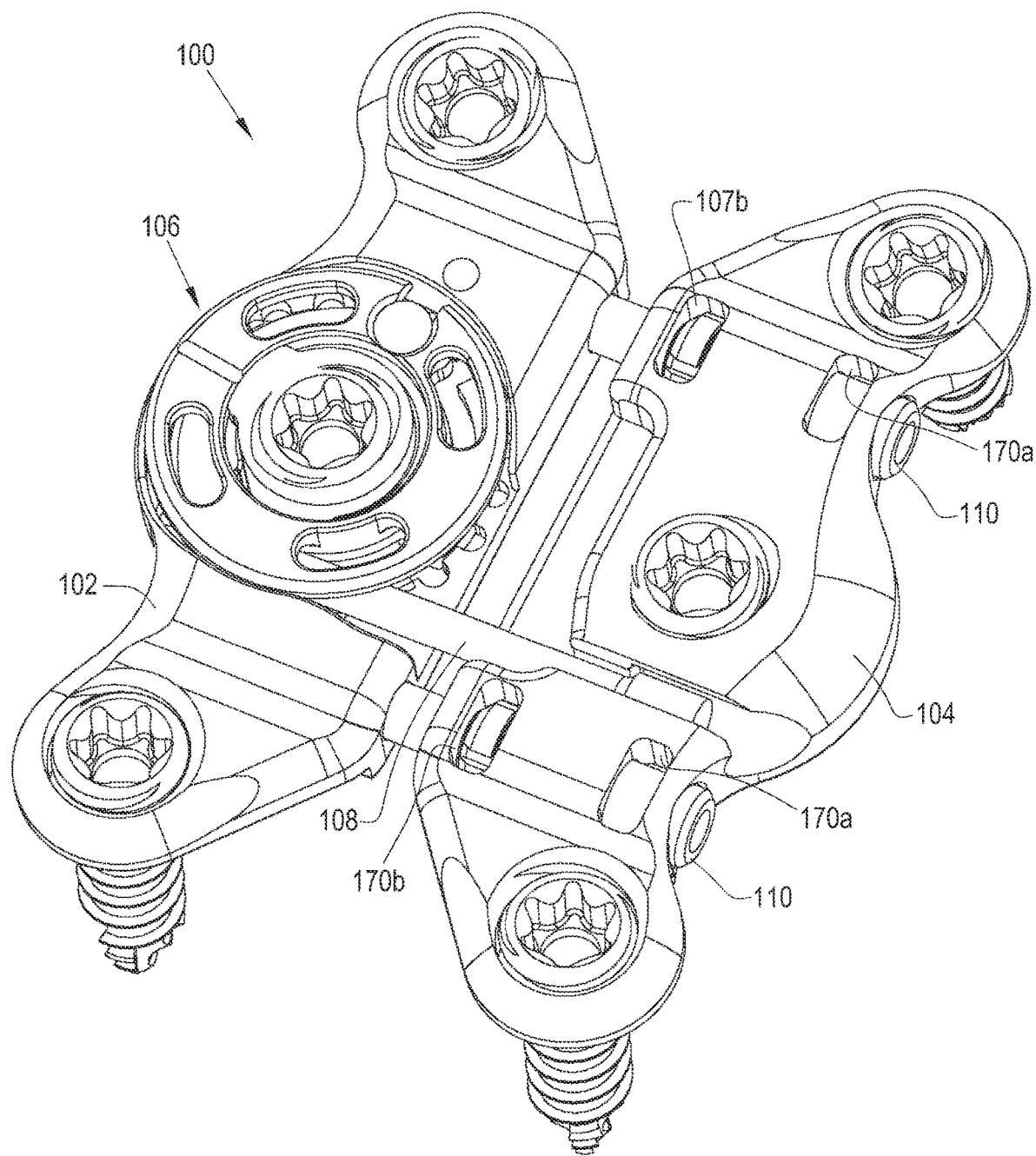
FIG. 1 illustrates a perspective view of an implantable fixation device according to an aspect of the disclosure.

FIGS. 1-5 illustrate an implantable fixation device 100 in the form of two plates according to an embodiment of the disclosure. As illustrated in FIG. 1, the fixation device 100 includes a first plate 102 and a second plate 104. The first plate 102 includes a ratchet mechanism 106 for use in tightening a locking element 108 to pull the first plate 102 and second plate 104 together, as will be more particularly described hereafter. One or more shear pins 110 may be inserted into the second plate 104 to assist in aligning the first plate 102 and second plate 104, and to resist longitudinal and transverse shear forces applied to bone portions post-separation. Other interengaging elements spanning the divide and serving to stabilize the adjacent plates against these forces can be envisioned.

Figure 2A:
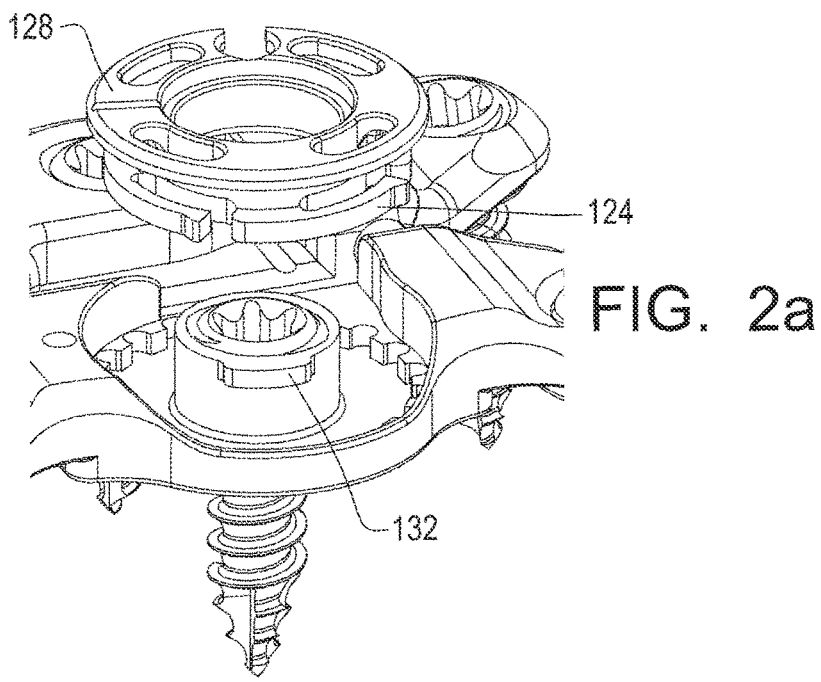
FIG. 2 illustrates an exploded view of a first plate of the implantable fixation device of FIG. 1 according to the disclosure.
Figure 2B:
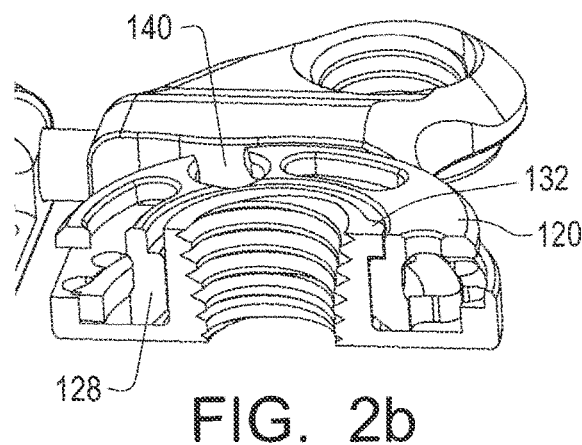
Figure 2C:
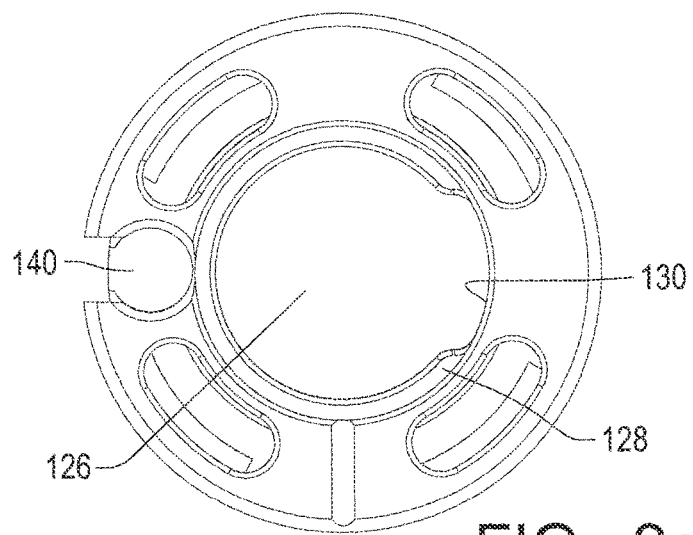

Referring to FIG. 2, the first plate 102 includes a first end 112, a second end 114, and a first face 116 configured to be positioned facing a face of the second plate 104, and the ratchet mechanism 106. The ratchet mechanism 106 includes a ratchet recess or well 118 and a ratchet wheel 120. The ratchet recess 118 is located in substantially a central portion of a top portion (i.e., facing away from a body/bone onto which the plate may be attached) of the first plate 102 between the first and second ends 112 and 114. As illustrated, the ratchet recess 118 includes a plurality of teeth 122 around a circumference of the ratchet recess 118 that extend radially inward towards a center of the ratchet recess 118. Other types of ratcheting mechanisms can be envisioned.

The ratchet wheel 120 is removably disposed in the ratchet recess 118. This will be more particularly described with relation to re-entry after an earlier fixation procedure, as for emergency reentry. Referring to FIGS. 2 and 3, the ratchet wheel 120 includes one or more pawls 124 configured to engage the teeth 122 and allow the ratchet wheel to rotate in one direction while preventing rotation in the opposite direction. As illustrated, the ratchet wheel 120 includes four pawls 124 and the ratchet recess 118 includes 20 teeth 122. This provides for a ratchet mechanism that locks, thereby preventing rotation in the opposite direction, at about each eighteen degree increment of rotation. However, it should be appreciated that the number of pawls 124 and teeth 122 may be increased or decreased to provide a ratchet mechanism that locks, thereby preventing rotation in the opposite direction, at any desired degree increment of rotation.

The ratchet wheel 120 also includes an aperture 126 including a ledge 128 extending substantially circumferentially around the aperture 126 and extending radially inward toward a center of the aperture 126. The ledge 128 includes a cut-out or groove 130 configured to receive a protrusion 132 of a boss 134. The boss 134 extends in an upward direction from a central portion of the ratchet recess 118 and includes the protrusion 132 proximal to a top edge of the boss 134 that extends radially outward from a center of the boss 134. This protrusion and cut-out arrangement allows for the ratchet wheel 120 to be disposed in and removed from the ratchet recess 118 when the cut-out 130 is aligned with the protrusion 132, and prevents the ratchet wheel 120 from being disposed in or removed from the ratchet recess 118 when the cut-out 130 is not aligned with the protrusion 132.

When the ratchet wheel 120 is installed in the ratchet recess 118, the boss 134 extend into the aperture 126 of the ratchet wheel 120 and the protrusion 132 extends over the ledge 128 to prevent the ratchet wheel 120 from accidentally being removed from the ratchet recess 118.

To facilitate ease of assembly and disassembly, the ratchet wheel 120 may include an indicator 136 and the first plate 102 may include a corresponding indicator 138, that when aligned indicate that the cut-out 130 is aligned with the protrusion 132. This allows a use to visually identify the correct position of the ratchet wheel 120 with respect to the first plate 102 to install or remove the ratchet wheel 120 from the first plate 102.

The ratchet wheel 120 also includes a locking element capture receptacle 140 and an annular channel 142. The locking element capture receptacle 140 is configured to receive an end of the locking element 108 (illustrated in FIG. 1). The channel 142 is configured to receive and allow the locking element 108 (illustrated in FIG. 1) to be coiled around the ratchet wheel 120 to tighten the locking element 108 (illustrated in FIG. 1), as described in further detail hereinafter.

The ratchet wheel 120 may also include one or more tool engaging features 144, illustrated as oblong apertures. The tool engaging features 144 are configured to receive a corresponding male feature of a tool for use in rotating the ratchet wheel 120 to coil the locking element 108 (illustrated in FIG. 1) around the ratchet wheel 120.

In another embodiment, the ratchet wheel 120 may be shaped to be received in a drive receptacle of a tool. For example, referring to FIGS. 9 and 10, a top portion of ratchet wheel 120' may be configured to be received and engaged by a drive receptacle of a tool for use in rotating the ratchet wheel 120' to coil the locking element 108 around the ratchet wheel 120'.

Referring to FIG. 2, the first plate 102 includes a cut-out or area of reduced wall height 146 proximal to the face 116. This allows the locking element 108 (illustrated in FIG. 1) to extend from the first plate 102 and be coupled to the second plate 104, as described in further detail hereinafter.

The first plate 102 may include one or more shear pin receiving receptacles 148 in the face 116. The receiving receptacles 148 are configured to receive corresponding shear pins 110 (illustrated in FIG. 1) extending from the second plate 104. This assists in aligning the first and second plates 102 and 104 when the implantable fixation device 100 is installed and used. While pins are described to this end in this particular embodiment, other collateral engaging pieces or portions can be envisioned. Overlying flanges, tongue-and-groove mating parts, press-in spanning members and so forth could be applied. Pins are disclosed in this embodiment, as easily manipulated to snugly engage across the divide and between the two plate parts.

The first plate may also include one or more threaded fastener apertures configured to receive corresponding fasteners 150 to couple the first plate 102 to a bone or other body part. As illustrated in FIG. 2, the threaded fastener apertures include a first aperture 152a positioned proximal to the first end 112, a second aperture 152b positioned proximal to the second end 114, and a third aperture 152c in the boss 134. The apertures 152a-c may have a circular shape, oblique shape, or other shape, or a combination thereof. For example, the first and second apertures 152a and 152b may be oblique and the third aperture 152c may be circular. While there are three fasteners 150 and three corresponding threaded fastener apertures 152a-c, there may be more or less than three in the first plate 102 and the fasteners may be screws, pins, rivets, or other types of fasteners, etc.

Figure 4:
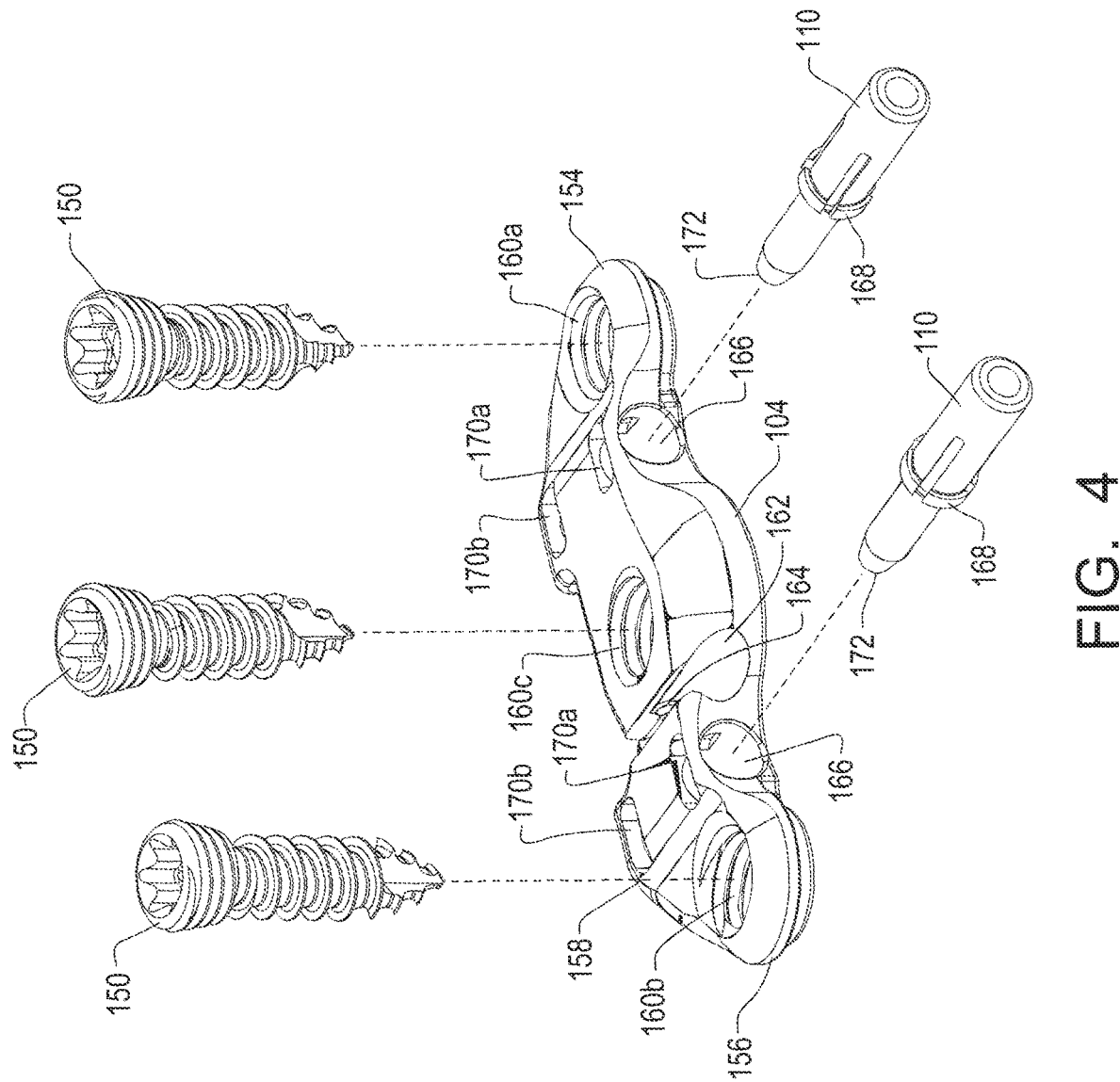
FIG. 4 illustrates an exploded view of a second plate of the implantable fixation device of FIG. 1 according to the disclosure.

Referring to FIG. 4, the second plate 104 includes a first end 154, a second end 156, and a second face 158 configured to be positioned facing the first face 116 of the first plate 102 (illustrated in FIG. 2) in an opposed relationship. Similar to the first plate 102, the second plate 104 may include one or more threaded fastener apertures configured to receive corresponding fasteners 150 to couple the second plate 104 to a bone or other body part. As illustrated in FIG. 4, the threaded fastener apertures include a first aperture 160a positioned proximal to the first end 154, a second aperture 160b positioned proximal to the second end 156, and a third aperture 160c substantially in a center of the second plate 104. The apertures 160a-c may have a circular shape, oblique shape, or other shape, or a combination thereof. For example, the first and second apertures 160a and 160b may be oblique and the third aperture 160c may be circular. While there are three fasteners 150 and three corresponding threaded fastener apertures 160a-c, there may be more or less than three in the second plate 104 and the fasteners may be screws, pins, rivets, or other types of fasteners, etc.

The second plate 104 may also include a locking element capture channel 162 formed in a top of the second plate 104 and extending across the second plate 104 in a substantially perpendicular direction to a longitudinal axis of the second plate 104. The locking element capture channel 162 is configured to receive an end of the locking element 108 (illustrated in FIG. 1), as described in further detail hereinafter. The locking element capture channel 162 may also include a stop or ledge 164 configured to prevent the locking element 108 (illustrated in FIG. 1) from being pulled out of the channel in a direction of the face 158.

As illustrated in FIG. 3, one or more apertures 166 extend through the second plate 104 in a substantially perpendicular direction to the longitudinal axis of the second plate 104. The apertures 166 are configured to receive corresponding shear pins 110. One aperture 166 may be positioned between the first aperture 160a and the third aperture 160c, and located to align with one of the receiving receptacles 148 of the first plate 102 (illustrated in FIG. 2). Another aperture 166 may be positioned between the second aperture 160b and the third aperture 160c, and located to align with the other of the receiving receptacles 148 of the first plate 102 (illustrated in FIG. 2).

The shear pins 110 may include deflectable prongs 168 and the second plate may include corresponding prong receiving receptacles configured to receive the prongs 168 to hold the shear pins 110 in the second plate 104. As illustrated in FIGS. 1 and 4, the second plate 104 includes first prong receiving receptacles 170a and second prong receiving receptacles 170b. Each first prong receiving receptacle 170a communicates with a corresponding one of the apertures 166, and is located distal to the face 158. Similarly, each second prong receiving receptacle 170b communicates with a corresponding one of the apertures 166, and is located proximal to the face 158.

Figure 7:
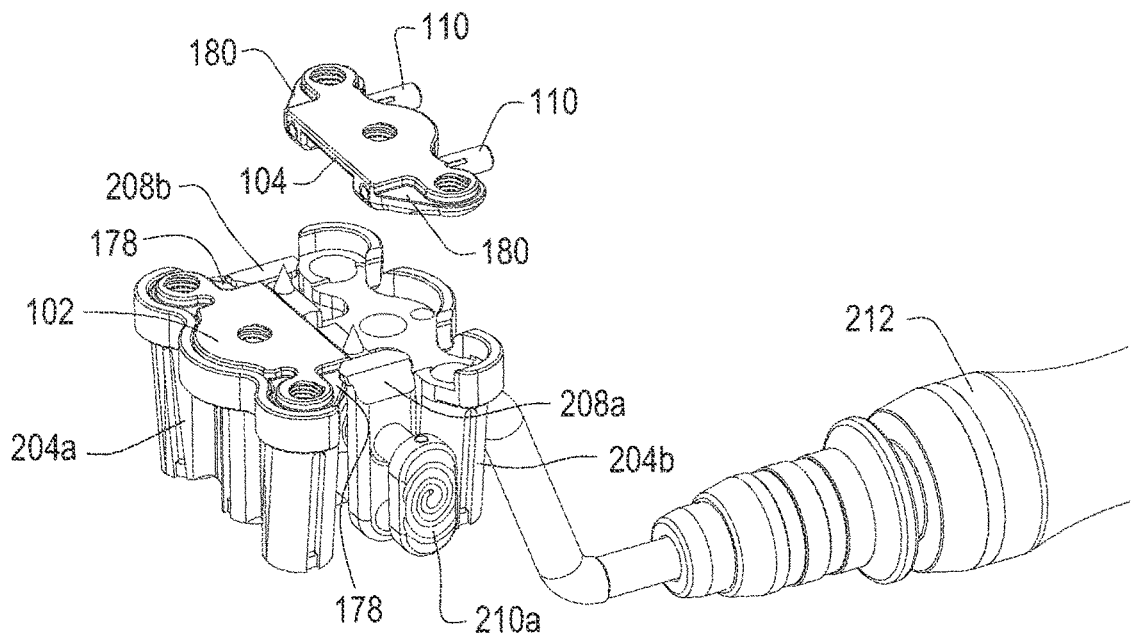
FIG. 7 illustrates the first and second plates being installed in the fixation device positioning holder according to the disclosure.

Referring to FIGS. 4 and 7, the first prong receiving receptacles 170a correspond to a first position of the shear pins 110 (as illustrated in FIG. 7). In the first position, the deflectable prongs 168 of the shear pins 110 are engaged with the first prong receiving receptacles 170a. In this position, ends 172 of the shear pins 110 are positioned within the apertures 166 and do not extend past the face 158 of the second plate 104.

Figure 5:
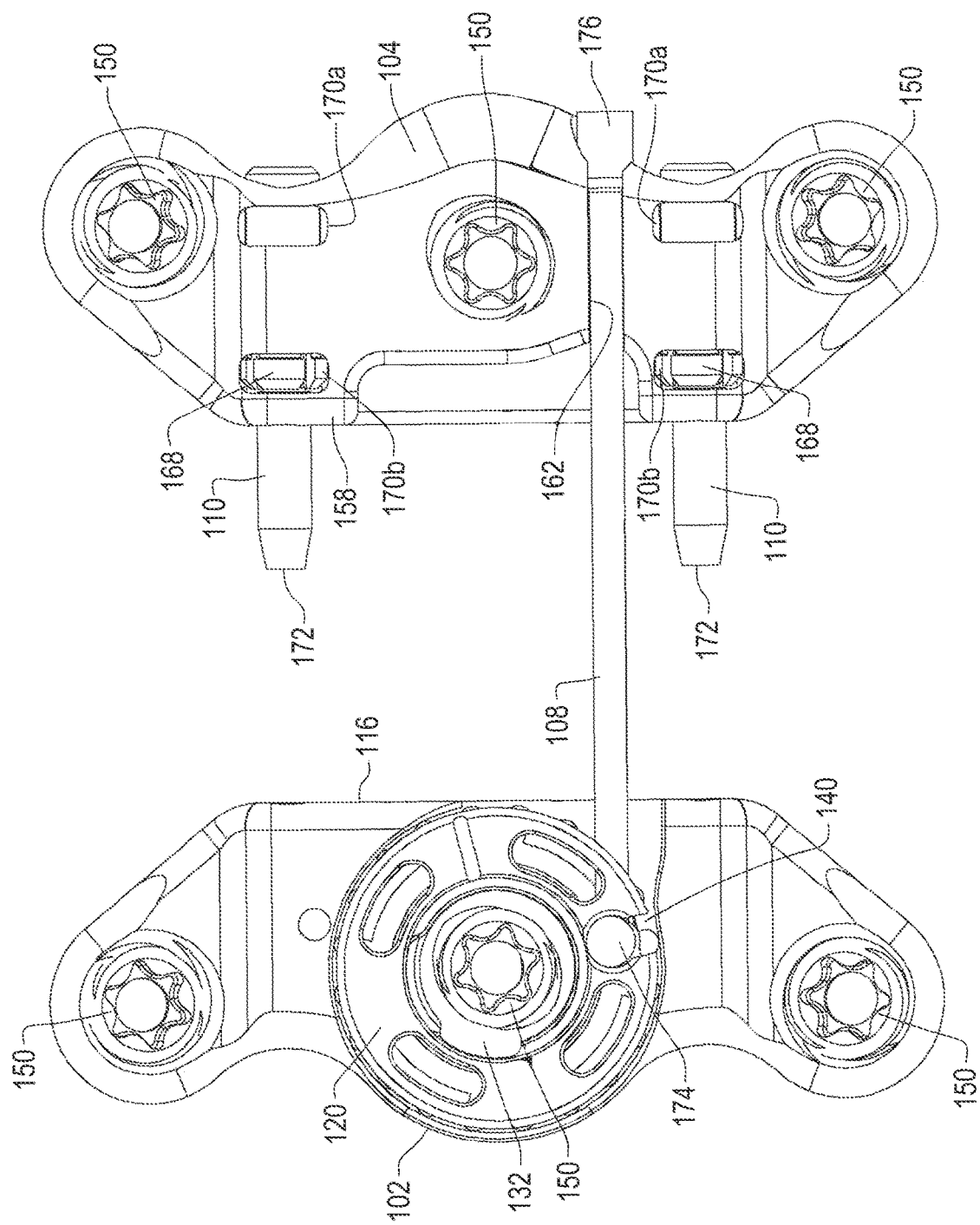
FIG. 5 illustrates the first and second plates aligned in a first position.

Referring to FIGS. 4 and 5, the second prong receiving receptacles 170b correspond to a second position of the shear pins 110 (as illustrated in FIG. 5). In the second position, the deflectable prongs 168 of the shear pins 110 are engaged with the second prong receiving receptacles 170b. In this position, the ends 172 of the shear pins 110 extend past the face 158 of the second plate 104, and extend into the receiving receptacles 148 in the face 116 of the first plate 102 (illustrated in FIG. 2) when the implantable fixation device 100 is installed and used to hold two corresponding bone portions together.

Referring to FIG. 5, the locking element 108 may be a bendable rod and have a first end 174 and a second end 176. The first end 174 may include a first engagement portion that extends substantially perpendicular to a longitudinal axis of the locking element 108. The first end 174 may be installed in the locking element capture receptacle 140 of the ratchet wheel 120. The second end 176 may include a second engagement portion having a diameter greater than a remainder of the locking element 108. The second end 176 may be installed in the locking element capture channel 162 of the second plate 104. The locking element could take other forms, such as a sturdy wire or the like. Conceptually, it is an elongate member that is capable of being wound upon the ratchet wheel.

When the locking element 108 is installed and the ratchet wheel 120 is rotated, the locking element 108 is coiled around the ratchet wheel 120 to urge the first plate 102 and second plate 104 together and into alignment with one another. In this respect, the second end 176 may contact the stop or ledge 164 of the locking element capture channel 162 and allow the first plate 102 and second plate 104 to be pulled together.

Figure 6:
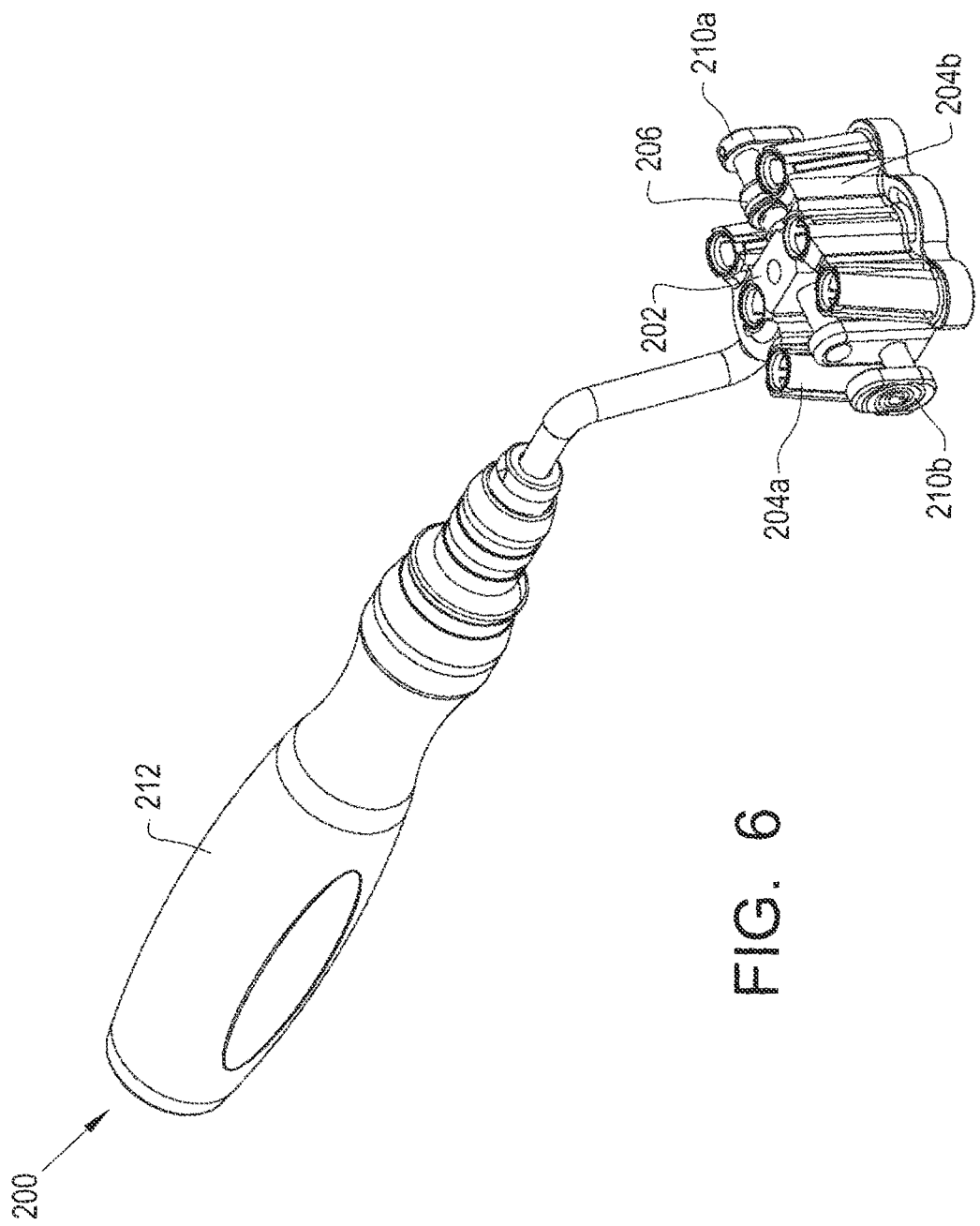
FIG. 6 illustrates a fixation device positioning holder according to the disclosure.
Figure 8:
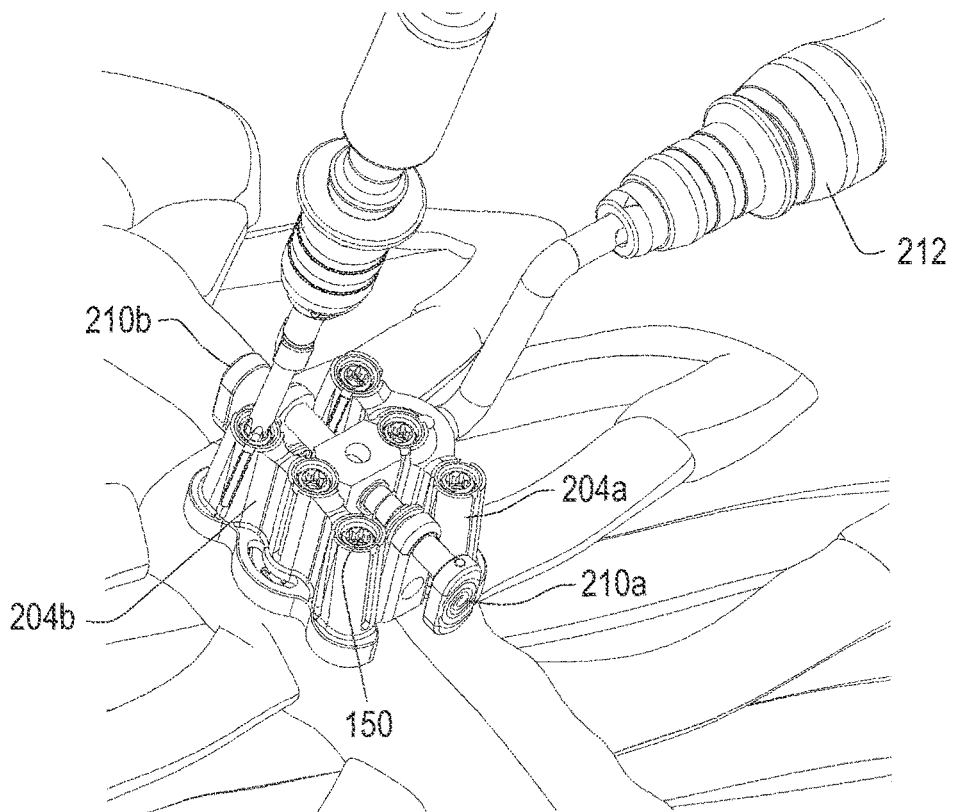
FIG. 8 illustrates the first and second plates being affixed to a bone according to the disclosure.

The first plate 102 and second plate 104 may be configured to be used in conjunction with a fixation device positioning holder. Referring to FIGS. 6-8, the positioning holder 200 includes a body 202 including a first set of fastener guides 204a and a second set of fastener guides 204b on opposite sides of the body 202, a compression attachment mechanism 206, and attachment feet 208a and 208b. A version of a positioning holder is disclosed in U.S. Ser. No. 62/039,672, the disclosure of which is incorporated herein by reference, and to which priority is claimed.

The first and second sets of fastener guides 204a and 204b provide a housing to guide fasteners 150 for insertion into the threaded fastener apertures 152a-c of the first plate 102 (illustrated in FIG. 2) and the threaded fastener apertures 160a-c of the second plate 104 (illustrated in FIG. 4). Each of the first and second sets of fastener guides 204a and 204b may include cylindrical hollow tube like guide barrels that are positioned and oriented to align with the threaded fastener apertures 152a-c of the first plate 102 (illustrated in FIG. 2) and the threaded fastener apertures 160a-c of the second plate 104 (illustrated in FIG. 4). The positioning holder 200 may also be used to guide a driver and/or drill depending on the application, and/or to guide other instruments, for example, to place markings, pegs, headless pins, screws, etc. in a bone.

The compression attachment mechanism 206 may include a spring loaded mechanism that when compressed causes a distance between the attachment feet 208a and 208b to increase and when released causes the distance between the attachment feet 208a and 208b to decrease and mate with corresponding recesses 178 in the first plate 102 and corresponding recessed 180 in the second plate 104.

The attachment feet 208a and 208b serve to hold the first and second plates 102 and 104 in the positioning holder 200 at a predetermined distance from each other. As illustrated in FIG. 7, the attachment feet 208a and 208b hold the first and second plates 102 and 104 in a coplanar arrangement, with the threaded fastener apertures 152a-c of the first plate 102 (illustrated in FIG. 2) aligned with the respective guide barrels of the first set of fastener guides 204a and the threaded fastener apertures 160a-c of the second plate 104 (illustrated in FIG. 4) aligned with the respective guide barrels of the second set of fastener guides 204b.

The compression attachment mechanism 206 allows for the positioning holder 200 to be coupled to and uncoupled from the first and second plates 102 and 104 quickly and easily, simply by compressing the spring loaded mechanism. For example, when gripping portions 210a and 210b are compressed, the distance between the feet 208a and 208b is increased. This allows the first and second plates 102 and 104 to be placed in the positioning holder 200, and when the compression force applied to the gripping portions 210a and 210b is released, the distance between the feet 208a and 208b decreases and the feet 208a and 208b mate with the recesses 178 and 180 of the first and second plates 102 and 104, respectively.

The positioning holder 200 may include a handle 212 coupled to the fixation device 100 for ease of assembly of elements and placement of the plates (such as the plates 102 and 104). The handle 212 may have an ergonomic design for comfort and control of the positioning holder 200. The handle 212 may also be angled to accommodate soft tissues and various surgical approaches.

The positioning holder 200 may also include one or more spikes (not shown) extending from a bottom of the positioning holder 200 to assist in placing and holding the positioning holder 200 and the first and second plates 102 and 104 in a proper orientation as the fasteners 150 are driven to couple the first and second plates 102 and 104 to a bone or other portion of a patient's body.

In an embodiment, the first and second plates 102 and 104 may be used in a sternal resection procedure. For example, referring to FIG. 9, soft tissue may be dissected from a surface of the sternum to allow for complete visualization of the bone, illustrated as block 902. In addition to dissecting the soft tissue from the sternum, bony calluses, if present, may also be removed from the midline and sternal surface to allow for proper anatomical reduction and plate placement.

Figure 9:
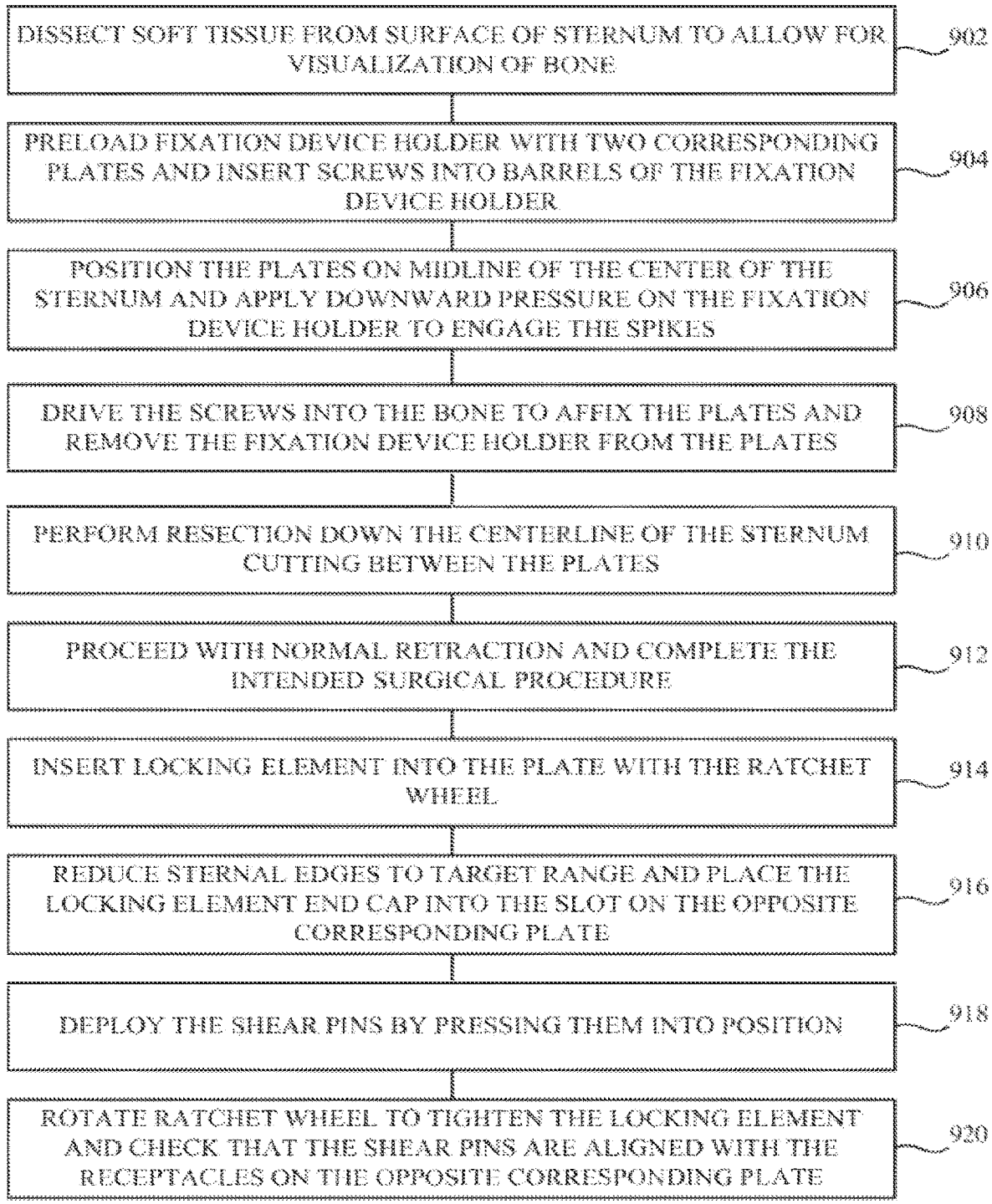
FIG. 9 is a block flow diagram of a method of installing and using the implantable fixation device according to the disclosure.

Referring to FIGS. 7 and 9, the first and second plates 102 and 104 may be loaded into the positioning holder 200, and the fasteners 150 may be inserted into the first and second sets of fastener guides 204a and 204b, illustrated as block 904. Referring to FIGS. 8 and 9, using the handle 212 the first and second plates 102 and 104 are positioned on a midline of a center of a sternum, illustrated as block 906. Once the target position is achieved, gentle downward pressure on the positioning holder 200 may be applied to engage the periosteal spikes of the positioning holder 200 to stabilize the position of the first and second plates 102 and 104 on the sternum.

The fasteners 150 may then be driven into the bone of the sternum using a tool, such as a bone drill, illustrated as block 908. It should be appreciated that if dense cortical bone is present, utilization of a pre-drilled hole may be advisable. Once the fasteners 150 are driven, the gripping portions 210a and 210b are compressed to disengage the attachment feet 208a and 208b from the first and second plates 102 and 104 and remove the positioning holder 200, illustrated as block 908. Depending on the length of resection, more than one implantable fixation device 100 may be installed by repeating the steps described herein.

Figure 10:
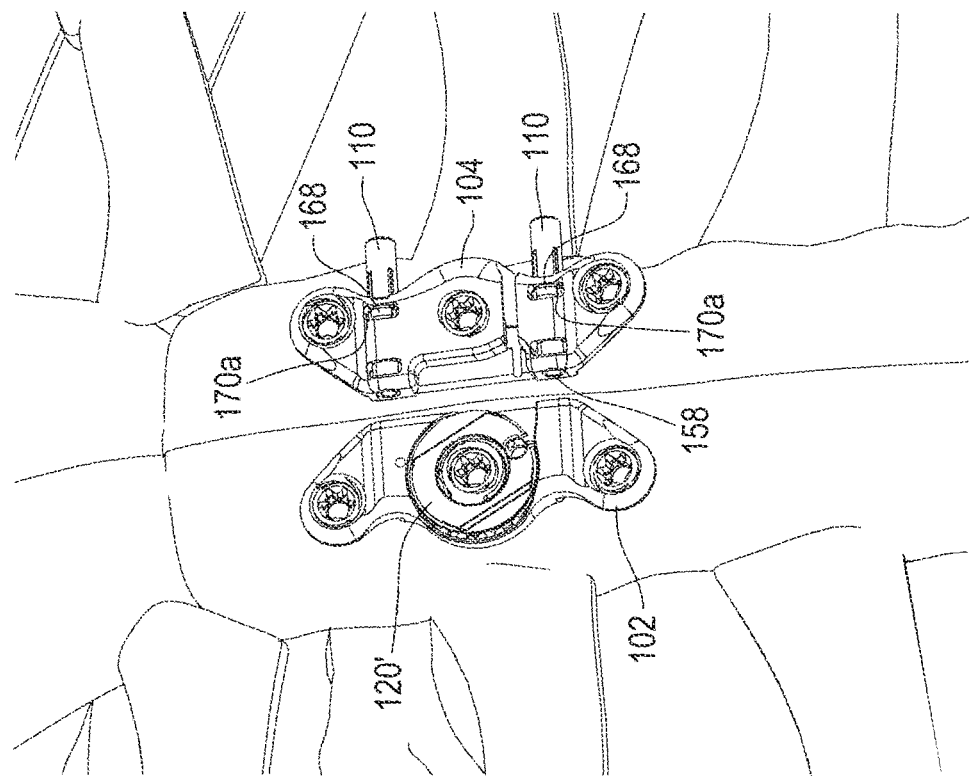
FIG. 10 illustrates the first and second plates of FIG. 1 aligned and oriented in a pre-resection position according to the disclosure.

Referring to FIGS. 9 and 10, sternal resection may then be performed. The first and second plates 102 and 104 are installed with a gap between the faces 116 and 158 of the respective first and second plates 102 and 104. Additionally, the first and second plates 102 and 104 are initially installed with the locking element 108 (illustrated in FIG. 5) removed, and the shear pins 110 are in the first position (i.e., the deflectable prongs 168 are engaged with the first prong receiving receptacles 170a).

A cutting tool may be used to cut the sternum between the first and second plates 102 and 104, using the first and second plates 102 and 104 as a guide, illustrated as block 910. The sternum may then be retracted and a surgical procedure performed, illustrated as block 912.

Figure 11:
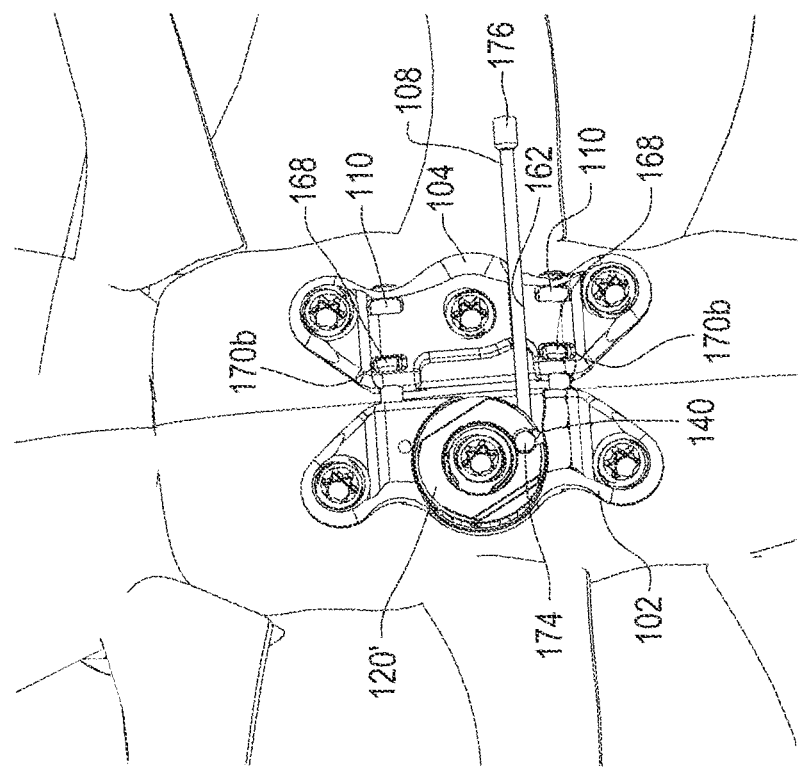
FIG. 11 illustrates the first and second plates of FIG. 1 aligned and oriented in a first post-resection position prior to operation of a ratchet mechanism according to the disclosure.

Referring to FIGS. 9 and 11, after the surgical procedure is complete, the first end 174 of the locking element 108 is seated in the locking element capture receptacle 140 of the ratchet wheel 120', illustrated as block 914. The cut portions of the sternum may be reduced back together and the second end 176 is seated in the locking element capture channel 162 of the second plate 104, illustrated as block 916. The ratchet wheel 120' is rotated and the locking element 108 is coiled around the ratchet wheel 120' to urge the first plate 102 and second plate 104 together and into alignment with one another. The ratchet wheel 120' or 120 may be rotated, for example, using tool 300 illustrated in FIG. 12. In an embodiment, the tool 300 includes a driving end 302 having male protrusions that engage the tool engaging features 144 of the ratchet wheel 120.

Figure 13:
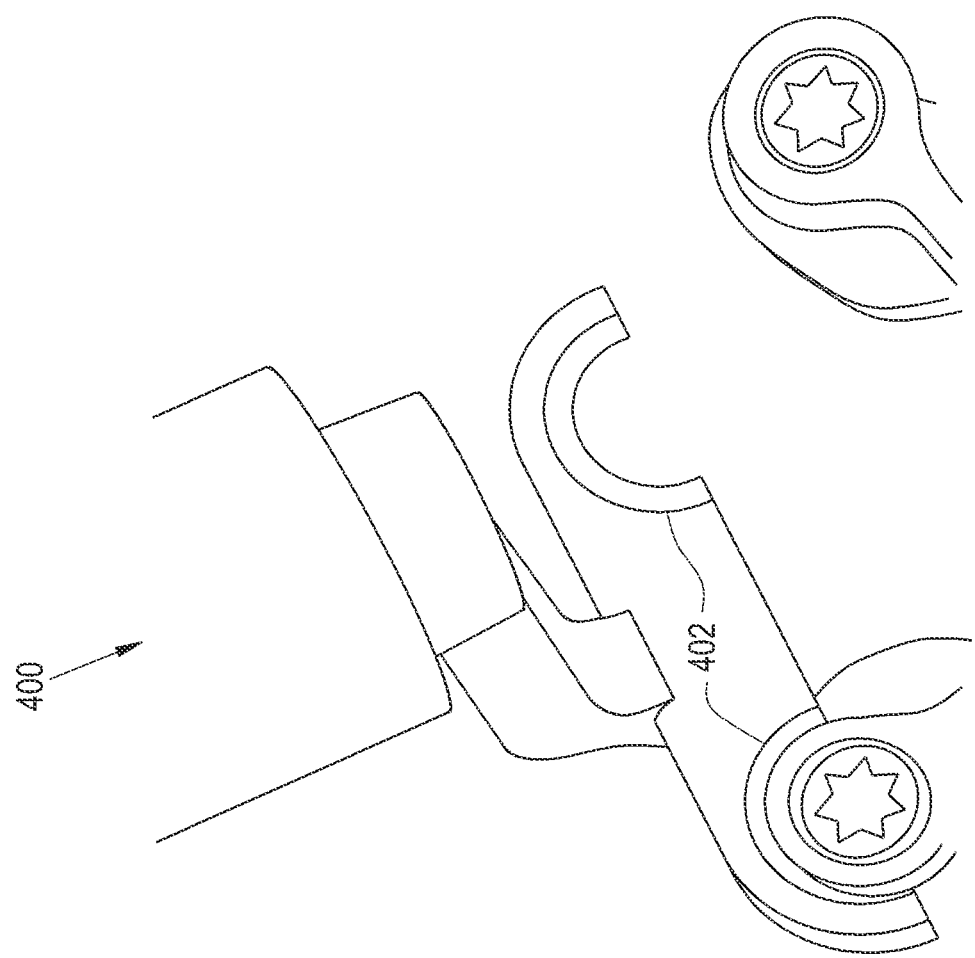
FIG. 13 illustrates a reduction tool for aligning and holding the first and second plates post-resection according to the disclosure.

Gross sternum reduction may be achieved using normal methods including manual external pressure, retraction instruments, wires, etc. Referring to FIG. 13, a reduction/alignment tool 400 may be used to bring the sternal edges into close apposition. As illustrated, the tool 400 includes plate engaging receptacles 402 configured to engage the first ends 112 and 154 or second ends 114 and 156 of the first and second plates 102 and 104, respectively, to hold and align the first and second plates 102 and 104. For example, the first ends 112 and 154 of the first and second plates 102 and 104, respectively, into the plate engaging receptacles 402 and a medial force may be applied on the instrument to bring the sternal edges closer together.

Figure 14:
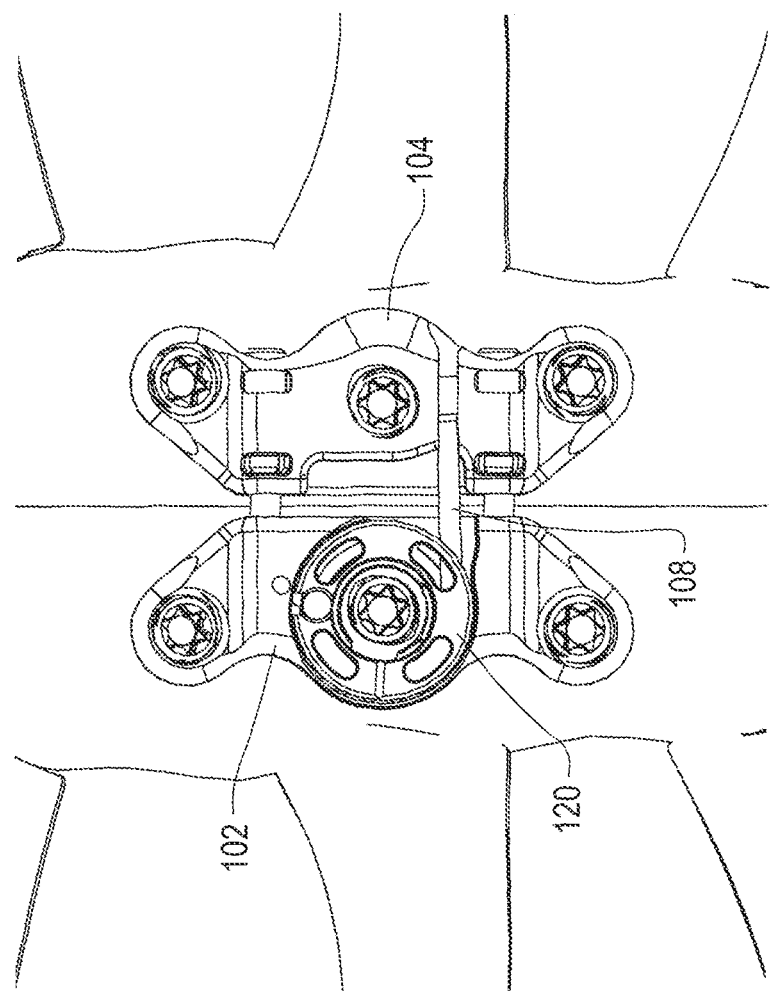
FIG. 14 illustrates the first and second plates of FIG. 1 post-resection according to the disclosure.

Referring back to FIGS. 9 and 11, the shear pins 110 may also be deployed to the second position by pressing them into the second plate 104 in a direction of the first plate 102, illustrated as block 918. This causes the deflectable prongs 168 of the shear pins 110 to engage the second prong receiving receptacles 170b. Referring to FIGS. 9 and 14, final approximation of the sternum is achieved by rotating the ratchet wheel 120 to cause the locking element 108 to be coiled around the ratchet wheel 120. A series of audible clicks may occur as the ratchet wheel 120 is rotated. The sternal edges will be drawn closer into apposition with each click of the ratchet wheel 120, illustrated as block 920.

During the final approximation, it should be ensured that the shear pins 110 are aligned with the receiving receptacles 148 in the face 116 (illustrated in FIG. 2) of the first plate 102, illustrated as block 920. Use of the reduction/alignment tool 400 may be helpful in achieving alignment. As the first and second plates 102 and 104 are brought closer together, the shear pins 110 extend into the receiving receptacles 148 in the face 116 (illustrated in FIG. 2) of the first plate 102. The receiving receptacles 148 may have a depth configured to allow the ends 172 (illustrated in FIG. 4) of the shear pins 110 to contact a bottom of the receiving receptacles 148 (illustrated in FIG. 2) to maintain the first and second plates 102 and 104 with the gap (described above) between them upon final approximation of the sternum.

Figure 15:
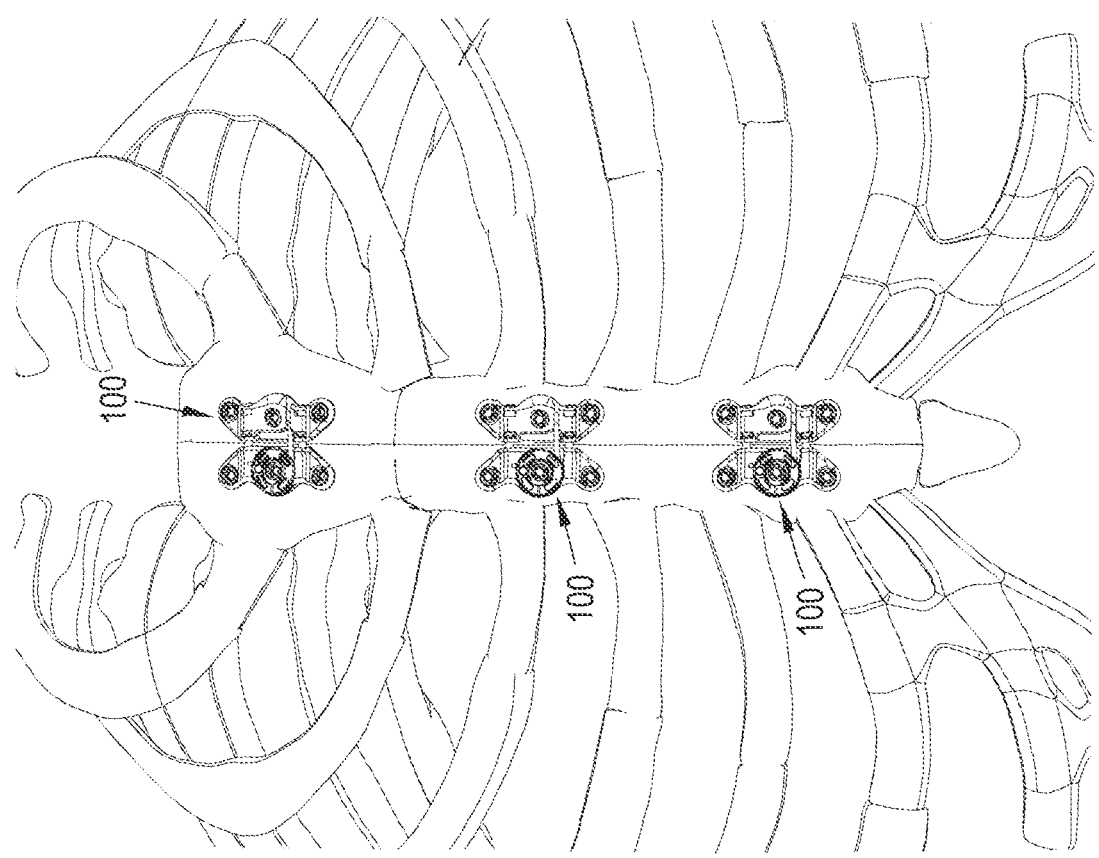
FIG. 15 illustrates a plurality of first and second plates post-resection as they might be located according to the disclosure.
Figure 16:
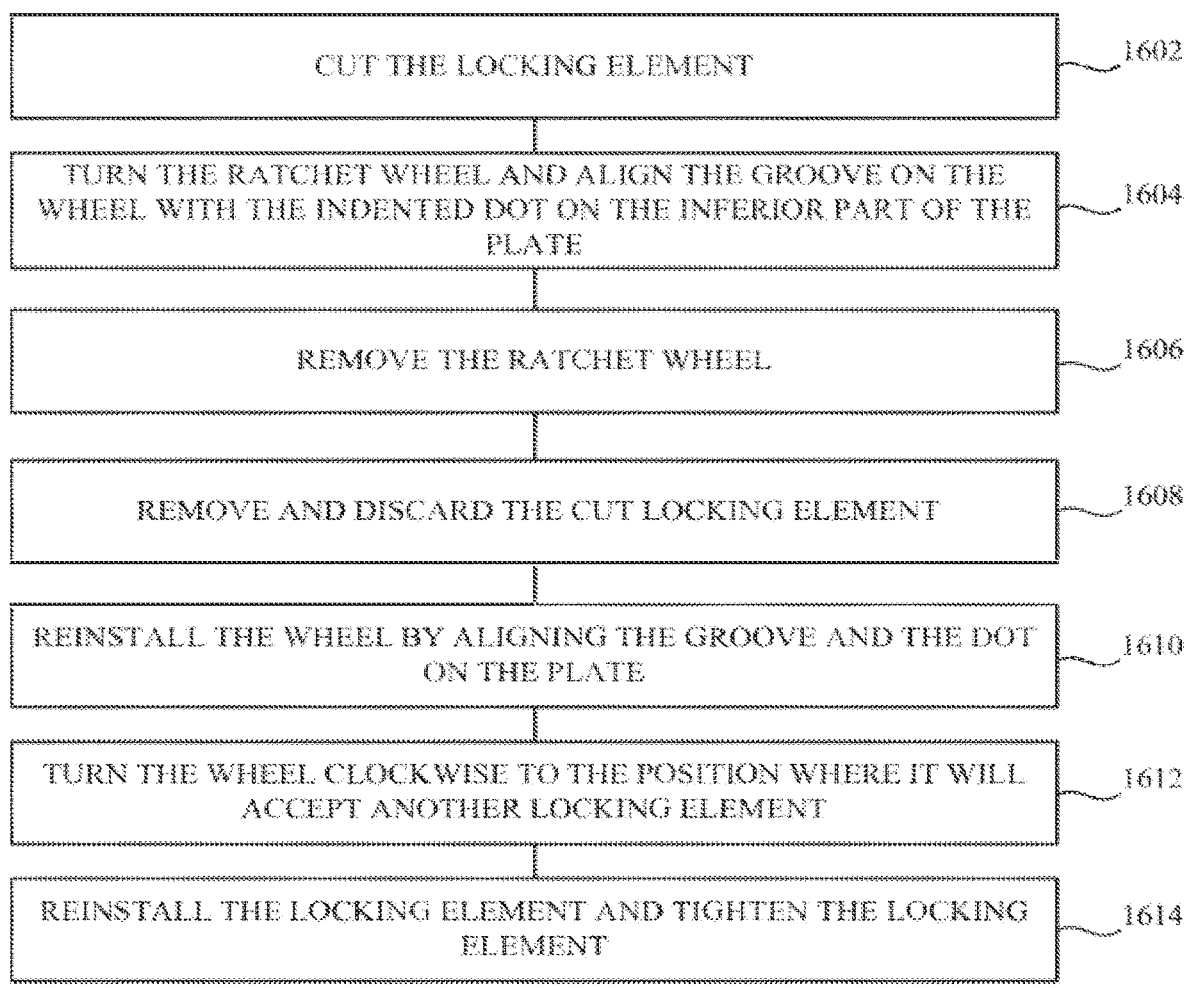
FIG. 16 is a block flow diagram of a method of using the implantable fixation device for reentry/re-resection of the bone according to the disclosure.
Figure 17:
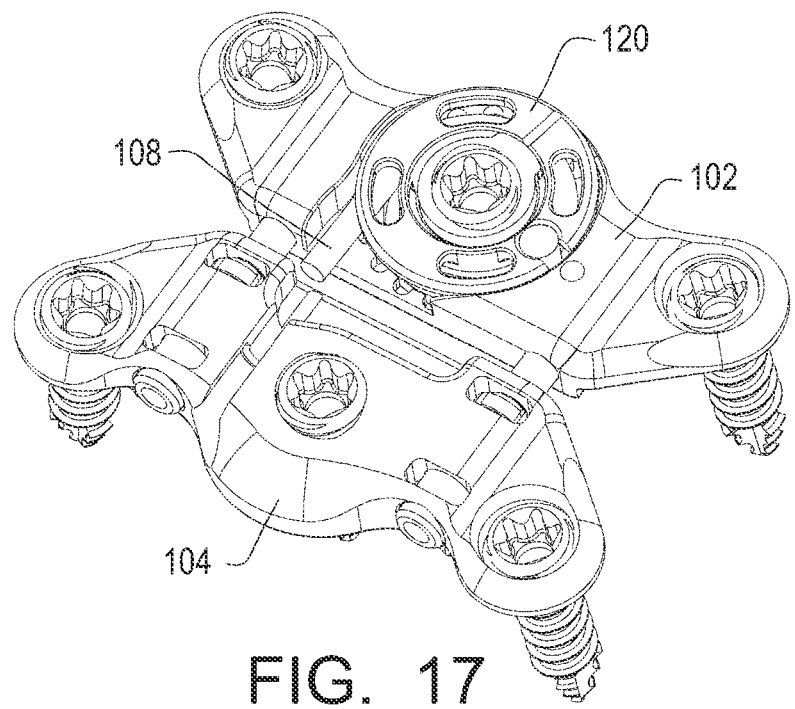
FIGS. 17 through 20 illustrate a locking element being cut and removed according to the disclosure.
Figure 18:
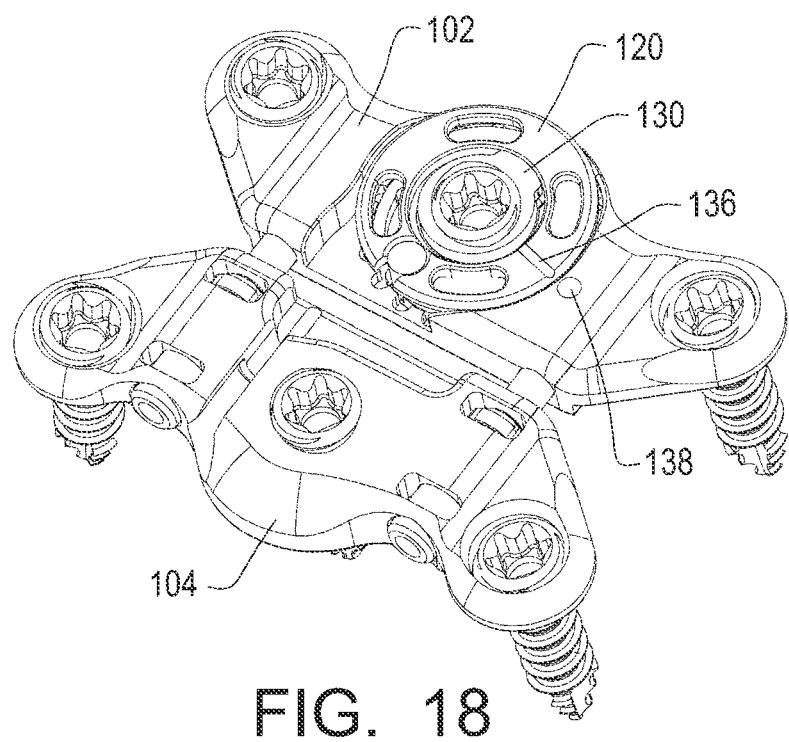
Figure 19:
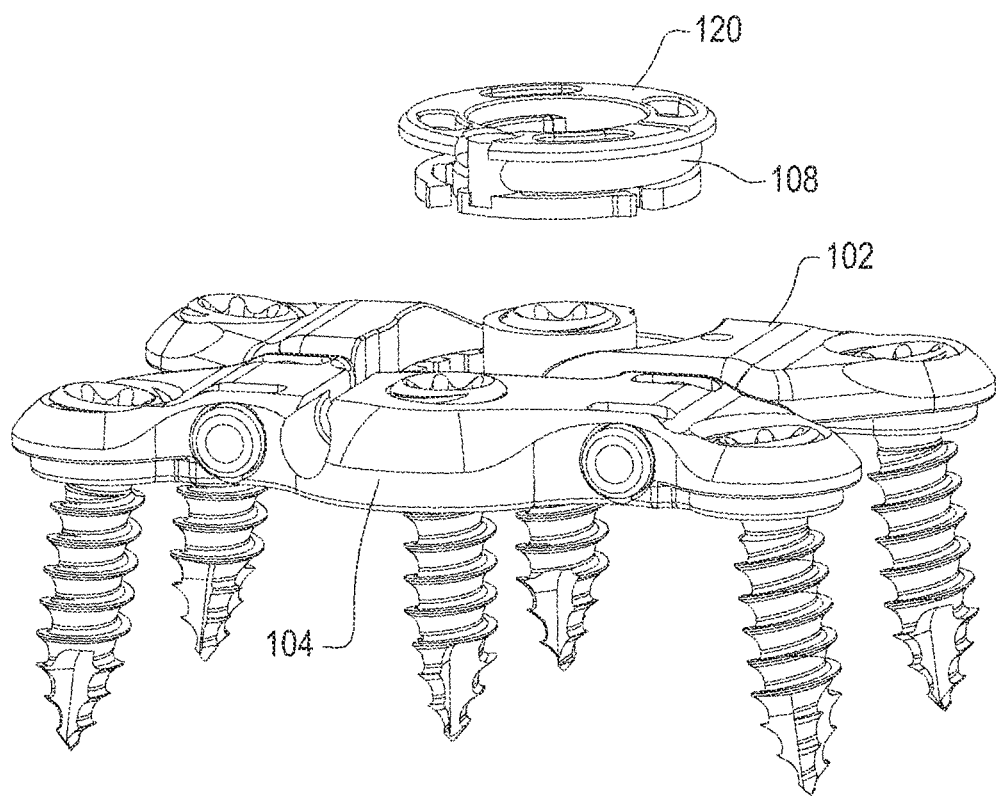

The steps described herein may be repeated for each implantable fixation device 100 that is used. When using multiple implantable fixation devices 100, the procedure may be repeated by alternating reduction incrementally from implantable fixation device 100 to implantable fixation device 100 until complete closure is achieved. For example, referring to FIG. 15, a middle implantable fixation device 100 may be incrementally tightened, a top implantable fixation device 100 may then be incrementally tightened, and then a bottom implantable fixation device 100 may be incrementally tightened. This may be repeated until the sternum is completely closed and the implantable fixation devices 100 are tightened together.

Once the implantable fixation device(s) 100 are tightened, the soft tissue may be closed in a normal fashion. It should be appreciated that sternal/cerclage wires may also be used in conjunction with the implantable fixation device(s) 100 if desired.

If emergent reentry is necessary, the fixation device(s) 100 allow for rapid access to the chest cavity. One option is to cut the locking element 108. Referring to FIGS. 16-22, the locking element 108 may be cut, for example using surgical scissors or other tool, illustrated as block 1602 and in FIG. 17. The ratchet wheel 120 may then be rotated to align the indicator 136 on the ratchet wheel 120 and the indicator 138 on the first plate 102, illustrated as block 1604 and in FIG. 18. As described above, when the indicators 136 and 138 are aligned, the cut-out 130 is aligned with the protrusion 132 (illustrated in FIG. 2). The ratchet wheel 120 may then be removed from the first plate 102, along with the cut portion of the locking element 108 engaged with the ratchet wheel 102, illustrated as block 1606 and in FIG. 19.

Figure 20:
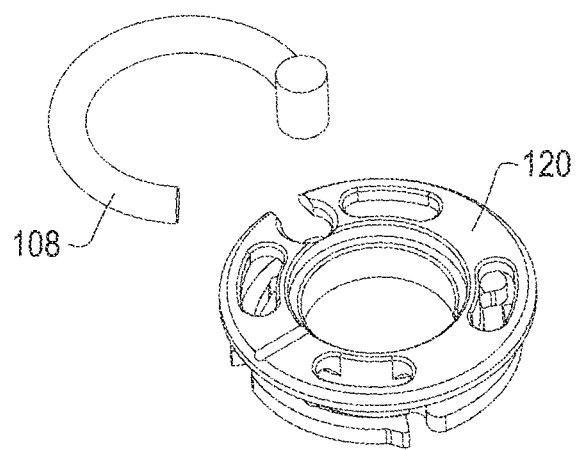
Figure 21:
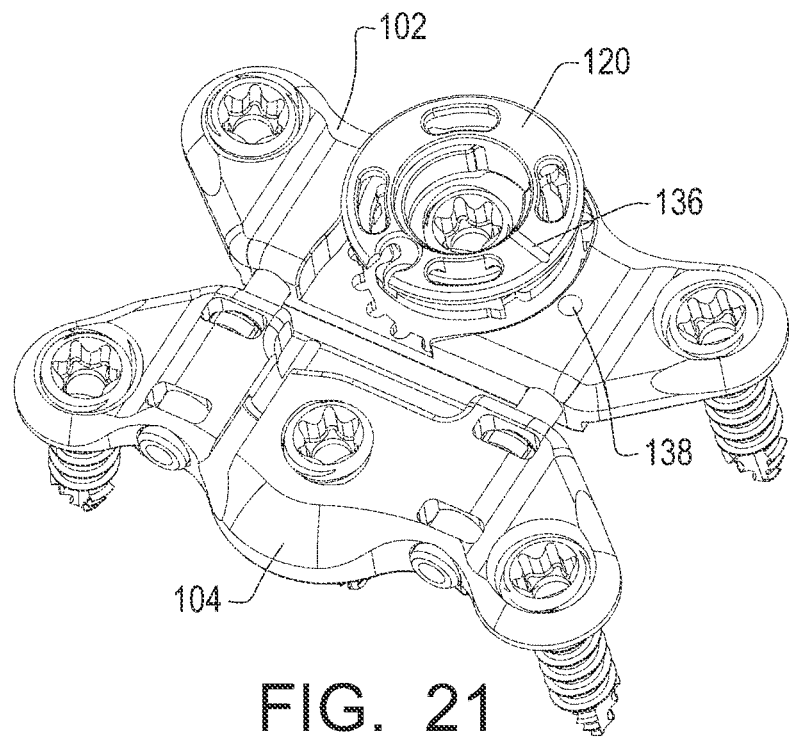
FIGS. 21 and 22 illustrate the ratchet wheel being reinstalled after removal of the locking element.
Figure 22:
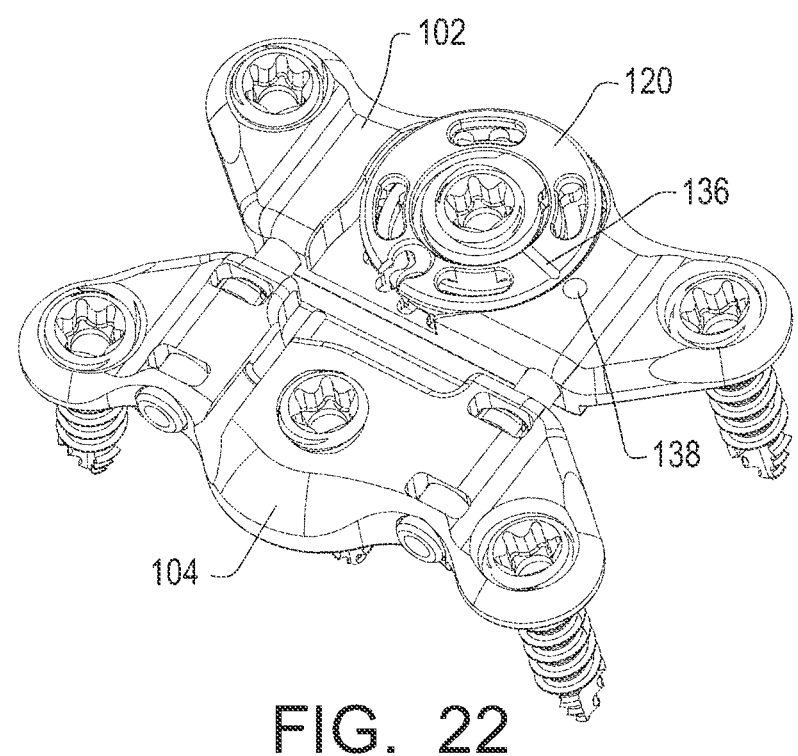

The coiled portion of the cut locking element 108 may then be removed from the ratchet wheel 120 and discarded, along with the corresponding portion of the cut locking element 108 from the second plate 104, illustrated as block 1608 and in FIG. 20. The ratchet wheel 120 may then be reinstalled in the first plate 102 by aligning the indicators 136 and 138, illustrated as block 1610 and in FIGS. 21 and 22. The ratchet wheel 120 may then be rotated to allow a new locking element 108 to be installed, illustrated as block 1612. The new locking element 108 may then be installed and the first and second plates 102 and 104 may be tightened to close the sternum as described above.

Another option is to remove the fasteners 150 and remove first and/or second plates 102 and 104 completely. If this option is used, the medial edges of the sternum may be brought into complete approximation using normal methods, including reduction instruments and or stainless steel wires. The first and second plates 102 and 104 may then be reinstalled with a new locking element 108 in accordance with the steps described above and illustrated in FIG. 9.

Additional embodiments including plates, ratcheting plates, ratcheting type island screws, and other embodiments are described below. Some devices and systems employ a plurality of different attachment devices used in combination, and are referred to as a "community" concept for the tether or tying arrangement. "Community" expresses the use of different anchoring concepts in a system.

Figure 26:
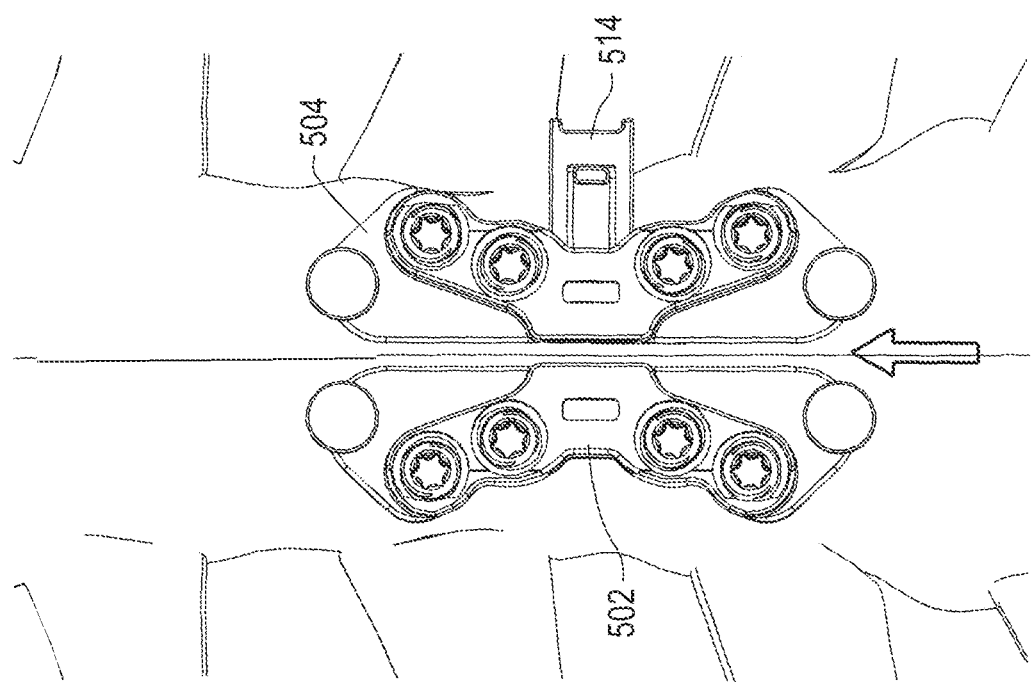

FIGS. 23-27 illustrate a fixation device 500 employing a locking tab. As illustrated, the device 500 includes first and second plates 502 and 504 that may be coupled to a bone in an opposed relationship, in a similar manner as described above. The plates 502 and 504 include fastener apertures 506 for receiving fasteners 508 for use in coupling the plates 502 and 504 to the bone. In a similar manner as described above, the plates 502 and 504 may be coupled to a sternum pre-resection, and the plates 502 and 504 may provide a space between the plates 502 and 504 for guiding a cutting tool (for example as illustrated in FIG. 26).

The plates 502 and 504 also include anchors 510 that are configure to receive a tether (not shown) to couple the plates 502 and 504 together and/or to one or more devices described herein having anchor points to close a divide in the bone. The plates 502 and 504 also include channels 512 (illustrated in FIG. 24) for receiving a tab 514. The tab 514 may include a deflectable prong 516 and the plates 502 and 504 may include corresponding prong receiving receptacles 518 configured to receive the prong 516 to tab 514 in the plates 502 and 504.

Figure 24:
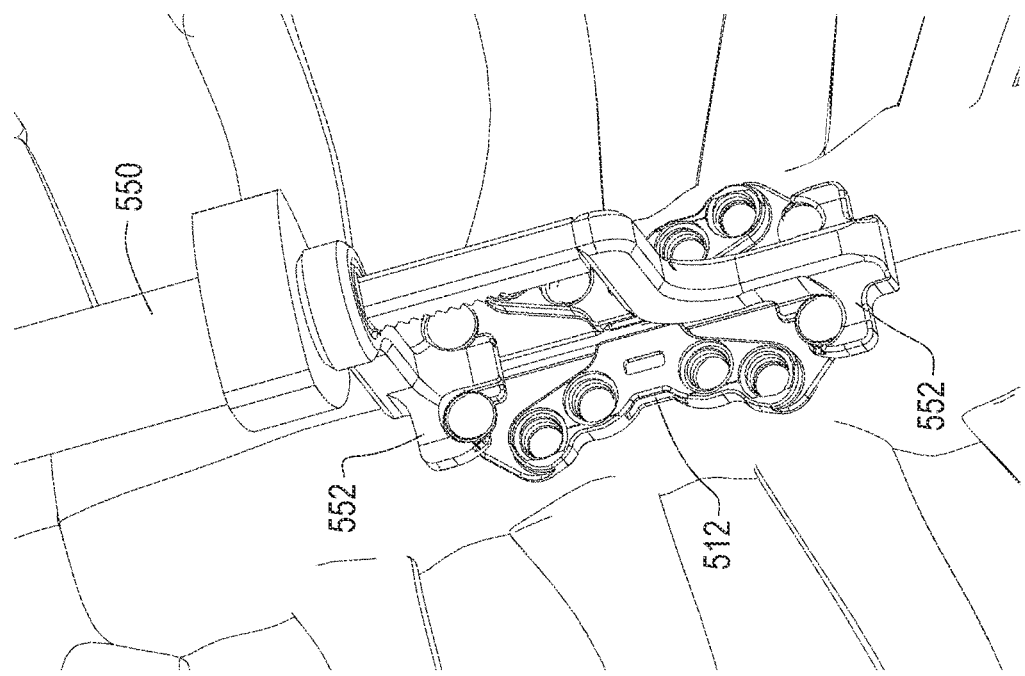
FIGS. 23-27 illustrate another implantable fixation device according to the disclosure.
Figure 23:
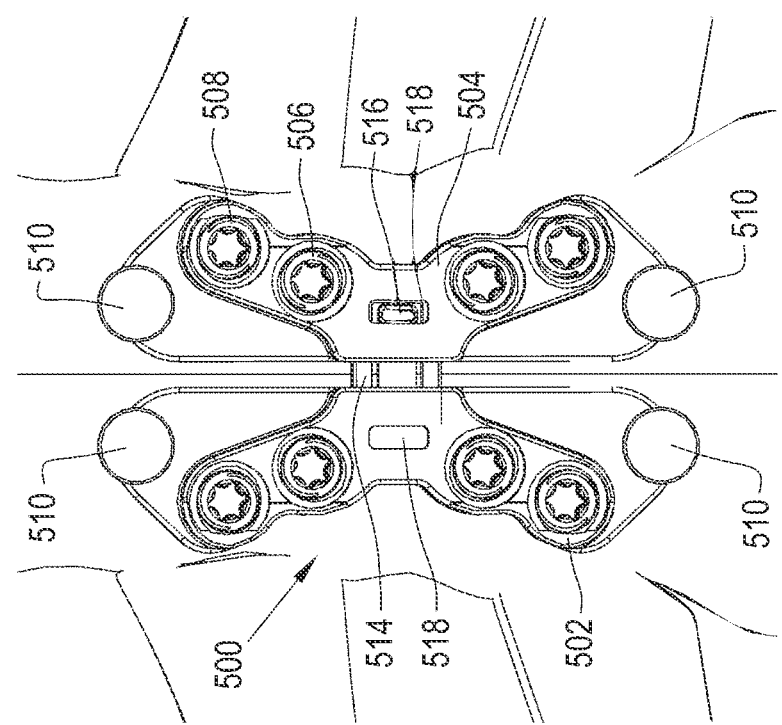
Figure 25:
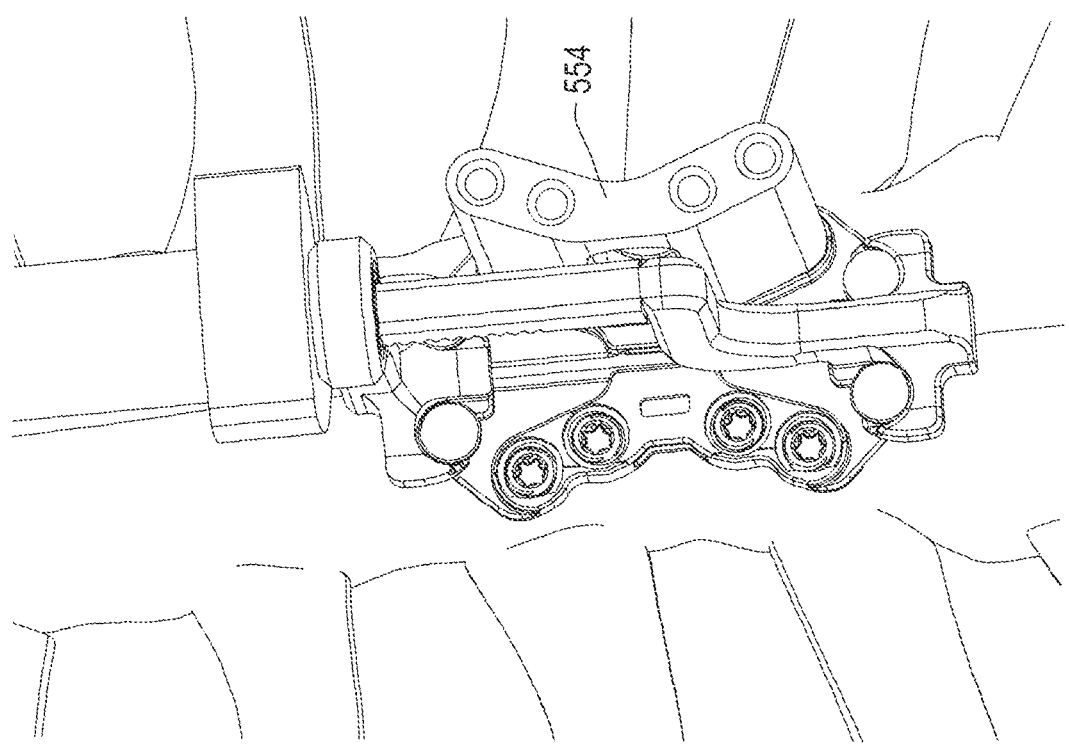
Figure 28:
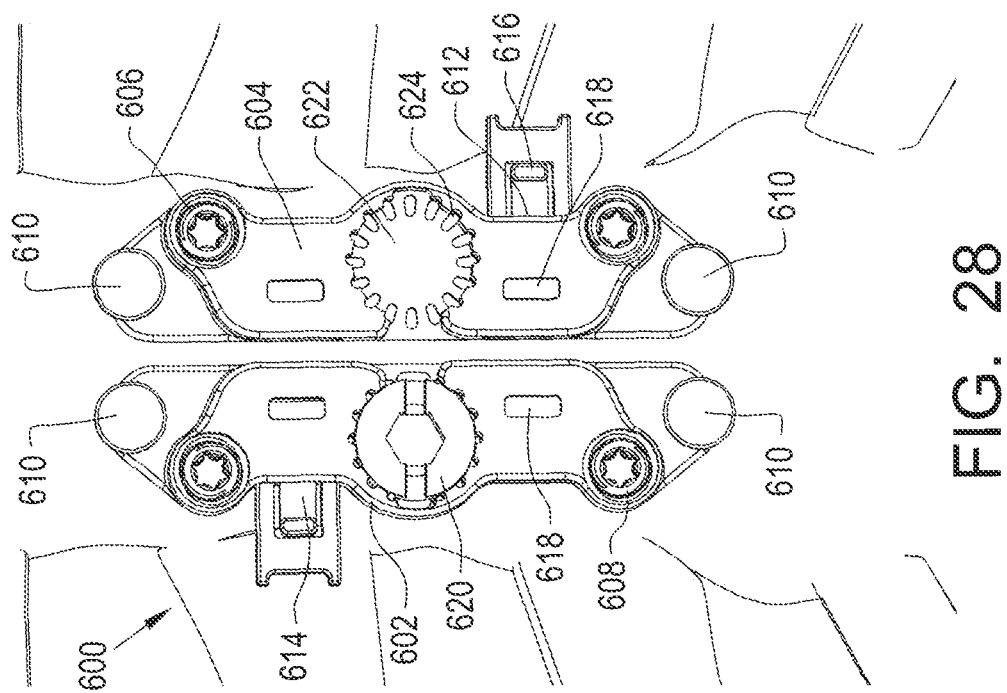
FIGS. 28-32 illustrate another implantable fixation device according to the disclosure.

Referring to FIGS. 23 and 24, the plates 502 and 504 may be installed using a tool having a handle 550 and gripping members 552. The gripping members 552 may grip the anchors 510 of the plates 502 and 504 and hold the plates 502 and 504 is a spaced relationship for coupling to the bone. Referring to FIG. 25, a fastener guide 554 may also be used to assist in driving fasteners 508 into the fastener apertures 506.

Figure 27:
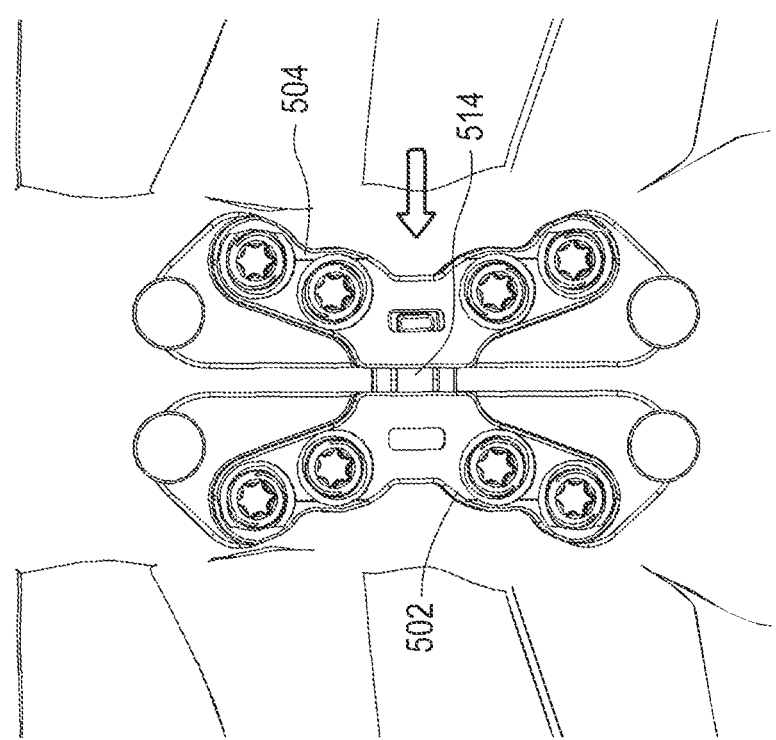

Once the plates are coupled to the bone, the bone may be cut using the plates 502 and 504 as a guide, as illustrated in FIG. 26. After a procedure is performed, the plates may also be used to align the cut bone portions and fix the bone portions back together. For example, as illustrated in FIG. 27, the plates 502 and 504 may be brought together closing the divide between the bone, and the tab 514 may be inserted into the channels 512. The deflectable prong 516 may then be seated into the prong receiving receptacle 518 to couple the plates 502 and 504 together.

Figure 30:
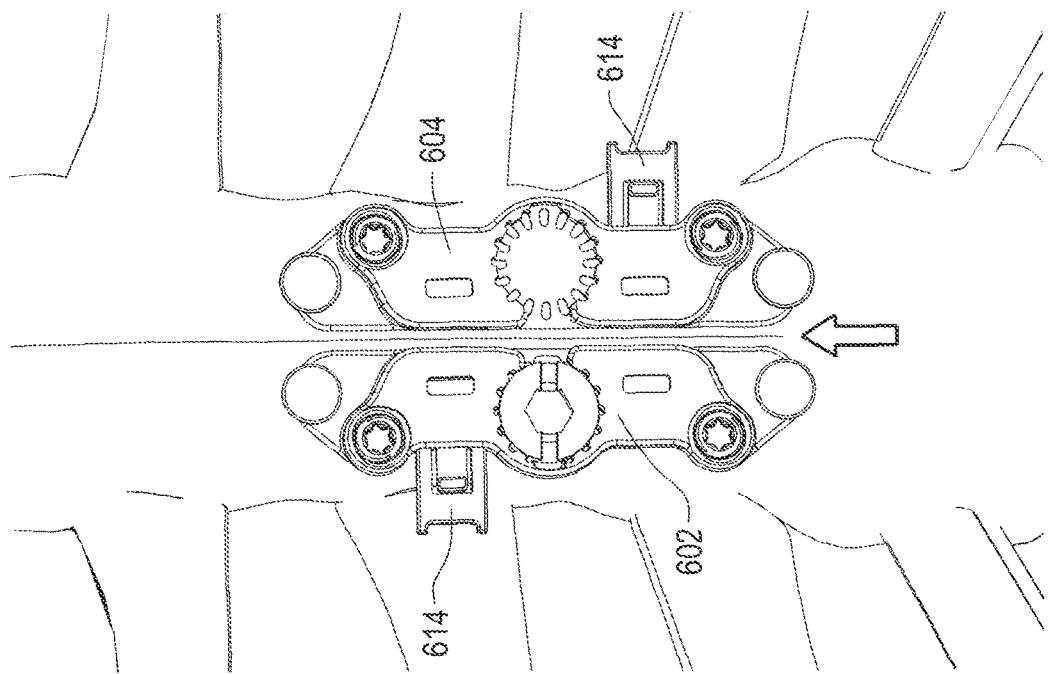

FIGS. 28-32 illustrate a fixation device 600 employing a locking tab and a ratchet mechanism. The device 600 is similar to that of device 500, except that it includes two tabs and a ratchet wheel in each of the plates. As illustrated, the device 600 includes first and second plates 602 and 604 that may be coupled to a bone in an opposed relationship, in a similar manner as described above. The plates 602 and 604 include fastener apertures 606 for receiving fasteners 608 for use in coupling the plates 602 and 604 to the bone. In a similar manner as described above, the plates 602 and 604 may be coupled to a sternum pre-resection, and the plates 602 and 604 may provide a space between the plates 602 and 604 for guiding a cutting tool (for example as illustrated in FIG. 30).

The plates 602 and 604 also include anchors 610 that are configure to receive a tether (not shown) to couple the plates 602 and 604 together and/or to one or more devices described herein having anchor points to close a divide in the bone. The plates 602 and 604 also include channels 612 for receiving tabs 614. The tabs 614 include a deflectable prong 616 and the plates 602 and 604 include corresponding prong receiving receptacles 618 configured to receive the prong 616 in the plates 602 and 604.

In this embodiment, the plates 602 and 604 also include a ratchet wheel 620 disposed in a ratchet recess 622 having ratchet teeth 624. The ratchet wheel 620 and recess 622 may be similar to the ratchet mechanism 106 described above. In this respect, the opposing ratchet wheels 620 in the opposing plates 602 and 604 may be used to draw the plates 602 and 604 together, using a tether or locking element, to close a divide in a bone.

Figure 29:
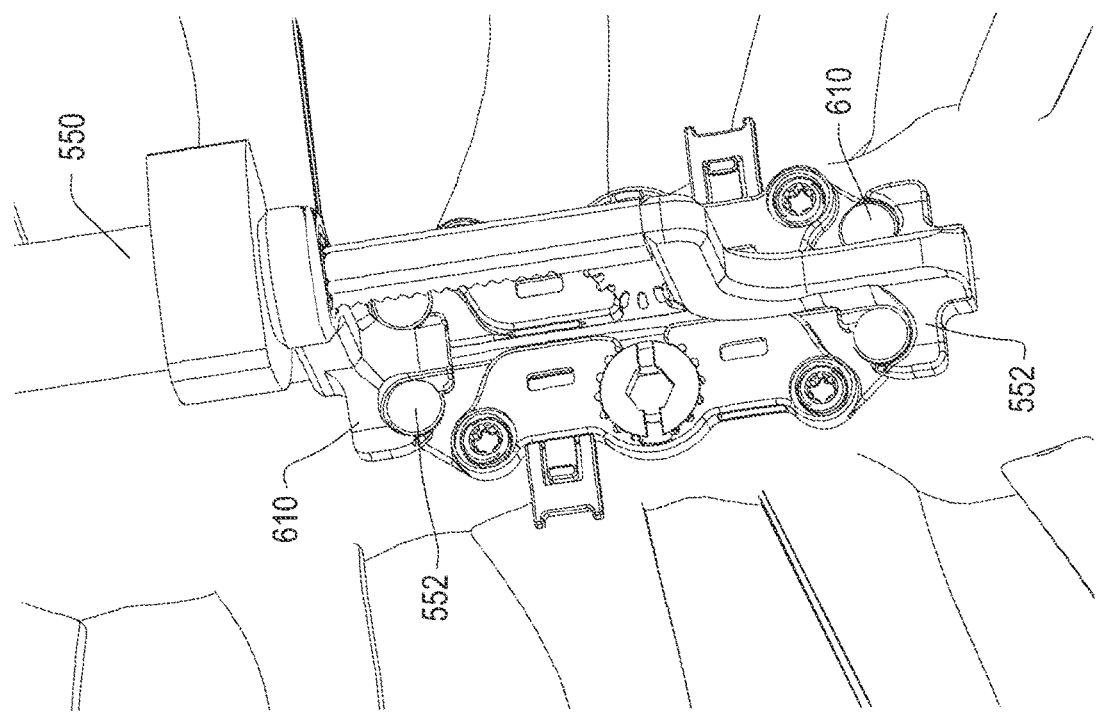

Referring to FIG. 29, the plates 602 and 604 may be installed using the tool having the handle 550 and gripping members 552. The gripping members 552 may grip the anchors 610 of the plates 602 and 604 and hold the plates 602 and 604 is a spaced relationship for coupling to the bone.

Figure 32:
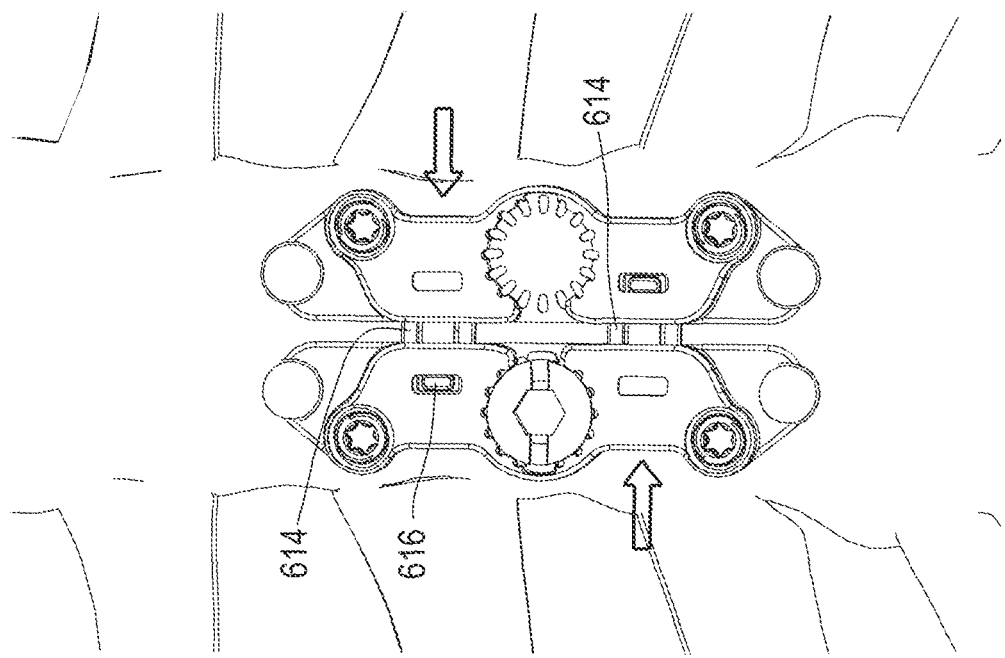
Figure 31:
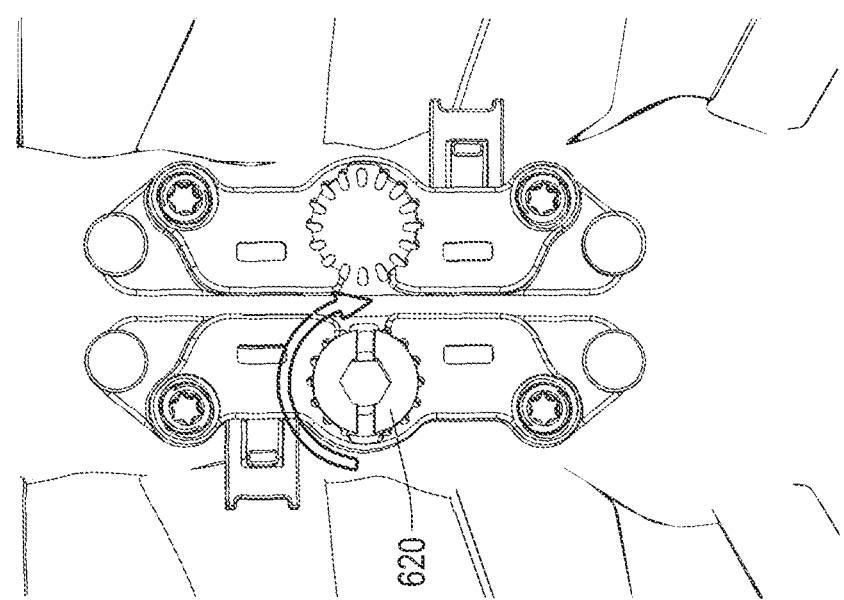

Once the plates are coupled to the bone, the bone may be cut using the plates 602 and 604 as a guide, as illustrated in FIG. 30. After a procedure is performed, the plates may also be used to align the cut bone portions and fix the bone portions back together. For example, as illustrated in FIGS. 31 and 32, the ratchet wheels 620 may be rotated to draw the plates 602 and 604 brought together, using a tether or locking element, closing the divide between the bone portions, and the tabs 614 may be inserted into the channels 612. The deflectable prongs 616 may then be seated into the prong receiving receptacles 618 to couple the plates 602 and 604 together.

Figure 33:
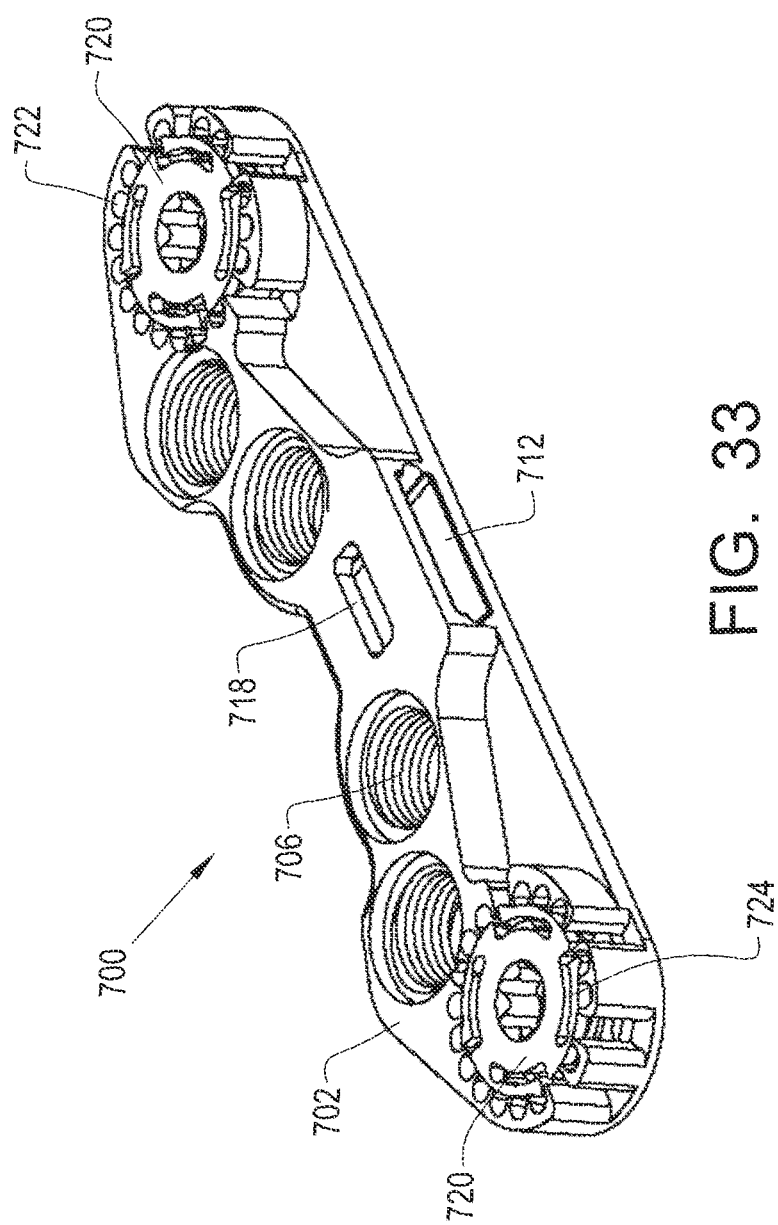
FIG. 33 illustrates another implantable fixation device according to the disclosure.
Figure 34:
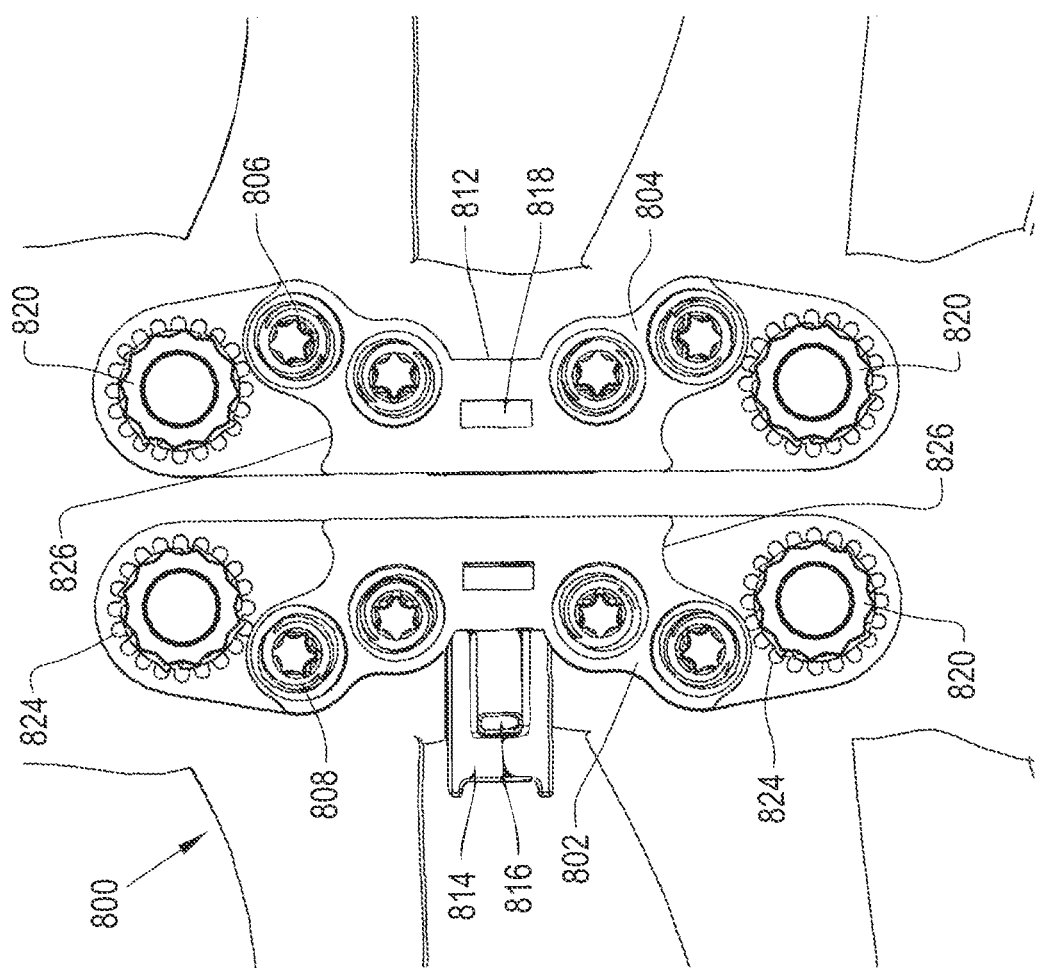
FIG. 34 illustrates another implantable fixation device according to the disclosure.

FIGS. 33-34 illustrate fixation devices 700 and 800 employing a locking tab and a ratchet mechanism. The devices 700 and 800 are similar to that of device 600, except that it includes two ratchet mechanisms and one tab in each plate. As illustrated in FIG. 33, the device 700 includes a plate 702 that may be places in opposed relationship with another plate 702 and coupled to a bone, in a similar manner as described above. The plate 700 includes fastener apertures 706 for receiving fasteners for use in coupling the plate 700 to the bone. In a similar manner as described above, two plates 700 may be coupled to a sternum pre-resection, and the plates 700 may provide a space between the plates 700 for guiding a cutting tool.

The plate 700 also includes a channel 712 for receiving a tab similar to that described above. The plate 700 includes a prong receiving receptacle 718 configured to receive a prong of the tab. In this embodiment, the plate 700 also includes two ratchet wheels 720 disposed in a ratchet recess 722 having ratchet teeth 724. The ratchet wheels 720 and recess 722 may be similar to the ratchet mechanism 106 described above. In this respect, opposing ratchet wheels 720 in the opposing plates 700 may be used to draw the plates 700 together, using a tether or locking element, to close a divide in a bone and/or may be used to tether the plates 700 to one or more other components described herein.

Referring to FIG. 34, the device 800 includes first and second plates 802 and 804 that may be coupled to a bone in an opposed relationship, in a similar manner as described above. The plates 802 and 804 include fastener apertures 806 for receiving fasteners 808 for use in coupling the plates 802 and 804 to the bone. In a similar manner as described above, the plates 802 and 804 may be coupled to a sternum pre-resection, and the plates 802 and 804 may provide a space between the plates 802 and 804 for guiding a cutting tool.

The plates 802 and 804 also include channels 812 for receiving a tab 814. The tab 814 includes a deflectable prong 816 and the plates 802 and 804 include corresponding prong receiving receptacles 818 configured to receive the prong 816 in the plates 802 and 804. In this embodiment, the plates 802 and 804 also include two ratchet wheels 820 disposed in a ratchet recess 822 having ratchet teeth 824. The ratchet wheels and recesses may be similar to the ratchet mechanism 106 described above. In this respect, opposing ratchet wheels 820 in the opposing plates 802 and 804 may be used to draw the plates 802 and 804 together, using a tether or locking element, to close a divide in a bone and/or may be used to tether the plates 802 and 804 to one or more other components described herein.

Once the plates are coupled to the bone, the bone may be cut using the plates 802 and 804 as a guide. After a procedure is performed, the plates may also be used to align the cut bone portions and fix the bone portions back together. For example, the ratchet wheels 820 may be rotated to draw the plates 802 and 804 together closing the divide between the bone portions, and the tab 814 may be inserted into the channels 812. The deflectable prongs 816 may then be seated into the prong receiving receptacles 818 to couple the plates 802 and 804 together.

Figure 35:
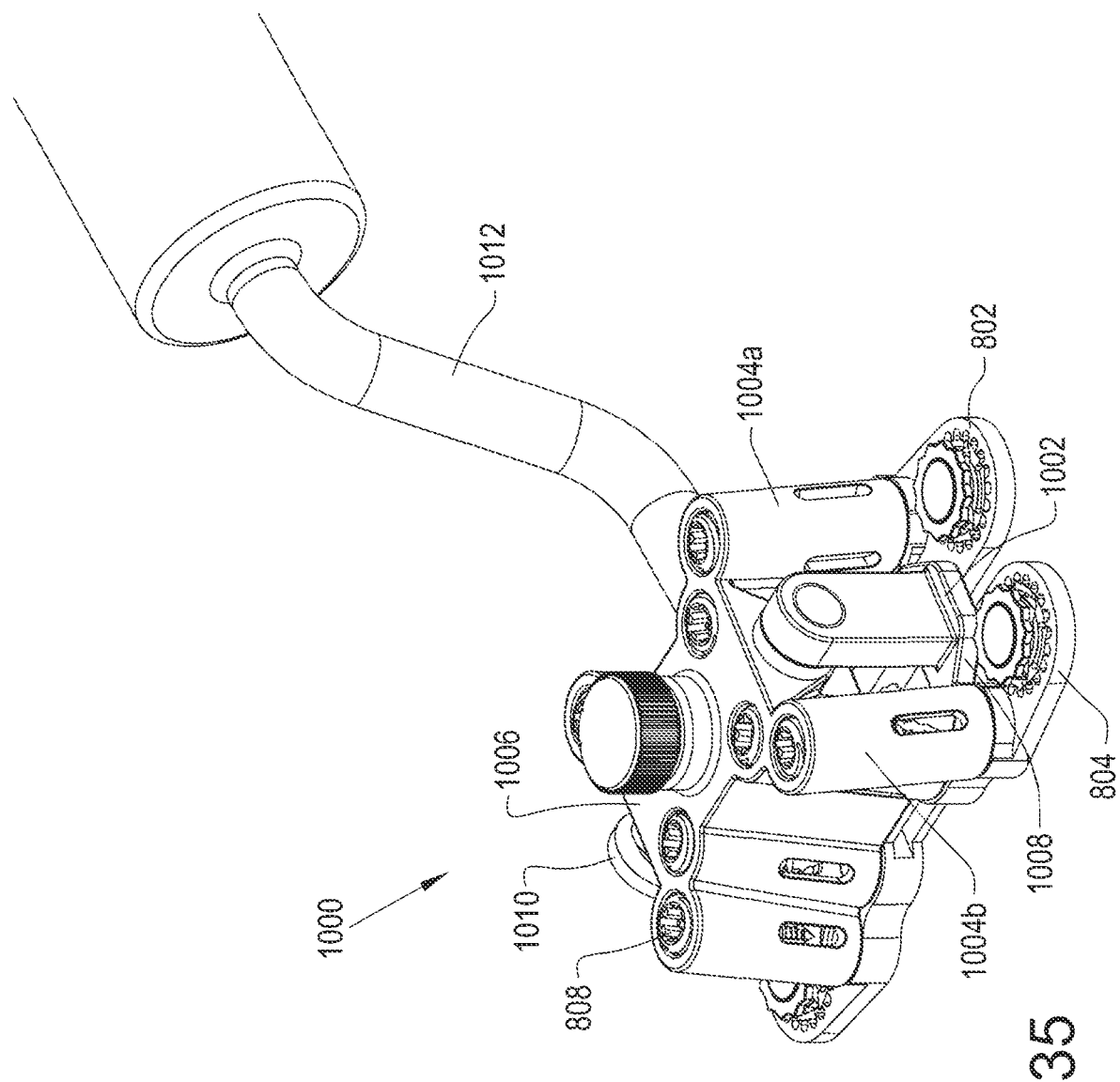
FIG. 35 illustrates another fixation device positioning holder according to the disclosure.

Referring to FIGS. 34 and 35, the plates 802 and 804 may be installed using a positioning holder 1000, similar to the position holder 200 described above. For example, the positioning holder 1000 includes a body 1002 including a first set of fastener guides 1004a and a second set of fastener guides 1004b on opposite sides of the body 1002, a compression attachment mechanism 1006, and attachment feet 1008.

The first and second sets of fastener guides 1004a and 1004b provide a housing to guide fasteners 808 for insertion into the threaded fastener apertures 806 of the plates 802 and 804. The compression attachment mechanism 1006 may include a spring loaded mechanism that when compressed causes a distance between opposing ones of the attachment feet 1008 to increase and when released causes the distance between the attachment feet 1008 to decrease and mate with corresponding recesses 826 in the plates 802 and 804.

The attachment feet 1008 serve to hold the plates 802 and 804 in the positioning holder 1000 at a predetermined distance from each other. The compression attachment mechanism 1006 allows for the positioning holder 1000 to be coupled to and uncoupled from the plates 802 and 804 quickly and easily, simply by compressing the spring loaded mechanism. For example, when gripping portion 1010 is compressed, the distance between the opposing feet 1008 is increased. This allows the first and second plates 802 and 804 to be placed in the positioning holder 100, and when the compression force applied to the gripping portion 1010 is released, the feet 1008 mate with the recesses 826.

The positioning holder 1000 may include a handle 1012 for ease of assembly of elements and placement of the plates. The handle 1012 may have an ergonomic design for comfort and control of the positioning holder 1000. The handle 1012 may also be angled to accommodate soft tissues and various surgical approaches. The positioning holder 1000 may be used to assist in placing and holding the positioning holder 1000 and the plates 802 and 804 in a proper orientation as the fasteners 808 are driven to couple the plates 802 and 804 to a bone or other portion of a patient's body.

When closing a divide in a bone using the devices 700 and 800, the rotation of the ratchet wheels can be timed in sequence for more tension or offset to any number of positions to refine the increments of rotation as the ratchet wheels are rotated.

Figure 37:
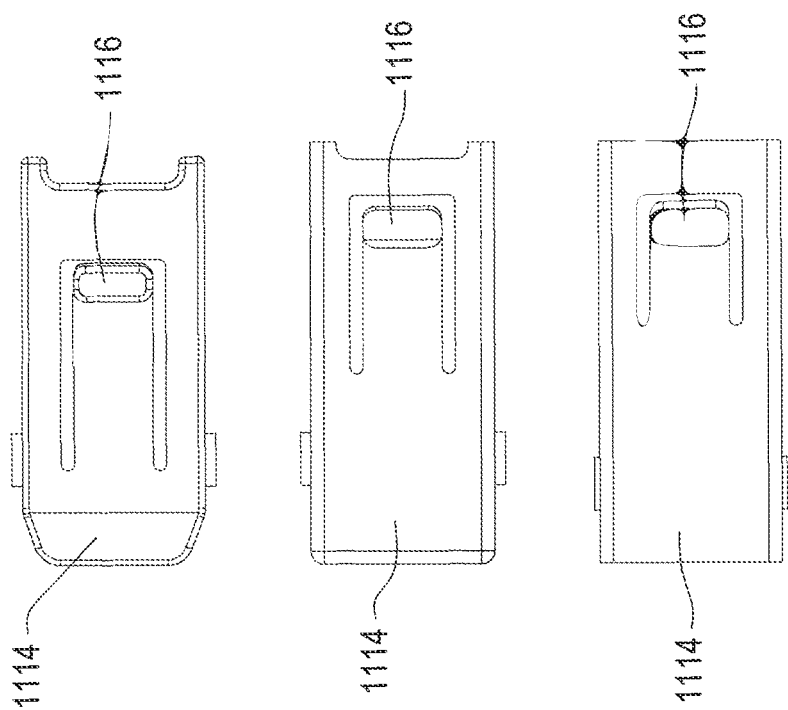
FIGS. 36 and 37 illustrate another implantable fixation device according to the disclosure.
Figure 36:
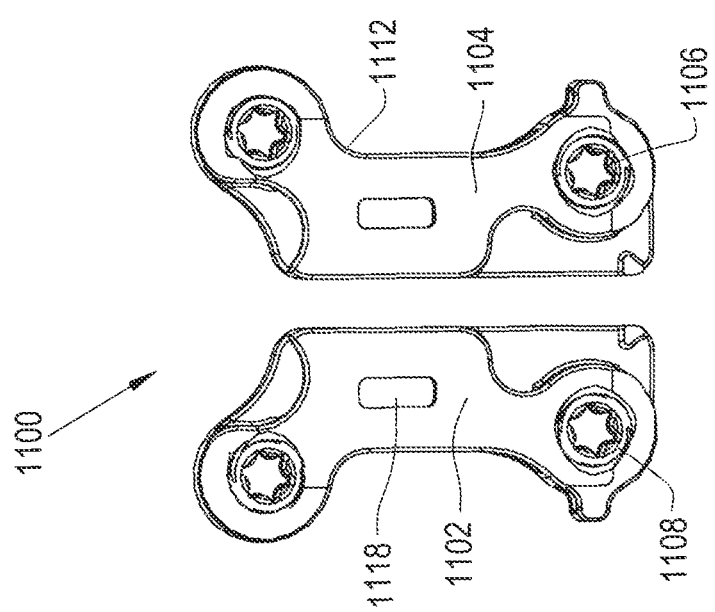

FIGS. 36-37 illustrate another fixation device 1100 employing a locking tab. As illustrated, the device 100 includes first and second plates 1102 and 1104 that may be coupled to a bone in an opposed relationship, in a similar manner as described above. The plates 1102 and 1104 include fastener apertures 1106 for receiving fasteners 1108 for use in coupling the plates 1102 and 1104 to the bone. In a similar manner as described above, the plates 1102 and 1104 may be coupled to a sternum pre-resection, and the plates 1102 and 1104 may provide a space between the plates 1102 and 1104 for guiding a cutting tool.

The plates 1102 and 1104 also include channels 1112 for receiving a tab 1114. The tab 1114 may include a deflectable prong 1116 and the plates 1102 and 1104 may include corresponding prong receiving receptacles 1118 configured to receive the prong 1116. Once the plates are coupled to the bone, the bone may be cut using the plates 1102 and 1104 as a guide. After a procedure is performed, the plates may also be used to align the cut bone portions and fix the bone portions back together. For example, the plates 1102 and 1104 may be brought together closing the divide between the bone, and the tab 1114 may be inserted into the channels 1112. The deflectable prong 1116 may then be seated into the prong receiving receptacle 1118 to couple the plates 1102 and 1104 together.

Figure 38:
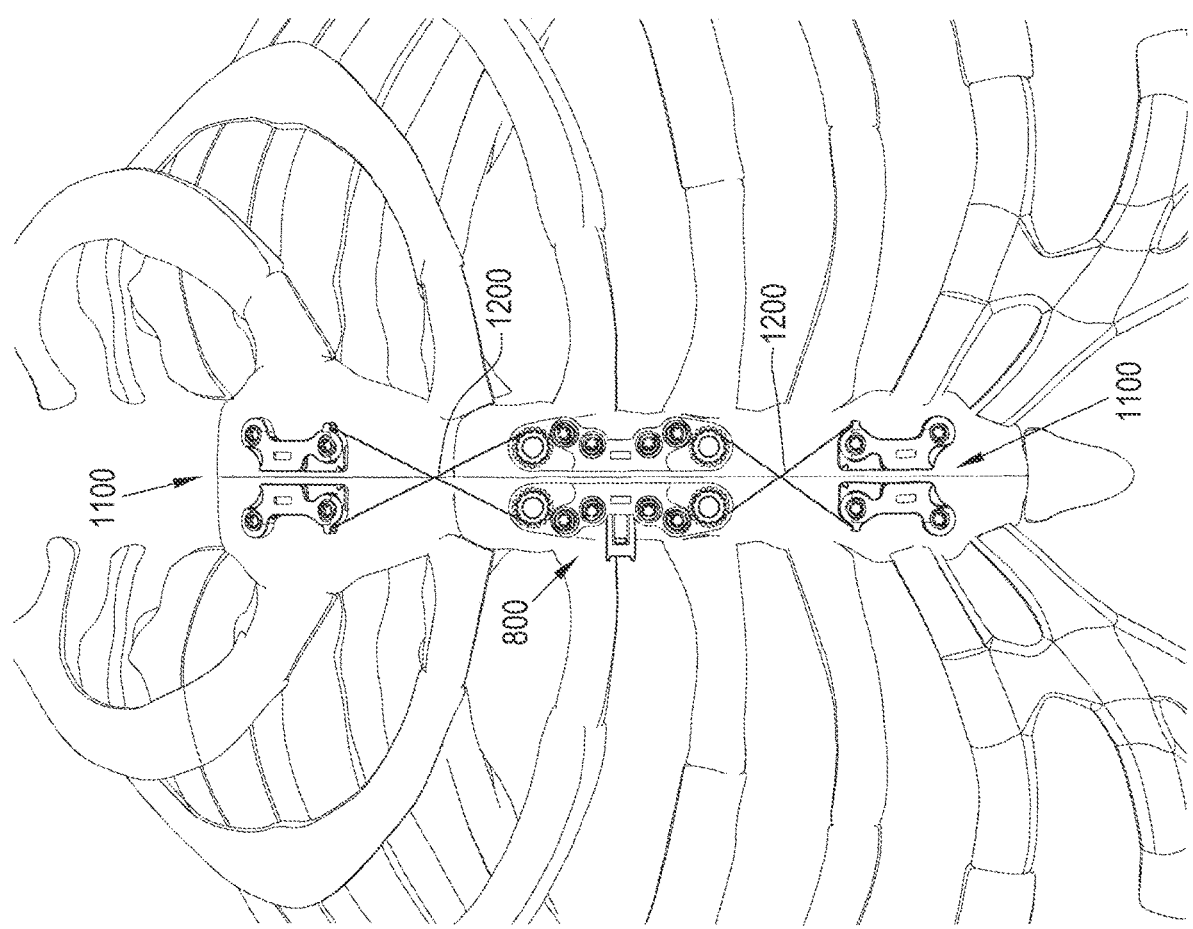
FIG. 38 illustrates the implantable fixation devices of FIGS. 34 and 36-37 installed according to the disclosure.
Figure 39:
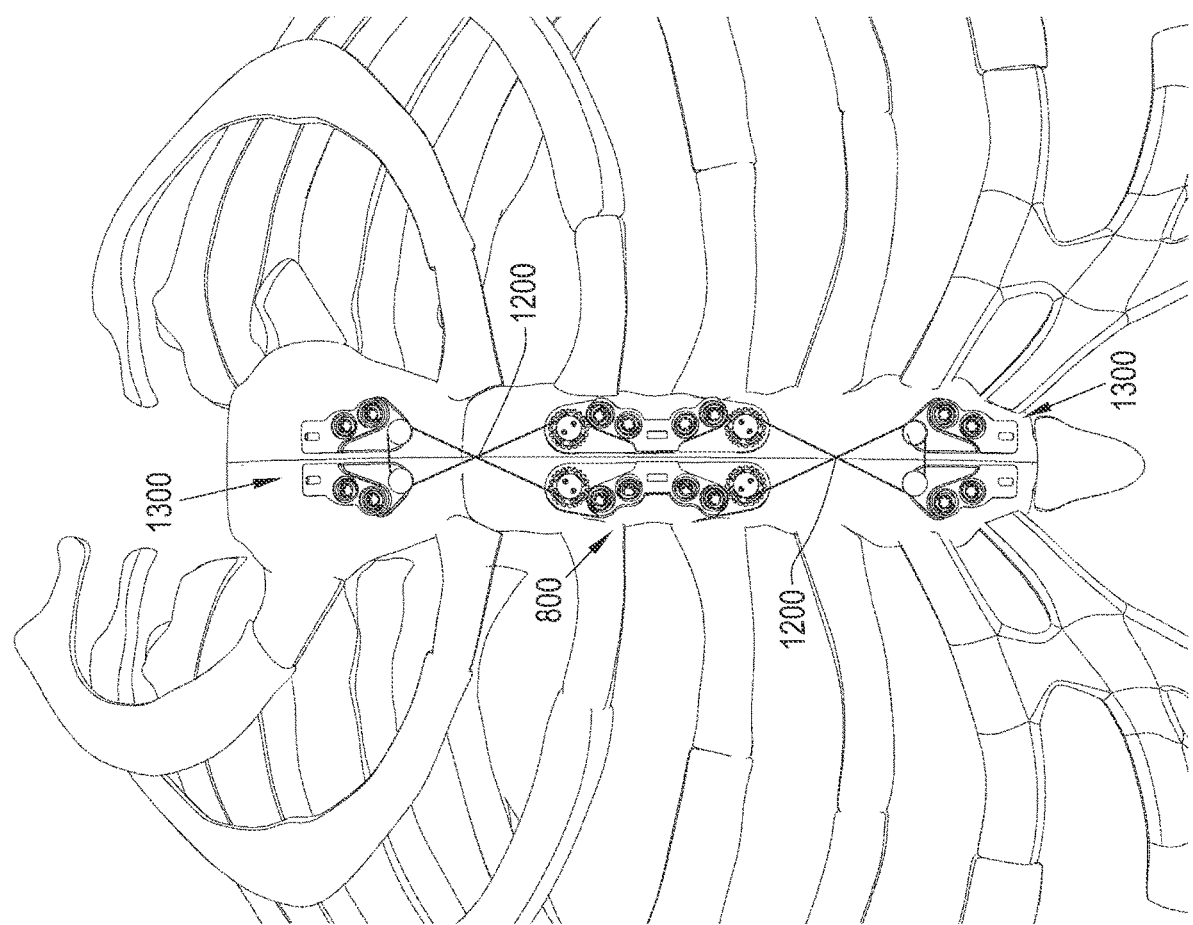
FIG. 39 illustrates the implantable fixation devices of FIGS. 34 and 36-37 installed according to the disclosure.

FIGS. 38-39 illustrate systems incorporating the fixation device 800 and 1100, and a similar fixation device 1300 to the device 1100, but having a different shape and anchors. As illustrated the devices 800 and 1100/1300 may be placed longitudinally along a sternum and tethered together using tether 1200 to close the sternum post-resection.

Figure 41:
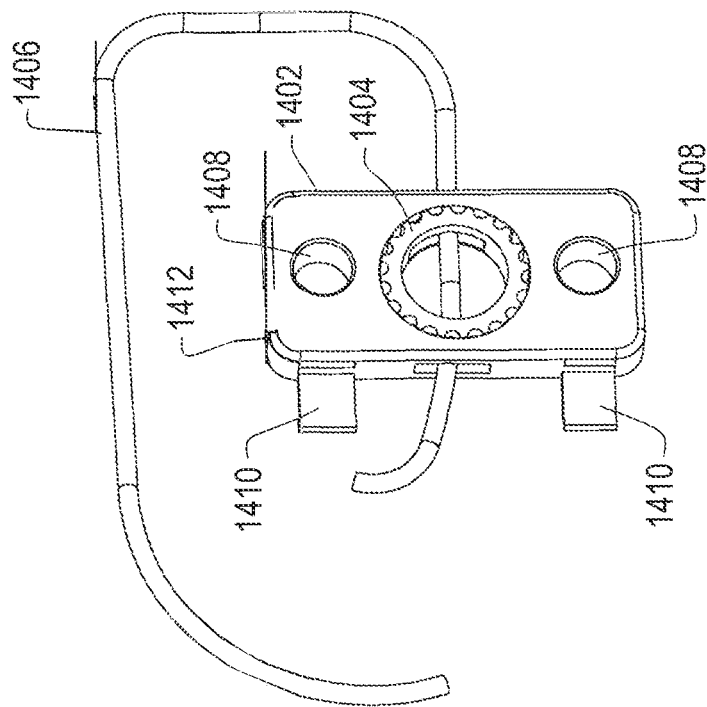
FIGS. 40-41 illustrate another implantable fixation device according to the disclosure.
Figure 40:
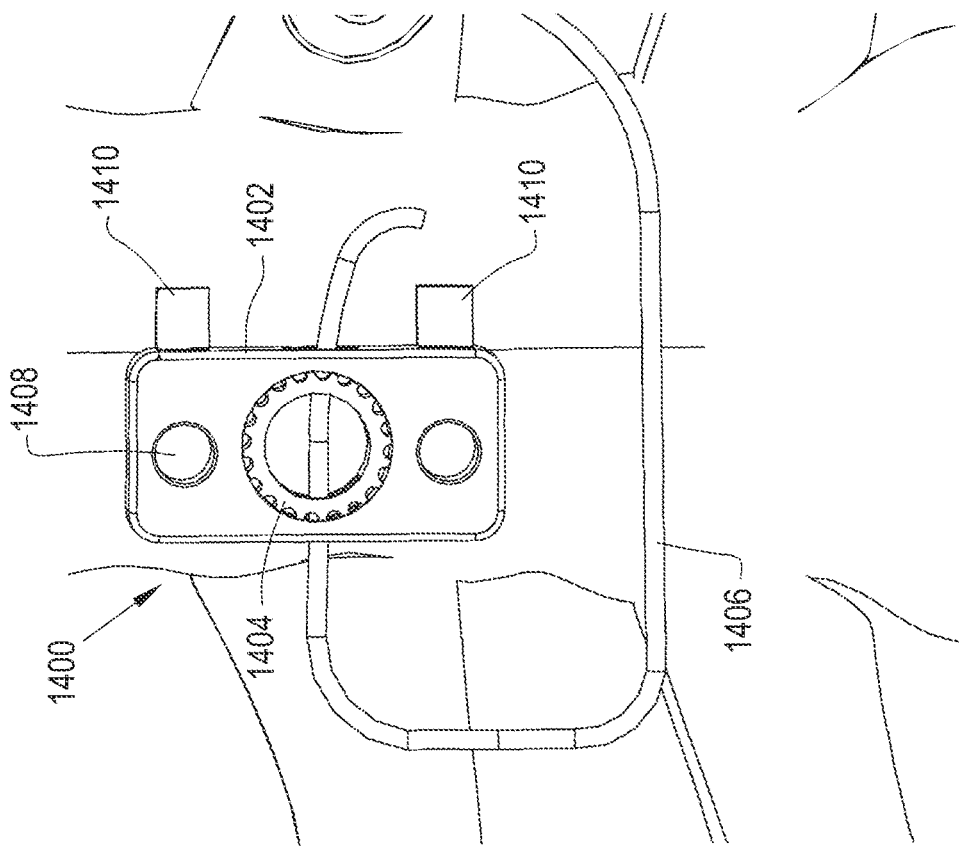

FIGS. 40 and 41 disclose a fixation device 1400 using a ratcheting device as part of the mechanism to close the sternotomy. This system employs a base plate 1402 having a rotating ratchet 1404 therein. The ratchet 1404 only rotates in one direction (clockwise or counterclockwise), and a release button (not shown) could be employed which would allow release of tension for surgical technique or for emergency re-entry. In this system, a number of island screws may be employed, with a tether 1406 woven between island screws and one or preferably more of the ratcheting devices 1404, the ratchet piece 1404 is rotated or wound to pull in the tether 1406, and thereby pull the sternal portions together. Note the fastener apertures 1408 in the plate 1402 for fixation to a bone.

In a variation of the foregoing, or in addition, cooperating opposed ratcheting devices 1404 could be used on either side of the sternum resection. Tabs or flanges 1410 extend from one side of the device, and would overlap and be received in slots 1412 of the opposing device 1400.

Figure 42:
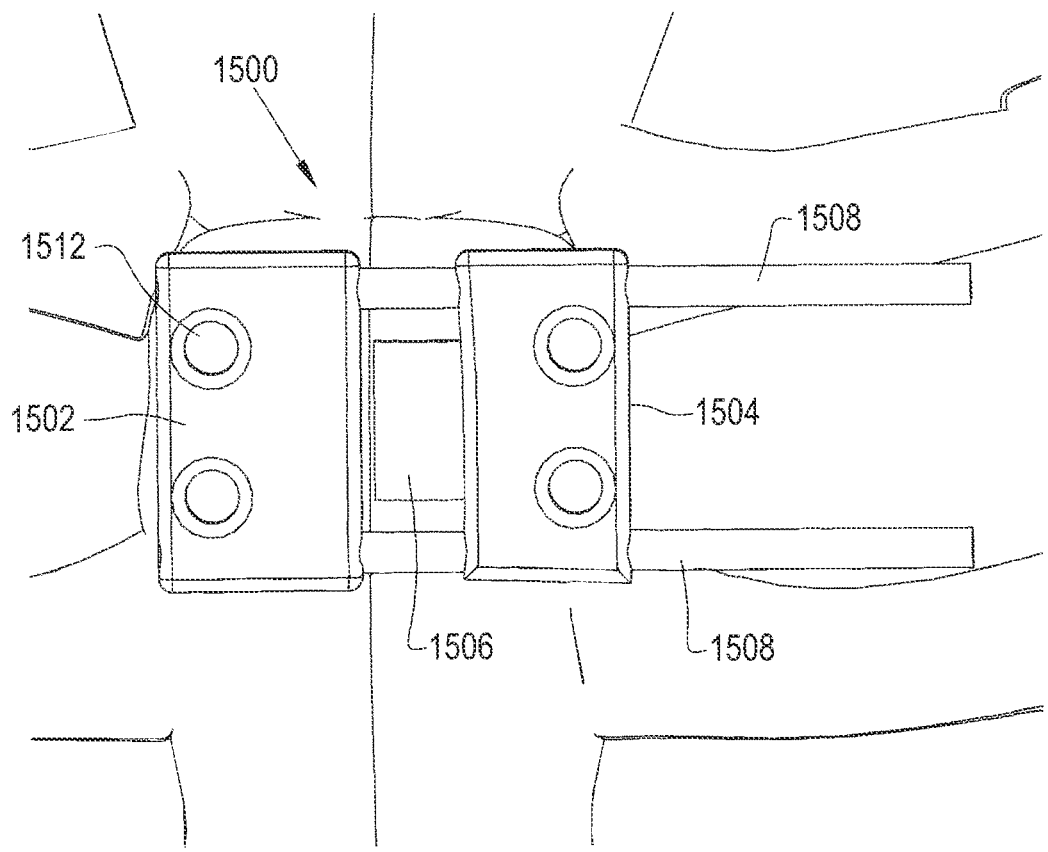
FIGS. 42-43 illustrate another implantable fixation device according to the disclosure.
Figure 43:
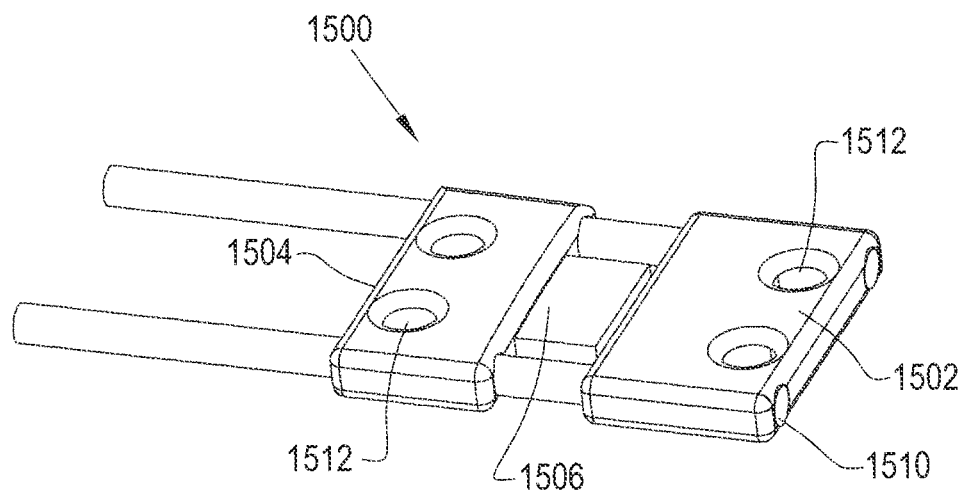

FIGS. 42 and 43, illustrates a system that employs a number of "splitlock" fixation devices 1500 located along the sternum. There are left 1502 and right 1504 tab or plate members which are fixed to opposed sternum portions, and a middle tab member 1506 that extends between the left and right members 1502 and 1504. The middle tab member 1506 may be formed on one of the left or right members 1502 or 1504, and fit in a channel in the other tab member 1502 or 1504, for one example, thereby fixing the integrated module 1500 against transverse and shear forces.

The female tab member could be fixed pre-resection. The other or male tab member is then located and fixed post-resection, with the cable or cables 1508 inserted through the channels 1510 provided internally to the tab members. The three tab members may be designed to be initially pinched together. Fasteners inserted through the tabs via fastener apertures 1512 then lock the cables 1508 in position. In the event of an emergency reopening of the chest cavity, the cables 1508 can be readily cut.

Figure 44:
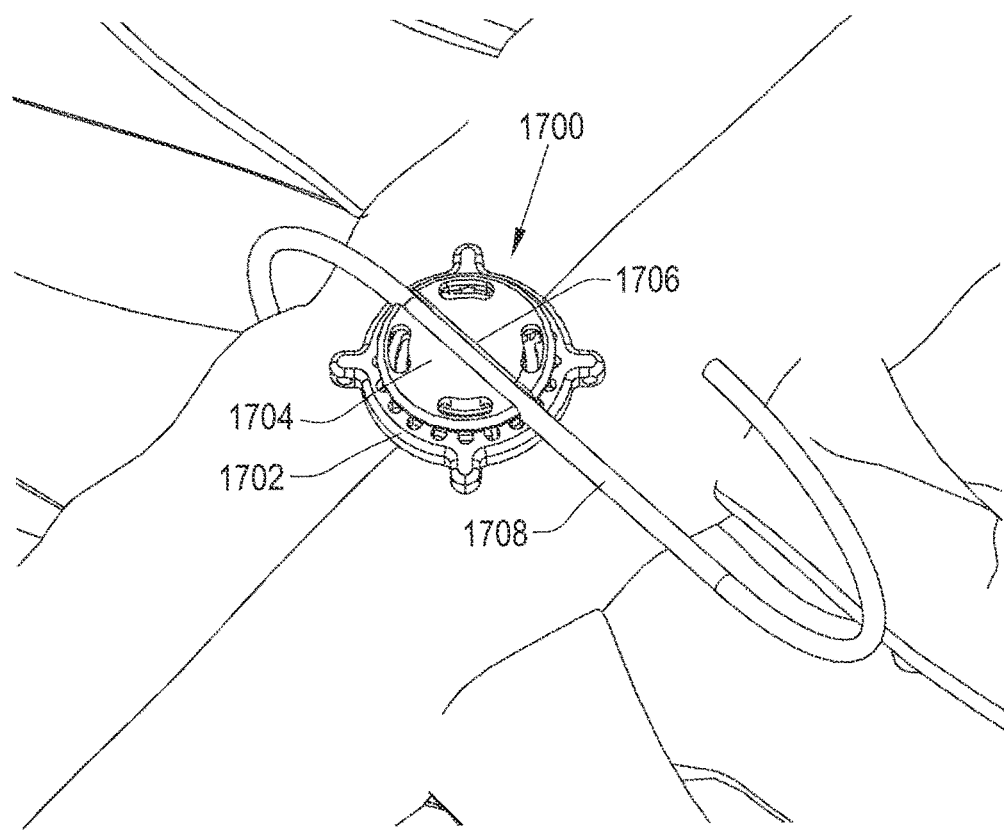
FIGS. 44-46 illustrate island type ratcheting fixation devices according to the disclosure.
Figure 45:
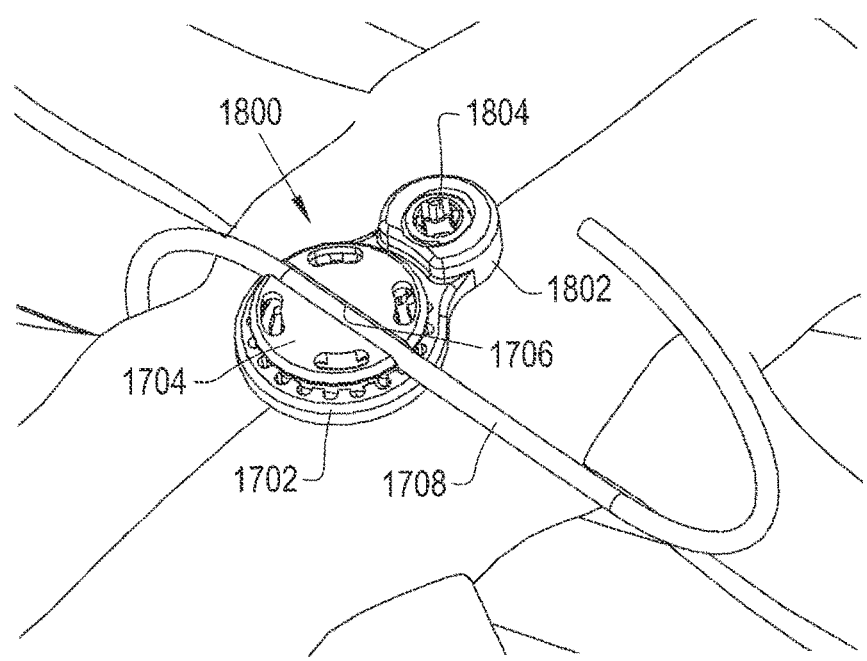
Figure 46:
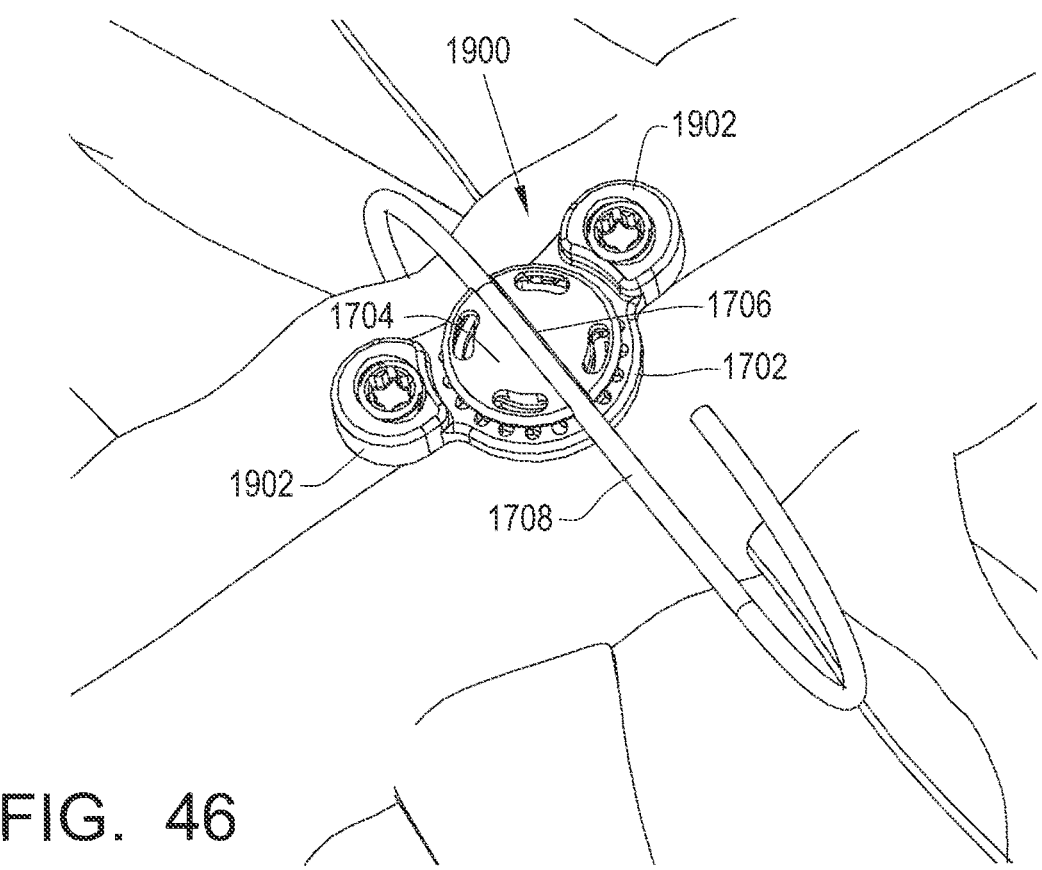

FIGS. 44-46 illustrate island type ratchet mechanism. As illustrated in FIG. 44, an island type ratchet mechanism 1700 is illustrated that includes a base 1702 including a ratchet recess with ratchet teeth. A ratchet wheel 1704 is disposed in the base 1702. The base 1702 and ratchet wheel 1704 may be similar to the ratchet mechanism 106 described above. In this embodiment, a tether or cable 1708 can be laid across an open slot 1706 in a top portion of the ratchet wheel 1704. Alternatively, the cable 1708 could go through a hole or other connection methods may be used. The ratchet wheel 1704 may be rotated to tighten the cable 1708.

Referring to FIG. 45, a fastener arm 1802 may be incorporated into the island type ratchet mechanism 1700 forming island type ratchet mechanism 1800. The fastener arm 1802 may receive a fastener 1804 to couple the island type ratchet mechanism 1800 to a bone or other body part. Similarly, referring to FIG. 46, two fastener arms 1902 may be incorporated into the island type ratchet mechanism 1700 forming island type ratchet mechanism 1900.

It should be appreciated that the cable 1708 may be tethered to other embodiments disclosed herein to close a divide in a bone. All of these concepts can be applied all over the body on boney tissue as well as soft tissue. For example, these concepts could be used to attach tendons and ligaments to each other. They can connect soft tissue to boney tissue. A greater trochanter attachment would be an example. A rotator cuff repair or an ACL repair is also feasible, craniomaxillo facial applications, dental, spine, trauma, orthopaedics, sports medicine, etc. The island type ratchet mechanisms could be used in spine surgeries with systems to create more or reduce lordosis or kyphosis. This could also be used with external fixators to be a quick easy method to increase the spanner.

Figure 47:
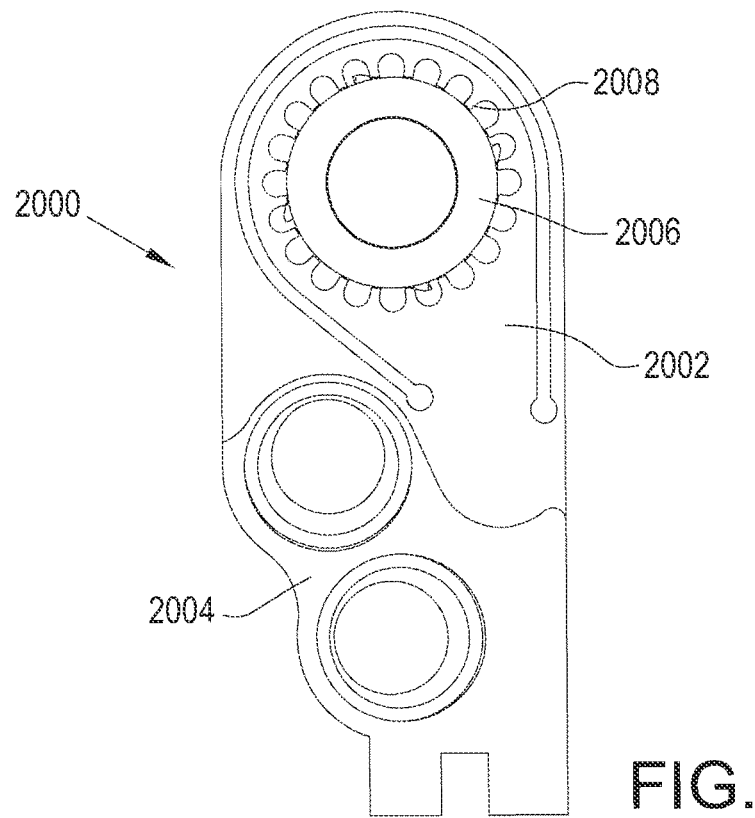
FIG. 47 illustrates another implantable fixation device according to the disclosure.

FIG. 47 illustrates a ratchet type plate 2000 with a flexor 2002. The flexor 2002 forms an end of the plate 2004 and is an elastic element that is capable of distributing loads upon a cough, fall, breathing, or other activities. This can reduce the overall stress on all components. By staying in an elastic region, it accommodates the fracture or osteotomy site for bone healing. As illustrated, a ratchet wheel 2006 and corresponding ratchet teeth 2008 are disposed on the flexor 2002. The flexor concept may be incorporated into any of the embodiments herein to allow for greater elasticity in the plates.

Figure 48:
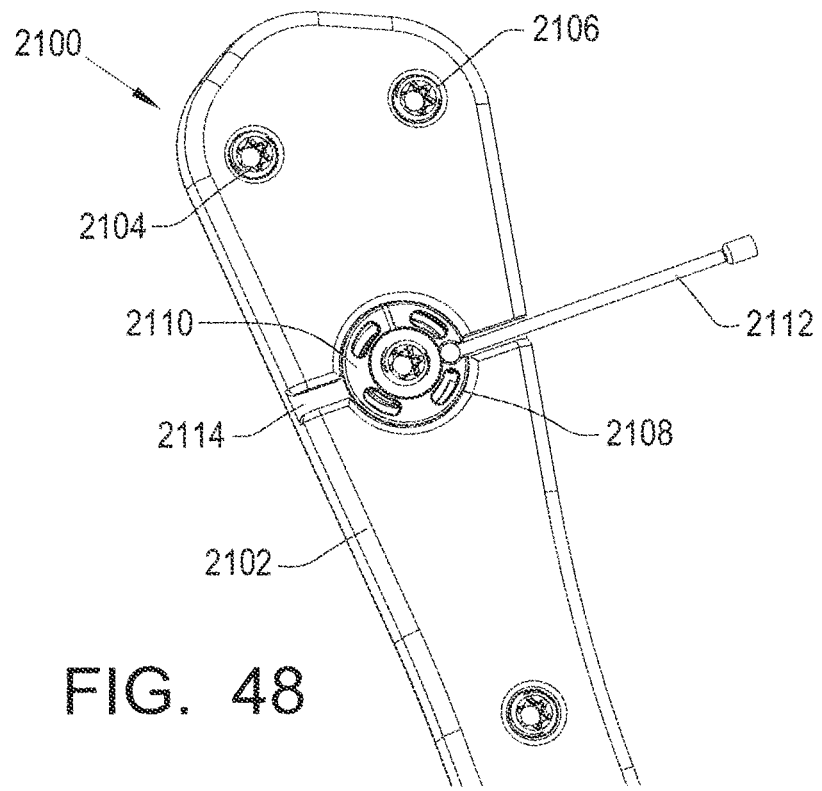
FIGS. 48-49 illustrate another implantable fixation device according to the disclosure.
Figure 49:
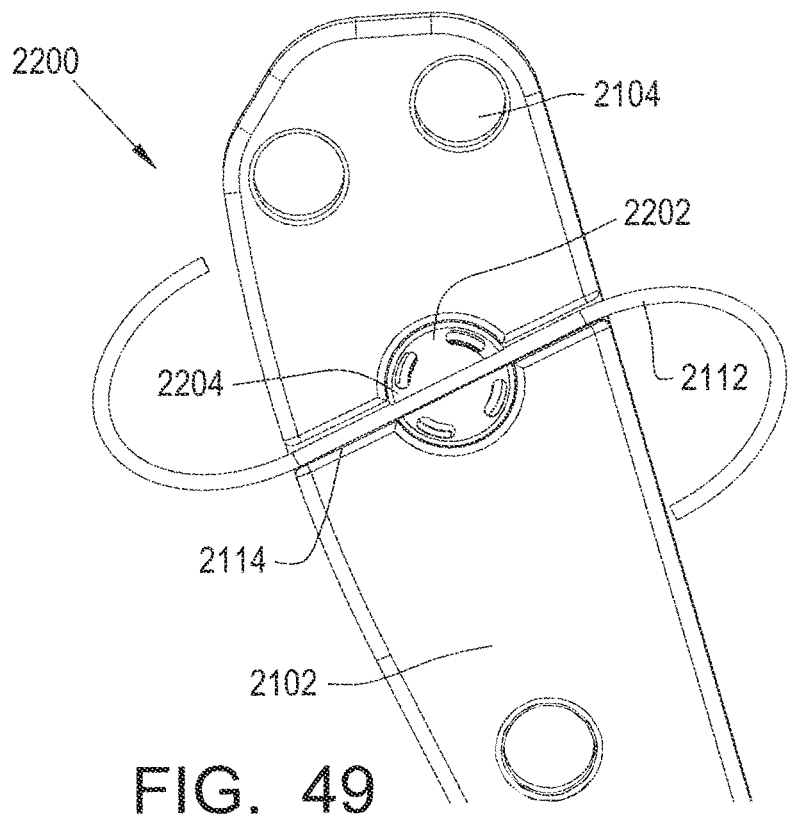

FIGS. 48 and 49 illustrate fixation devices including a ratchet mechanism. These designs have a feature to receive a ratchet wheel and allow a cable or other element to be attached around or to it. The cable can go around a body part and attach to itself or there can be fixed ends for attaching to other tissues or components.

Referring to FIG. 48, the device 2100 includes a plate 2102 including fastener apertures 1204 for receiving fasteners 2106 to couple the plate 2102 to a bone. The plate 2102 includes a ratchet recess 2108 with ratchet teeth. A ratchet wheel 2110 is disposed in the ratchet recess 2108. The ratchet recess 2108 and ratchet wheel 2110 may be similar to the ratchet mechanism 106 described above. In this embodiment, a locking element or tether or cable 2112 can be seated in a corresponding locking element capture receptacle. Referring to FIG. 49, the ratchet wheel may alternatively include an open slot 2204 a top portion forming ratchet wheel 2202 in which the cable 2112 may be laid. The plates 2100 and 2200 may also include a slot 2114 for receiving the cable 2112. The cable 2112 may be coupled to another embodiment disclosed herein to close a divide in a bone and/or provide a tensioning element for another application.

FIG. 50 illustrated a crimp cable lock type fixation device 2300. As illustrated, the device 2300 is similar to that of the device 100 described above, but includes cable crimp locking mechanisms instead of the ratchet mechanism. For example, the device includes plates 2302 and 2304. Each of the plates include crimp locking mechanisms 2306 and corresponding channels that receive the cable 2308 and couple the plates 2302 and 2304 to one another. It should be appreciated that the cable 2308 may also be tethered to other embodiments and anchors disclosed herein. The plates 2302 and 2304 may be installed before and after the sternotomy.

Figure 52:
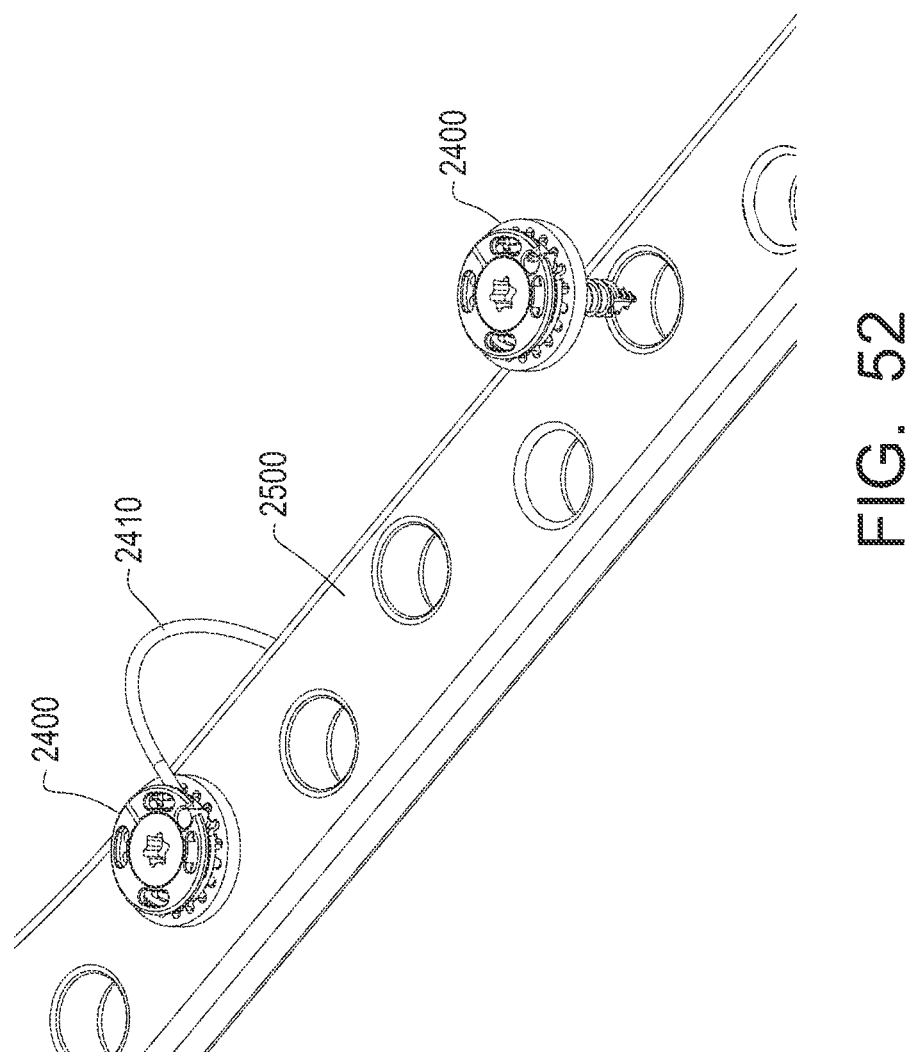
FIGS. 51-52 illustrate another island type ratcheting fixation devices according to the disclosure.
Figure 51:
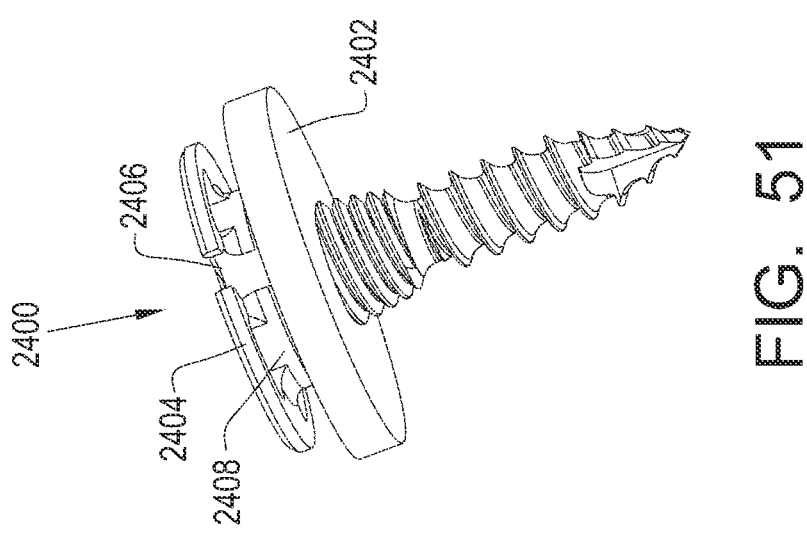

FIGS. 51 and 52 illustrate a ratchet screw 2400 with a trauma plate 2500. The ratchet screw 2400 includes a base 2402 including threads, and a ratchet wheel 2404 coupled to the base 2402. The ratchet wheel 2404 includes a cable capture receptacle 2406 to receive and hold an end of a cable 2410. The ratchet wheel 2404 also includes a groove 2408 into which the cable may be coiled to tighten the cable 2410. The ratchet mechanism in the ratchet screw 2400 may be similar to the ratchet mechanisms described above, and may be used in a multiple piece system or attached directly. The ratchet screw 2400 can be mated with any other type of trauma plate of any companies design or designed to mate with a particular plate to recess the screw further. The same approach applies that it can be locked and removed to allow for removal.

Figure 53:
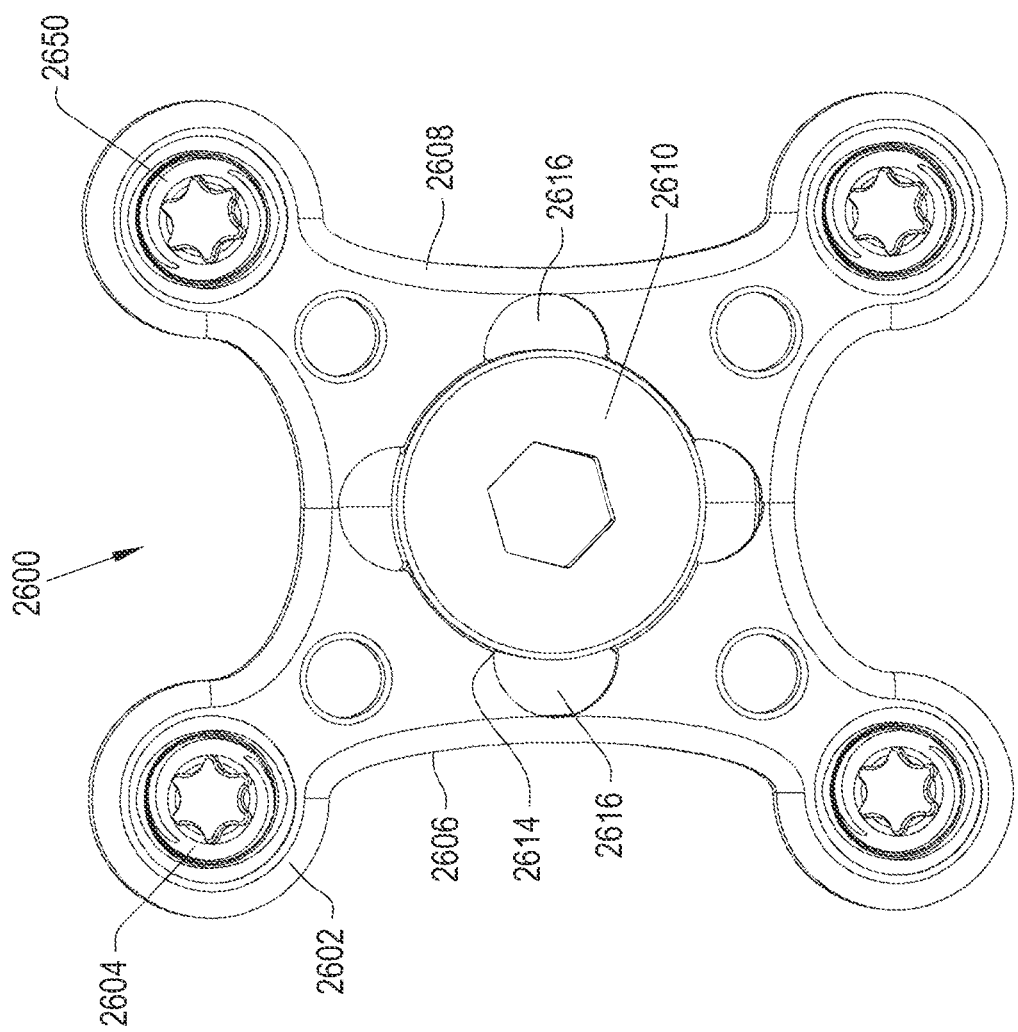
FIG. 53 illustrates another implantable fixation device according to the disclosure.

FIGS. 53-60 illustrate systems referred to as "spyderlock" arrangements. Referring to FIG. 53, the device 2600 includes four arms 2602 to the module, having fastener apertures 2604 at the end of the arms 2602 to receive fasteners 2650. Additional arms could be added in which to provide additional fixation options or stability. Two arms 2602 are on each plate 2606, 2608 of the module 2600, on either side of the sternum portions. There is a central rotatable piece 2610 which fits within a central well between the two plates 2606 and 2608 of the spyder module 2600. This piece 2610 has a pair of opposed tabs or flanges 2614 (hidden because they are disposed in the channels in FIG. 53) which are received in complementary radial channels 2616 formed in each of the plates 2606 and 2608. Using a polygonal shape, such as to receive an Allen wrench or other key, the piece 2610 is rotated into position to lock the tabs 2614 within the channels 2616. This rotation can be governed by a fixed stop, or can incrementally tighten in a cam style fashion in which to tension the sternal sections.

The spyder module 2600 may be put in place before the sternum is bisected. It is thereby in excellent position for reconnection using the described rotatable piece 2610 when it is time to reconnect the sternum portions.

Referring to FIGS. 54-60, this system uses what can be considered to be drop-in modules 2700 for fixation across the sternum divide. There are four arms 2702 to the module, having fastener apertures 2704 at the end of the arms to receive fasteners. Additional arms could be added in which to provide additional fixation options or stability. Two arms 2702 are on each plate 2706 2708 of the module 2700, on either side of the sternum portions. Referring to FIGS. 55-57, there is a central rotatable piece 2710 which fits within a central well 2712 between the two plates 2706 and 2708 of the spyder module 2700. This piece 2710 has a pair of opposed tabs or flanges 2714 which are received in complementary radial channels 2716 formed in each of the plates 2706 and 2708. Using a polygonal shape, such as to receive an Allen wrench or other key, the piece 2710 is rotated into position to lock the tabs 2714 within the channels 2716. This rotation can be governed by a fixed stop, or can incrementally tighten in a cam style fashion in which to tension the sternal sections.

One surgical technique using the foregoing spyder module 2700 would provide a frangible base, or a base that is readily cut into the foregoing plates 2706 and 2708. Thus, the spyder module 2700 is put in place before the sternum is bisected. It is thereby in excellent position for reconnection using the described rotatable piece 2710 when it is time to reconnect the sternum portions.

Figure 58:
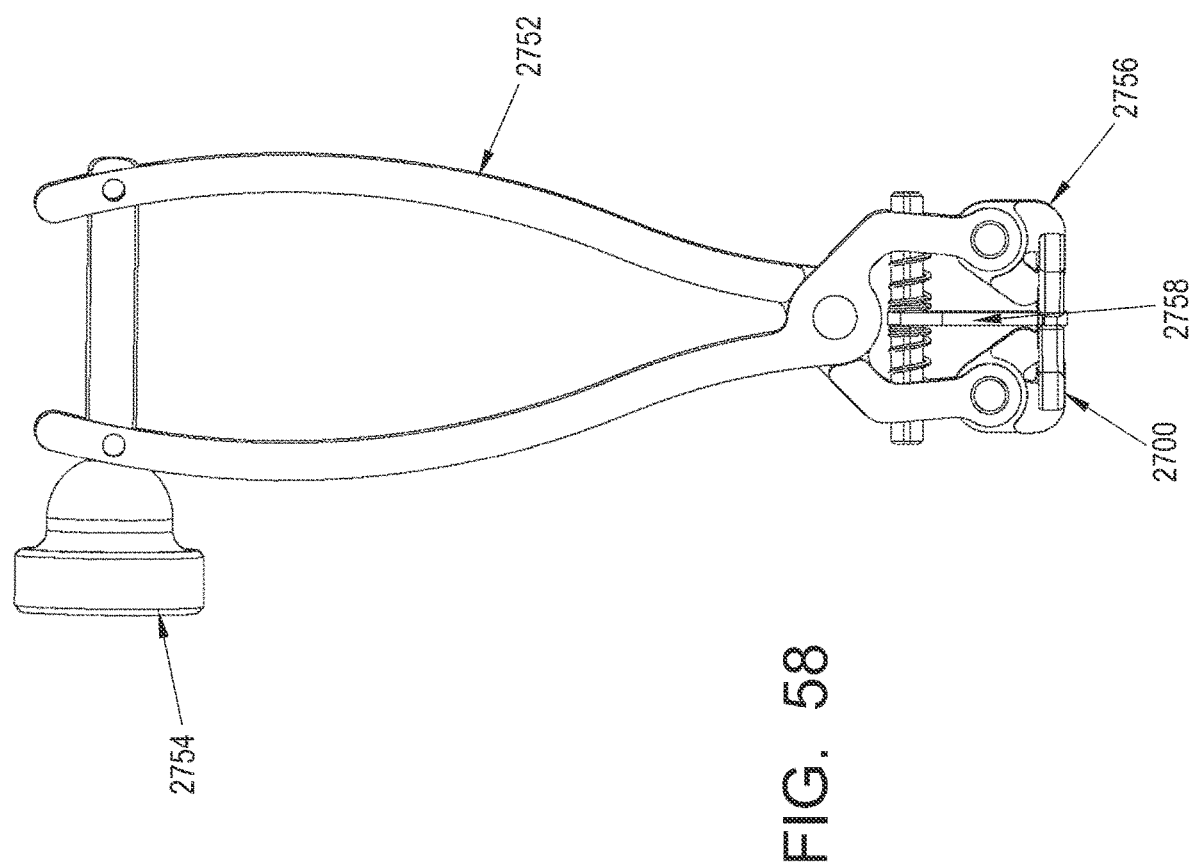
FIG. 58 illustrates a positioner handle for use with a device of the kind shown in FIGS. 54-57 according to the disclosure.
Figure 59:
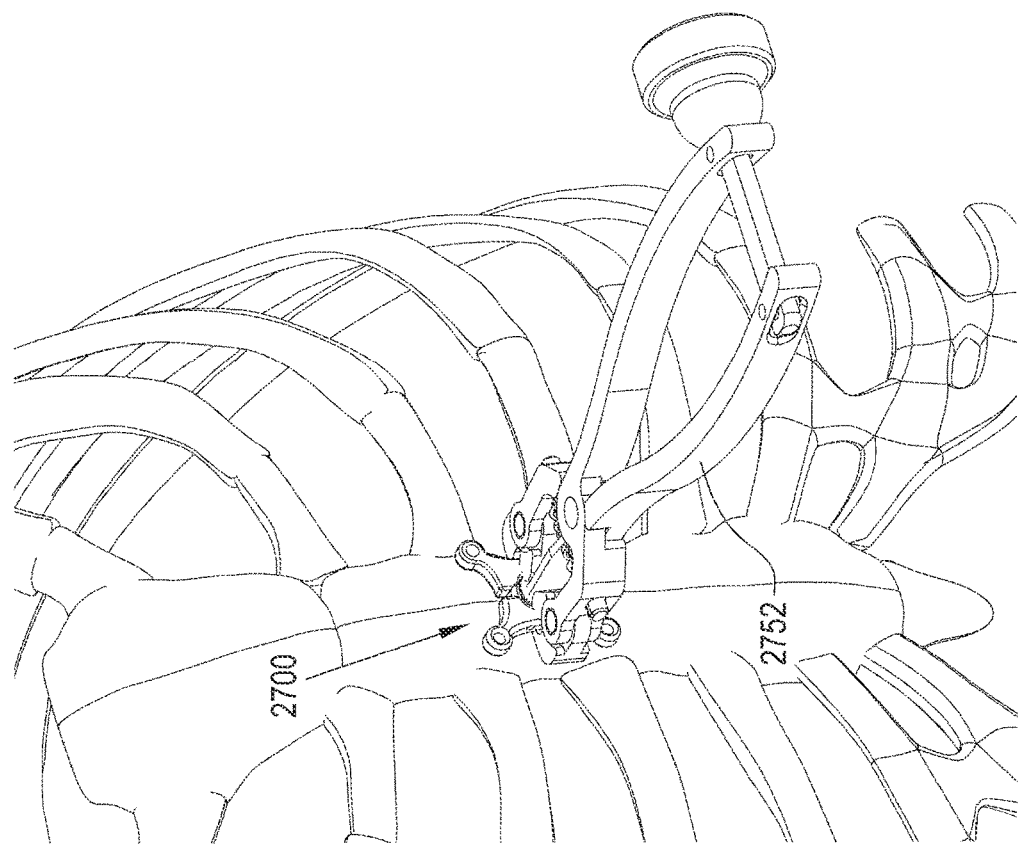
FIG. 59 illustrates devices from FIGS. 54-58 used in tandem according to the disclosure.

FIGS. 58 and 59 illustrate a positioner device in which to position the module 2700 on the sternum. The device has opposing handles 2752 and locking knob 2754. Jaws 2756 mate with the module 2700 and allow the module 2700 to be positioned on the sternum. Spacer 2758 spaces the plates 2706 and 2708 apart at a distance that will allow a sternal sawblade to pass between the plates 2706 and 2708. The dimension of the spacer 2758 that sets the plates 2706 and 2708 apart is determined by the thickness of the sternal sawblade as well as the mechanism utilized to lock the plates 2706 and 2708 together.

Figure 60:
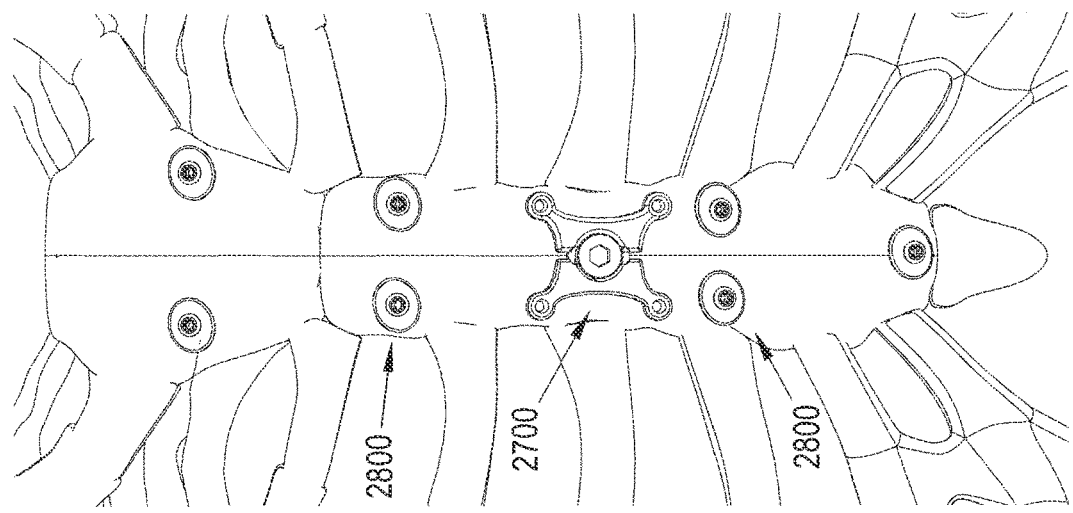
FIG. 60 illustrates a device from FIGS. 54-57 used in tandem with other devices according to the disclosure.

Referring to FIG. 60, a tether element could also be used, applying it using fixation screws 2800 and weaving the tether between spyder modules 2700 along the sternum. In this manner, lateral forces can be accommodated (i.e., managed or controlled) using the tether. Shear forces are accommodated using the solid spyder base module 2700. FIG. 60 illustrates a combination of the spyder lock module 2700 with island screws 2800. More than one spyder module 2700 may be employed. In this embodiment, one can see that shear is accommodated with the spyder module or spyder plate 2700. There is a distribution of tension throughout the arrangement using the island screws 2800. This can be done globally, i.e., by linking all of the anchoring/attachment elements with one or more tethers/cables, or through the use of separate communities of separately tethered anchors/attachments.

Figure 61:
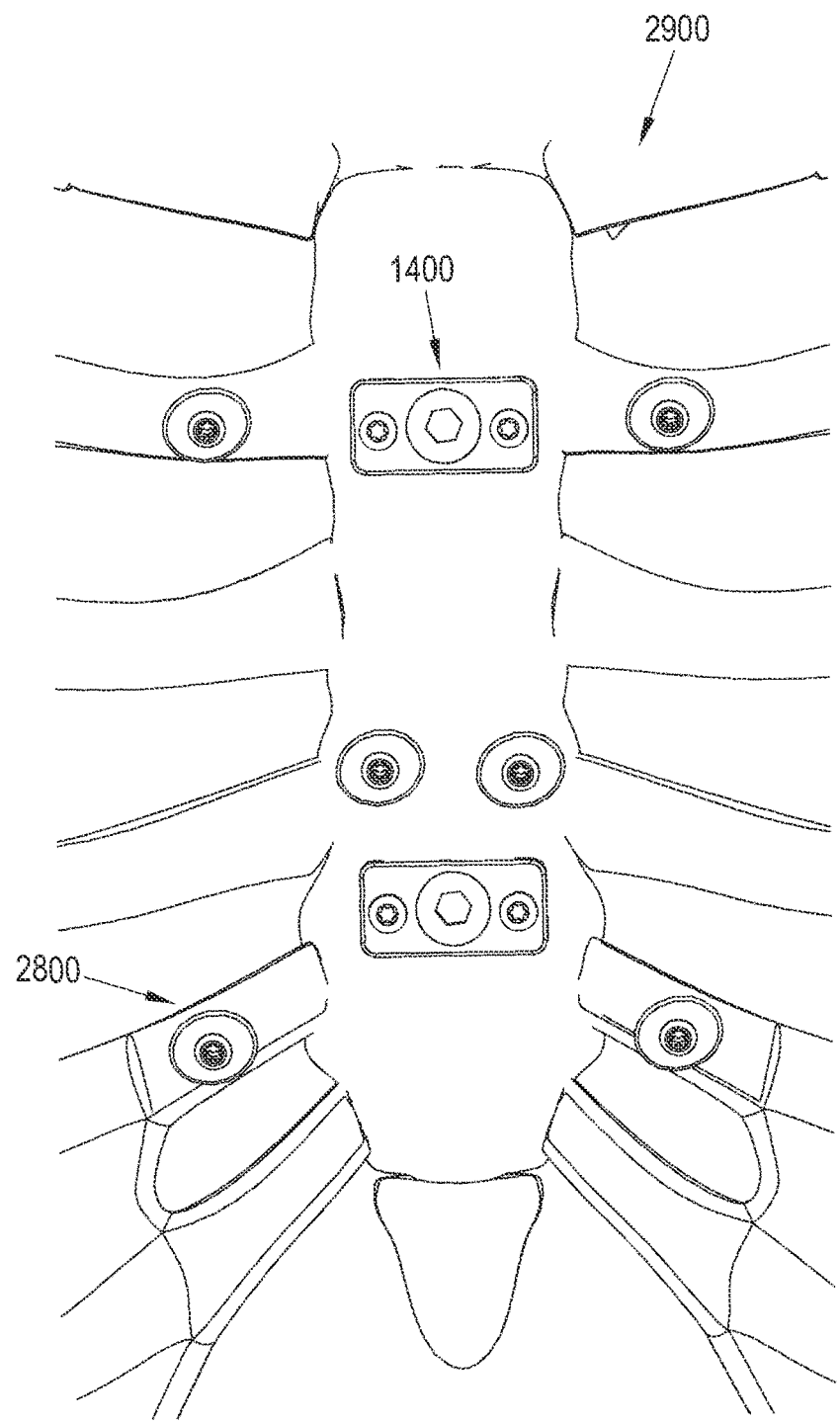
FIG. 61 illustrates another fixation type device used in tandem with other devices according to the disclosure.

FIG. 61 illustrates an interesting combination of the devices 1400 of FIGS. 40 and 41 with island screws 2800 to create a tensioning arrangement 2900. Note how island screws 2800 are located laterally of the sternum itself in some instances, e.g., on the ribs. In one version, the anchors are linked in a desired pattern using a cable or tether. The devices 1400 are then tightened. This can lead to a better distributed tension control.

Figure 62:
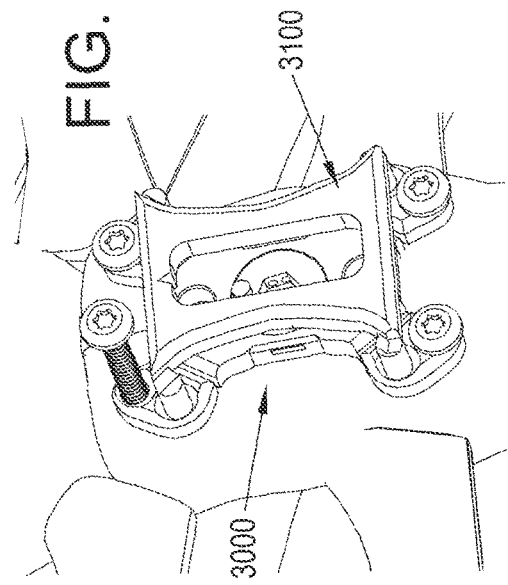
FIG. 62 illustrates another implantable fixation device according to the disclosure.
Figure 63:
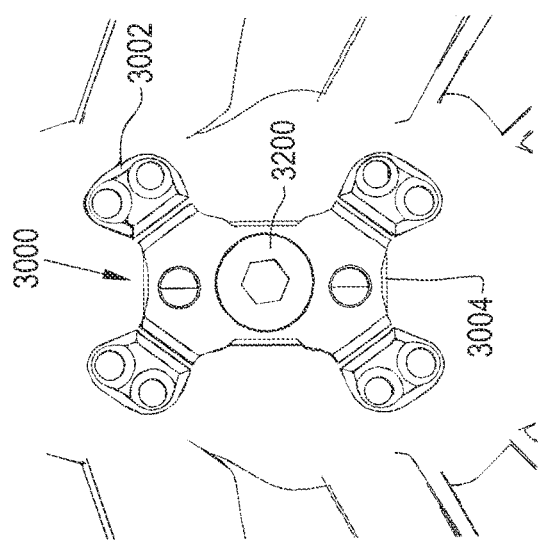
FIG. 63 illustrates a drill guide/placement guide for use with the device of FIG. 62.

FIGS. 62-66 illustrate a system that may be attached to the sternum before resection of the sternum, that is, while the sternum is still intact. Such a system is considered to have significant advantage, in that placement of the fixation elements is accomplished in a manner where alignment post-heart surgery (for example) of the sternum is virtually assured. This embodiment uses spyder-type plate modules 3000 which have separate peripheral arms 3002 and 3300, which fit with a middle tension element 3004. FIG. 62 the module 3000 arranged on a sternum. FIG. 63 illustrates how the module 3000 would be attached using a placement guide 3100 for drill holes. The placement guide 3100 may be provided for screw holes. The module 3000 is then affixed with fasteners. The middle tension element 3004 is then removed, and sternal resection accomplished. After the surgical procedure is complete, the sternal portions are brought back to adjacency, the middle tension element 3004 is reinserted, and the module is tightened as described below.

Figure 66:
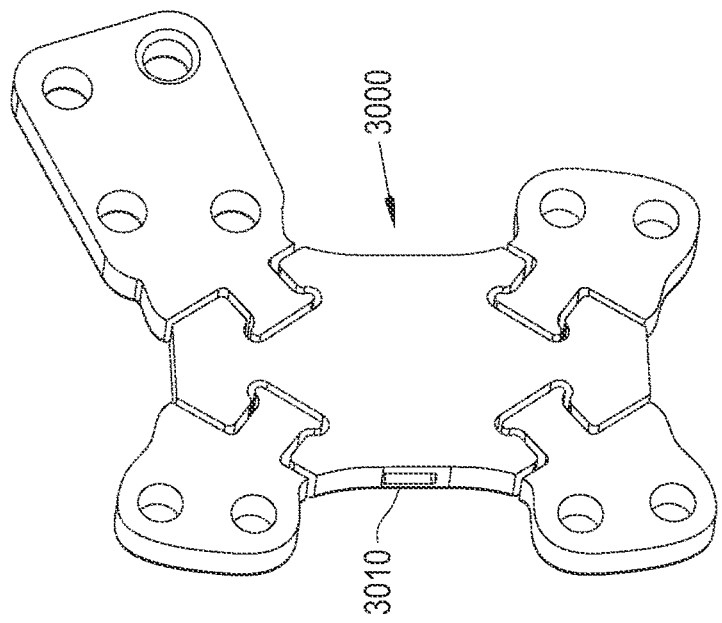
FIGS. 65-66 illustrates a modular type implantable fixation device according to the disclosure.
Figure 65:
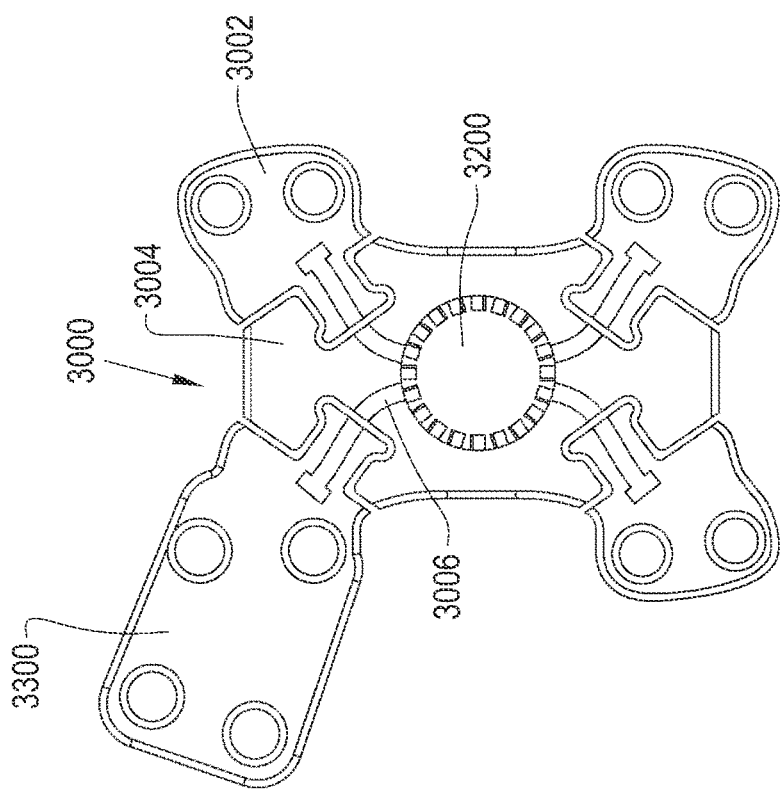

Note that the pieces of this type of module could be made or assembled in different configurations. For example, referring to FIGS. 65 and 66, a puzzle piece type of interconnection is provided for the arms to the middle element. A common type of puzzle interlock is used, for interchangeability. A variety of different shapes for the peripheral arms may be used, such as arms 3002 and/or 3300. Note that this type of module uses a pathway 3006 provided in the module for a nested tether or cable to be tightened via a ratcheting piece 3200. In the event of an emergency reentry to the chest cavity, the cable can be quickly cut with a scalpel inserted into the interface between a peripheral arm and the middle tension element. FIG. 66 illustrates an exit port 3010 from the internal pathways for the tether, for connection with other fixation/anchoring elements (as in a community arrangement).

Figure 64C:
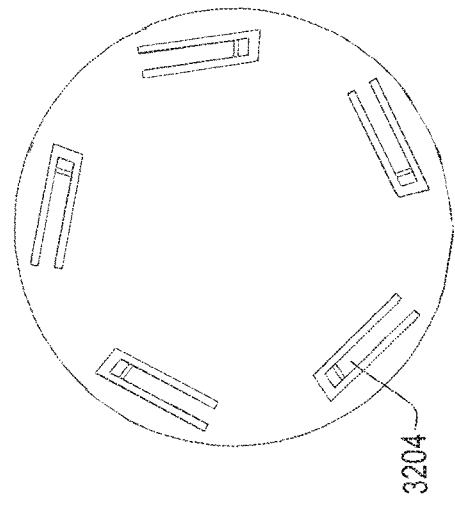
FIGS. 64A-C illustrate a ratchet wheel for use with the device of FIG. 62.
Figure 64B:
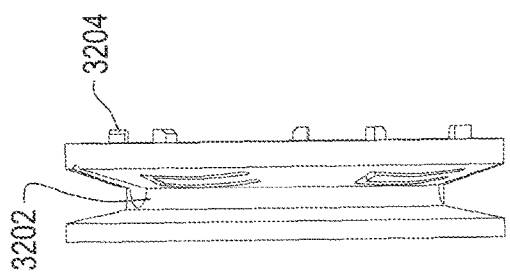
Figure 64A:
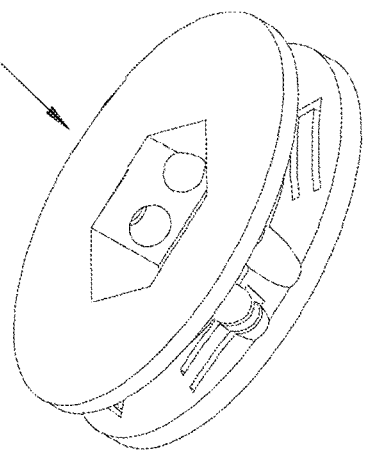

Referring to FIGS. 64A-64C, an example of a type of ratchet piece 3200 which could be employed with the spyder module 3000 of the foregoing embodiment (or other embodiments, for that matter). It is a disk with an annular channel 3202 around the perimeter. Fingers 3204 formed or otherwise provided on the disk engage with detents that would be provided in the well within which the ratchet piece 3202 is received, in a manner to provide one-way rotation of the disk, thereby winding the cable for tightening.

Figure 67:
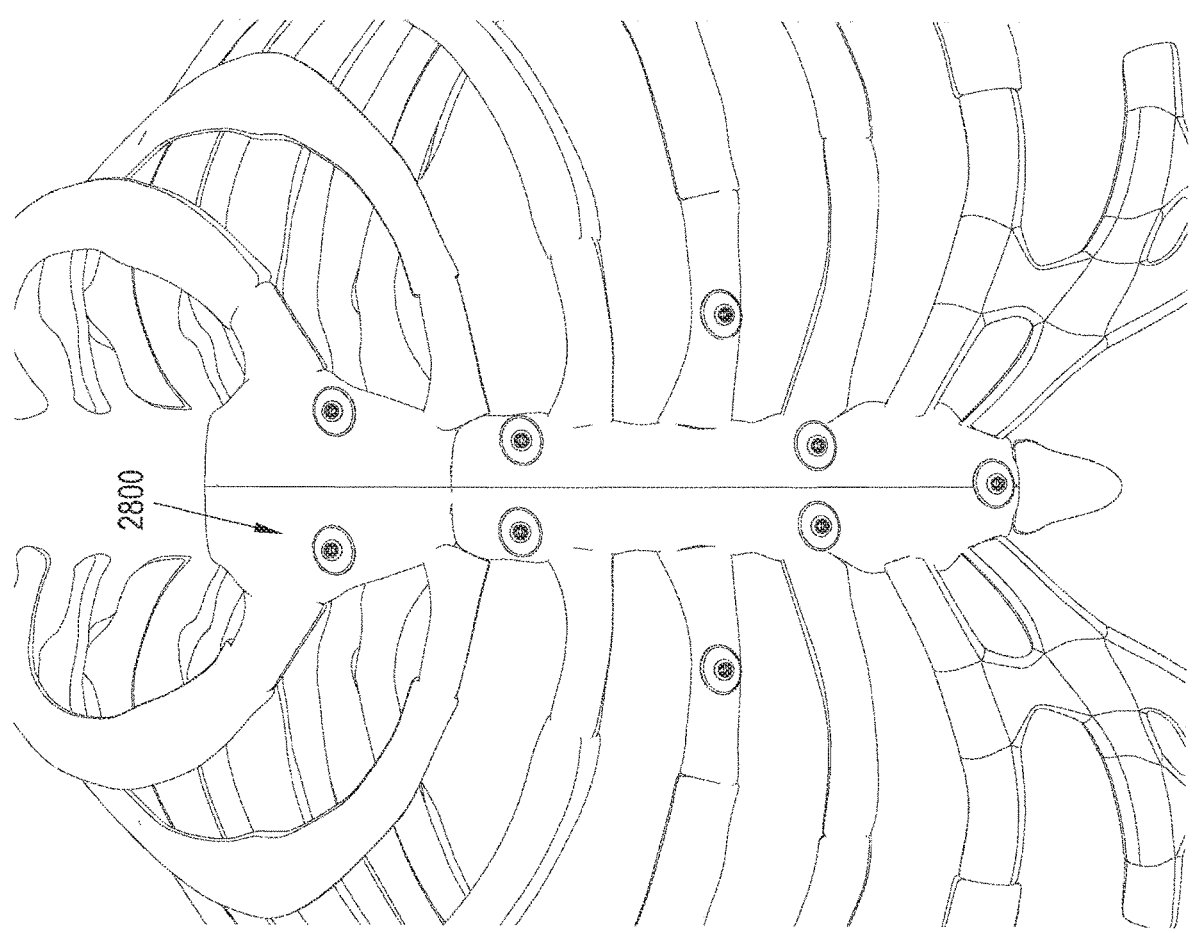
FIG. 67 illustrates an island screw type systems according to the disclosure.

FIG. 67 illustrates a technique that relies upon what are referred to as "island" screws. These singular screws 2800 allow for many placement options. This can include ribs, sternal body, and manubrium. One or more cables/tethers can be wrapped around the island screws 2800 in a variety of configurations. Use of multiple tethers with multiple passes can serve to minimize tension at each node.

In an exemplary surgical technique involving a sternotomy, the surgeon performs an incision. The soft tissue is dissected as appropriate to visualize the bony anatomy. Positions for screws are located, preferably including places of denser bone. Positioning of screws 2800 opposing one another mediolaterally will help to alleviate and diminish shear forces during the tensioning step.

A drill with a drill guide set to about 10 mm depth is used with the self-tapping screws. It is most preferable that the screw spans both cortical walls of the bone. Additionally, the use of non-self-tapping, self-drilling screws may also be advantageous. Preferably, locking screws (straight or polyaxial) that have a unique threadform/locking module in which to lock into the plate as well as the bone to produce a singular construct are utilized.

To close, or realign, the sternum portions, one or more tethers are then wrapped around the island screws 2800 in a desired pattern. A tether should be attached immediately to the direct medial or lateral island screw to avoid undesirable shear. Once reduction is achieved, a lock screw is tightened to secure the tether. The muscle and soft tissue are then closed.

The foregoing procedure can also be alternatively performed with the island screw placement occurring post-sternotomy, that is, after the sternum has been separated.

Figure 69:
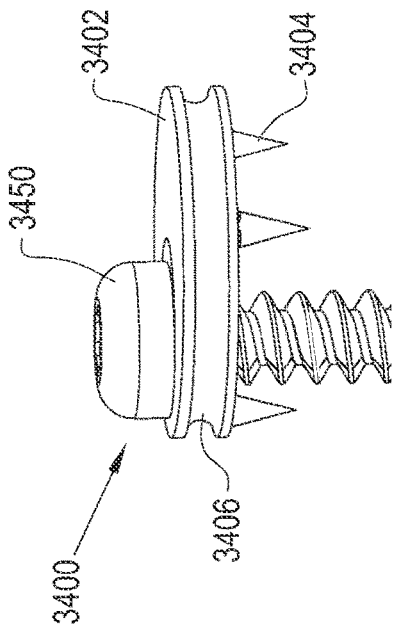
FIGS. 68-70 illustrate a variation on the island screw concept according to the disclosure.
Figure 70:
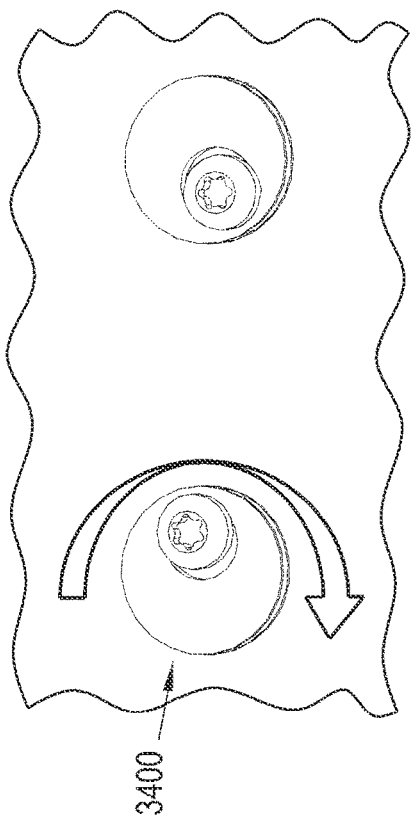
Figure 68:
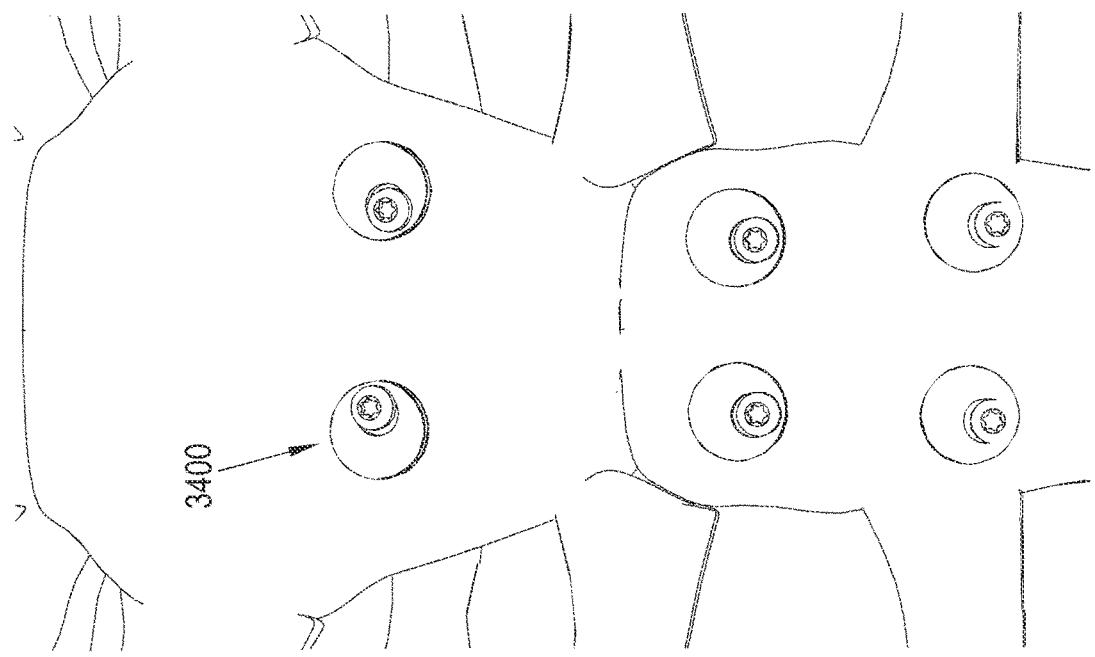

FIGS. 68-70 illustrate another island screw arrangement, but with the addition of one or more cam elements for the screws, yielding a camming anchor 3400. The cam element can be rotated with a spanner, wrench, star driver or other tool to tension the tether. FIG. 69 depicts a type of cam screw element. In general, this camming anchor has a base 3402 with gripping teeth 3404 that drive into the bone surface. There is a cam portion (offset) having an annular channel 3406 which receives a tether. Rotation of the fastener 3450 rotates the integrated cam portion.

Figure 71:
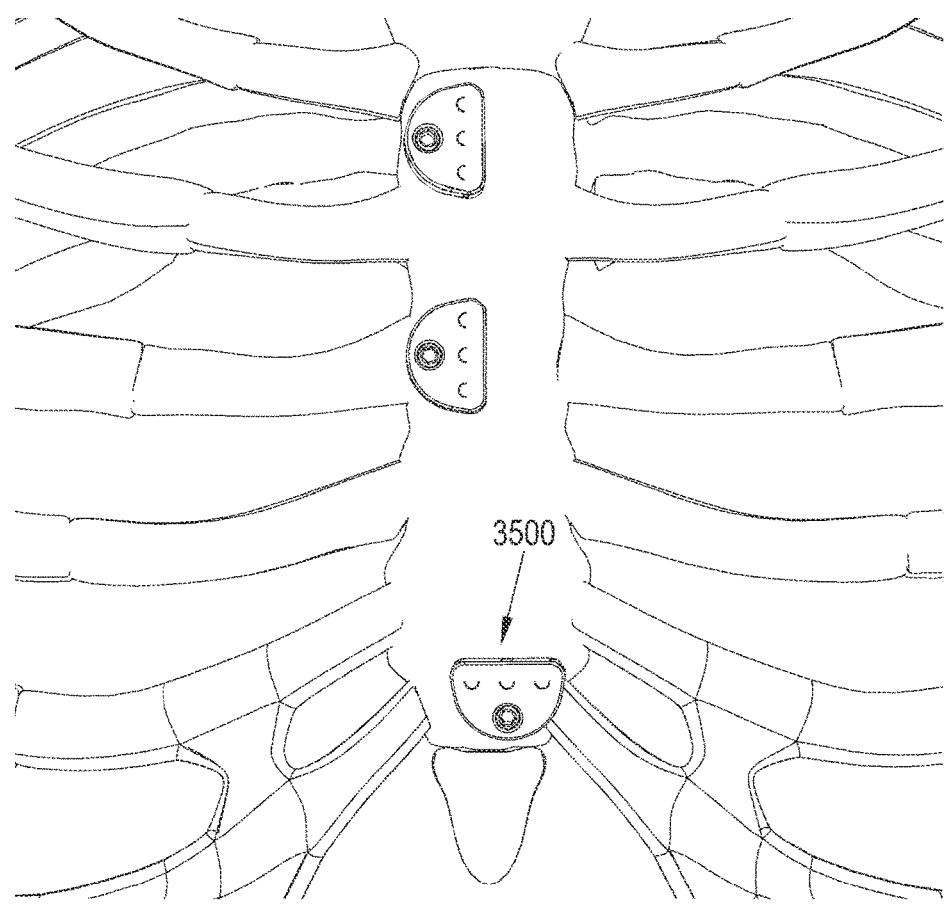
FIGS. 71-73 illustrate another implantable fixation device according to the disclosure.
Figure 72:
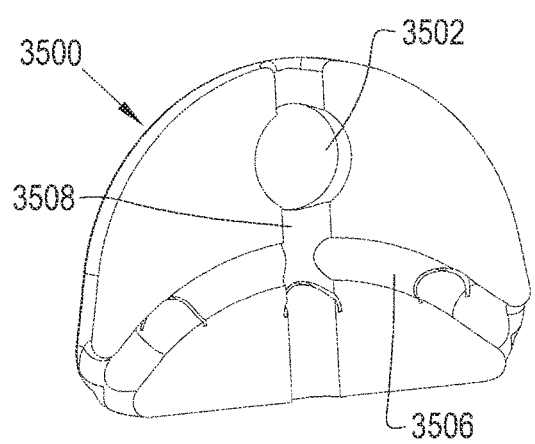
Figure 73:
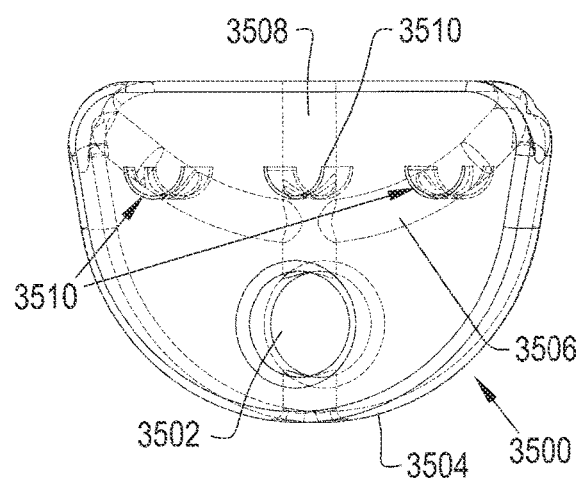

FIGS. 71-73 illustrate a variation using pulley-type fixation elements 3500 associated with one or more base fasteners (not shown). The pulley elements 3500 have a fastener aperture 3502 through which a fastener is received. The pulley element 3500 has a large radius of curvature indicated generally at 3504 over which a tether is received. Inboard of the pulley element 3500 are channels 3506, 3508 in which, or through which, the tether(s) may also be woven. Pulley elements 3500 in this version also have locking tabs 3510. Once the tether is woven through the pulley, the locking tabs 3510 can be bent down to fix the tether in place. The pulleys elements 3500 can be used in aligning force vectors before final rotational positioning is selected. Shear force vectors can likewise be balanced with the pulleys and tether arrangements.

Figure 74:
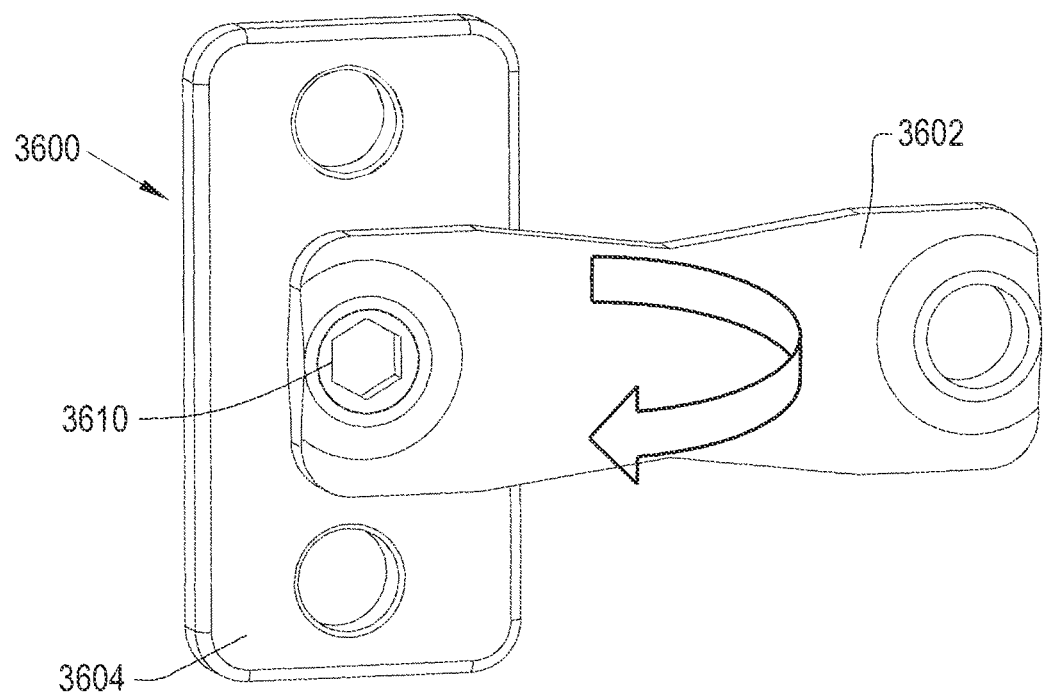
FIGS. 74-75 illustrate another implantable fixation device according to the disclosure.
Figure 75:
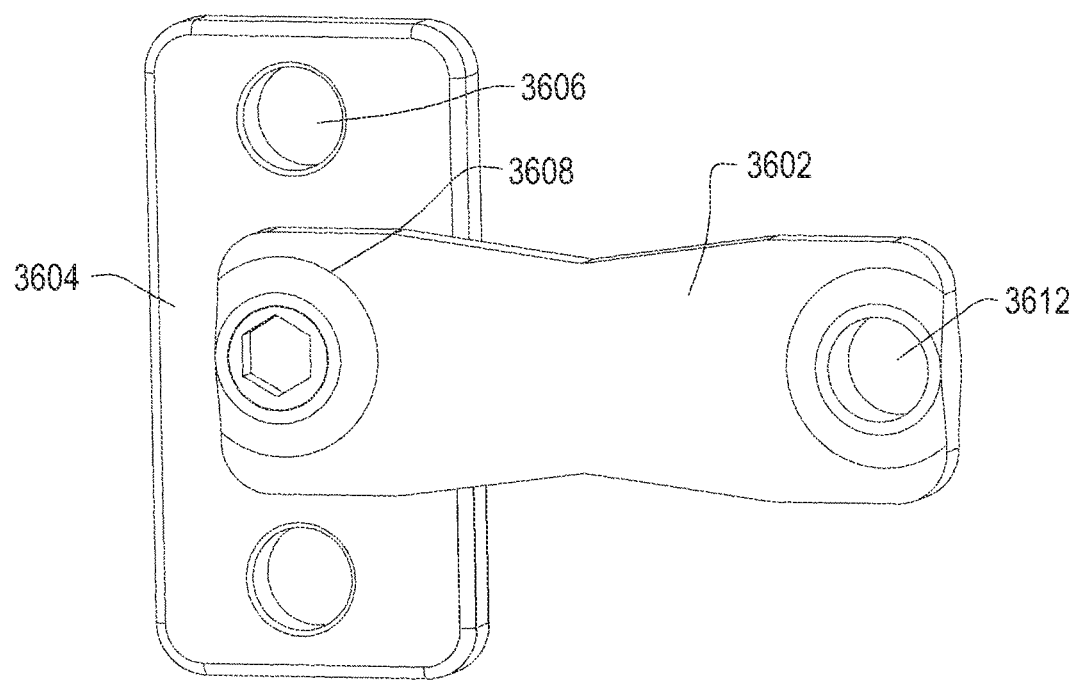

FIGS. 74 and 75 illustrate a plate fixation arrangement 3600 which uses a linking tie element 3602 between discrete plates 3604, each plate 3604 being located on one portion of the sternum along a division line (only one plate is shown), that is, one of each of a pair of plates 3604 is located on either side of the sternotomy division line. Each plate 3604 has fastener apertures 3606 for receiving a bone screw therein. Spanning the opposed plates is the tie element 3602. The tie element 3602 in this embodiment is made of a fabric of commercial surgical grade titanium. Additionally, biocompatible materials such as 316 SST, titanium allows, PEEK, UHMWPE, or other woven fabrics can be utilized. In one form, the tie element is designed so that it may be readily cut, so as to reopen the sternotomy quickly, as in an emergency reentry procedure.

One or both sides of the tie element 3604 is secured in another aperture 3608 formed in the plate 3604, using a cam screw 3610 which extends through an aperture 3612 in the tie element 3602. As illustrated in FIG. 74, this version of the cam screw 3610 has a head which receives an Allen key, which then rotates the cam element to draw the sternum portions together. A plurality of the foregoing plate-and-tie devices would be spaced along the sternum in a similar arrangement as described with the interlocking plates above.

Figure 77:
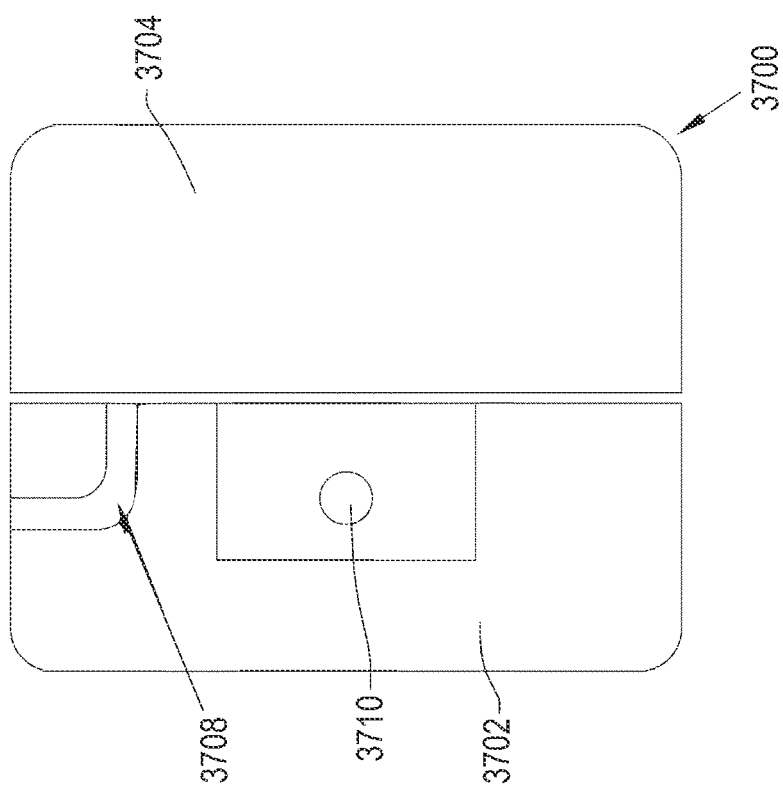
FIGS. 76-77 illustrate another implantable fixation device according to the disclosure.
Figure 76:
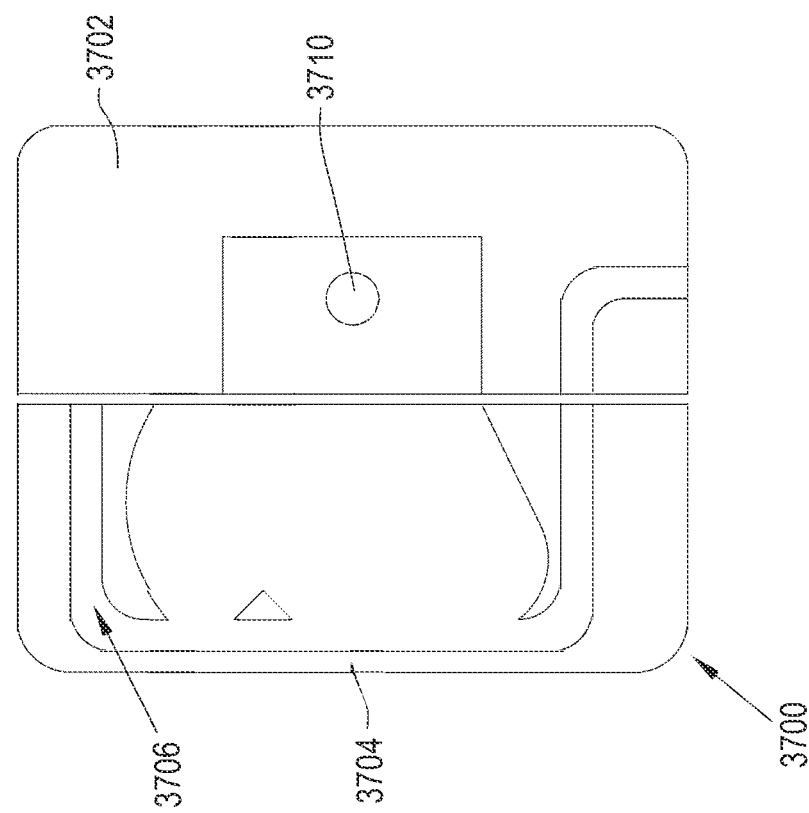

FIG. 76 illustrates a front view and FIG. 77 illustrates a back view of a type of fixation device 3700. The fixation device 3700 has two plates 3702 and 3704 which will be joined to together. As described herein with certain other embodiments herein, this type of fixation device 3700 could be adapted to be put in place pre-resection. That is, the two plates 3702 and 3704 may be anchored, and then the resection performed. Note the pathway provided for resection along the retainer midline.

Provided on the two plates 3702 and 3704 are complementary pathways 3706, 3708 provided inboard or interiorly of the plates 3702 and 3704, within which a tether or cable is received. A variety of pathways may be thereby provided as desired, for different tensioning and force distribution, as well as different exits from the plate for the tether. When tensioned, the tether pulls the plates 3702 and 3704 together. Note that all fastener apertures 3710 that would be typically provided for anchoring the plates 3702 and 3704 are not shown.

Figure 78:
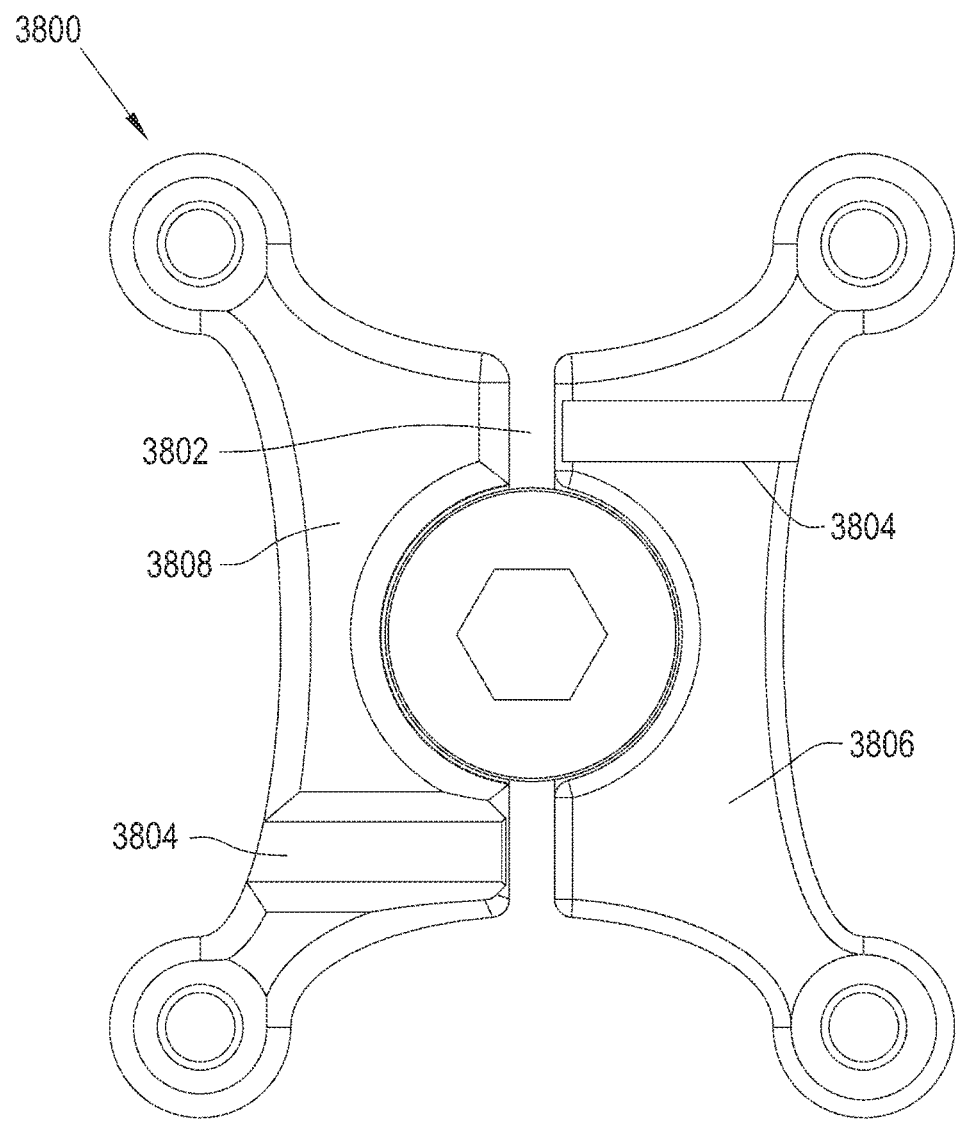
FIG. 78 illustrates another implantable fixation device according to the disclosure.
Figure 81:
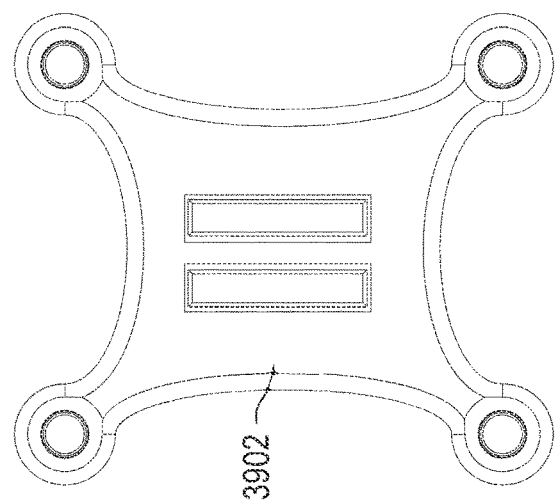
FIG. 81 illustrates an upper part of the device of FIG. 79 according to the disclosure.
Figure 80:
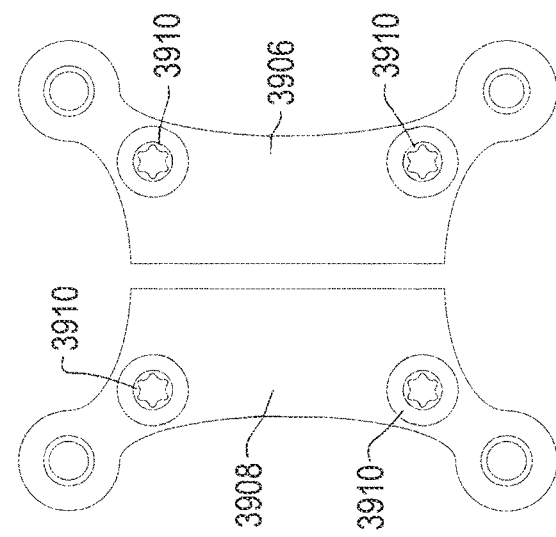
FIG. 80 illustrates the lower part of FIG. 79 with screws therein according to the disclosure.
Figure 79:
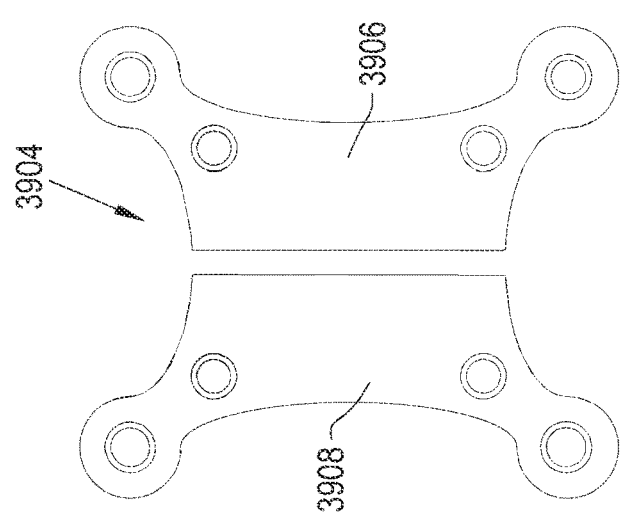
FIG. 79 illustrates a lower part of another implantable fixation device according to the disclosure.

FIG. 78 illustrates a fixation device 3800, which is a variation on the foregoing spider module 3000 described above, that includes an elongate member or pin 3802 that is inserted in a channel 3804 formed in the device 3800 which serves to further stabilize the plates 3806 and 3808.

Figure 82A:
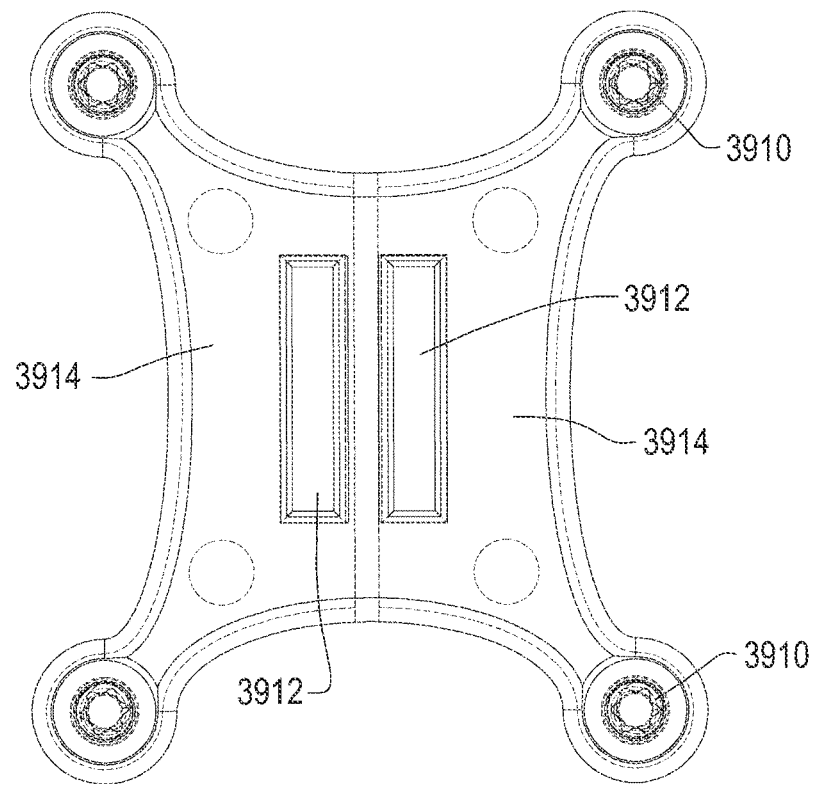
FIGS. 82A-B illustrate another implantable fixation device according to the disclosure.
Figure 82B:
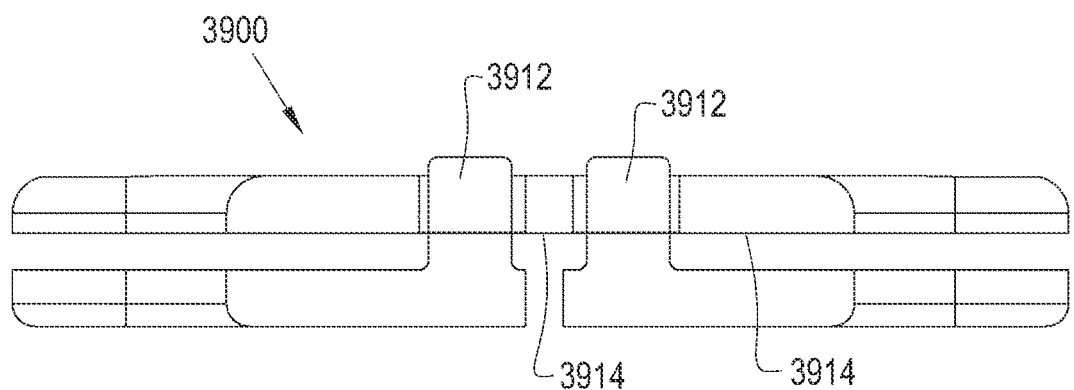

FIGS. 79-82B illustrate another embodiment using a pre-sternotomy affixation system. This version employs upper 3902 and lower 3904 plates for a spyder module 3900. Using a placement guide, the two plates 3906 and 3908 of the lower plate 3904 are located and attached to the sternum before resection using fasteners 3910. The cut through the sternum will pass between the plates 3906 and 3908. After resection and to reattach the sternum portions, the upper plate 3902 is then attached to the lower plate 3904 using fasteners 3910' through the holes of the overlapping plate arms (upper and lower). FIGS. 82A-B illustrate how the lower plate screws are thereby maintained between the plates.

FIGS. 82A-B illustrate how the upper plate 3902 pulls the lower plates 3906 and 3908 together. This is through the use of posts 3912 provided on the lower plates 3906 and 3908 which are received in slots 3914 in the upper plate 3902. The slots 3914 are positioned so as to pull the lower plates 3906 and 3908 together when the top plate 3902 is attached.

Figure 83:
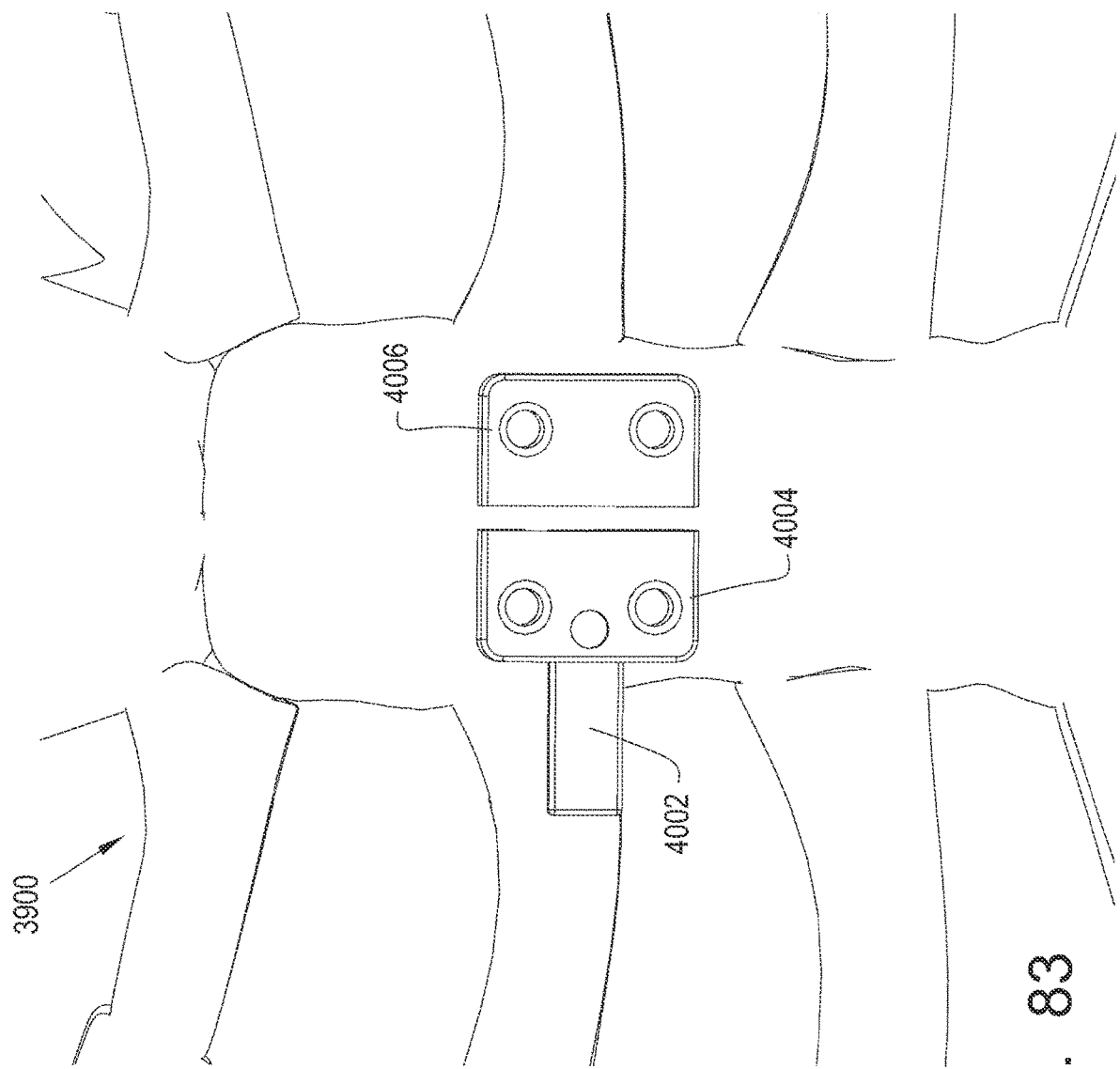
FIG. 83 illustrates another implantable fixation device with a shear tab according to the disclosure.

FIG. 83 illustrates another embodiment 4000 with deployable tab 4002 that is permitted to move along the coronal plane into plate 4004. Deployable tab 4002 is captured inside a second plate 4006. The plates 4004 and 4006, and tab 4002 can be positioned and affixed with screws pre-sternal resection. Tab 4002 can be slid to allow access to the sternal resection plane and sternal resection can be performed. After the heart surgery is completed, tab 4002 can be slid into plate 4004 and locked via a taper lock, mechanical lock, a screw, etc. Plates 4004 and 4006 can be held together in the lateral displacement direction allowing rapid emergency re-entry.

It should be appreciated that the kind of foregoing embodiments that have cooperating pieces spanning the sternum portions can be employed with a variety of integrated pieces. Those embodiments may have one member attached pre-resection, or a member attached on each side of what will be the sternum resection, which are then joined, or rejoined in certain stances, together post-resection.

It should be further understood that the devices and systems described as being applied pre-sternotomy can also be affixed post-sternotomy. Furthermore, the foregoing embodiments have been described with the fixation devices, elements, or anchors, being emplaced anteriorly. It is contemplated that there may be instances where the embodiments may be emplaced posteriorly (from within the chest cavity, for instance, and projecting outwardly from the bone). So too, while it is generally contemplated in the foregoing embodiments that a plate or plate like member is positioned and/or an anchor element is applied to fix the plate in place, the plates and/or anchor elements may be placed in any order. Further, it should be appreciated that the features of one of the embodiments may be incorporated into the other embodiments, and/or the embodiments may be utilized together or in combination.

Figure 84:
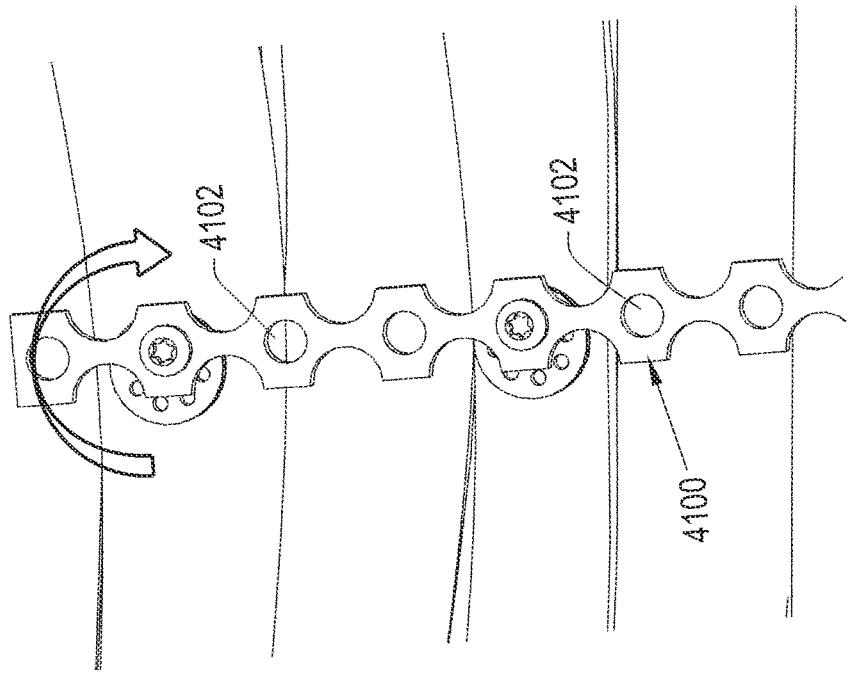
FIG. 84 illustrates another implantable fixation device with a shear tab according to the disclosure.

In situations where there are broken ribs, or a situation where ribs are desired to be otherwise mechanically spaced (illustrated in FIG. 87), FIG. 84 illustrates a strap element 4100 that can be used to brace and space ribs. This embodiment provides a strap 4100 which has a plurality of openings 4102 formed along the strap to receive screws or other anchoring elements, such as any of the one fasteners, etc. described herein. The strap 4100 is designed of material that can be cut to length, for instance, and may be metal (e.g., Ti), or some rigid plastic, just to name two kinds of useful materials. A cam-type anchoring element may further be employed to achieve desired spacing and tensioning.

Figure 85:
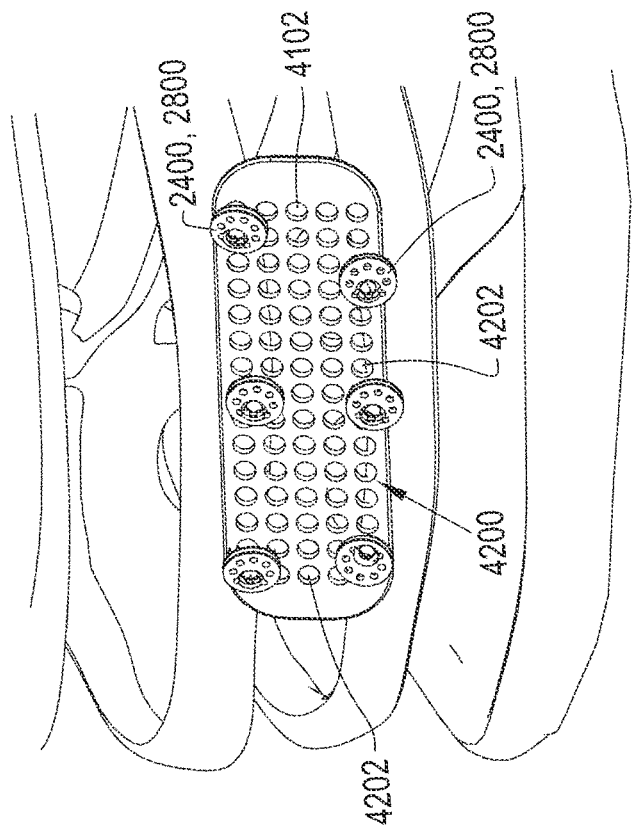
FIG. 85 illustrates another implantable fixation device with a shear tab according to the disclosure.

FIG. 85 illustrates yet another variation on a rib spacing and bracing apparatus. This embodiment has a plate 4200 or strap provided with a plurality of holes 4202. Screws, such as cam-type screw anchors 2400 and/or 2800, or other type of fastener, may be employed. This version thus provides anchoring along a vertical axis between adjacent ribs, but also along the ribs (laterally), yielding further stability.

Figure 86:
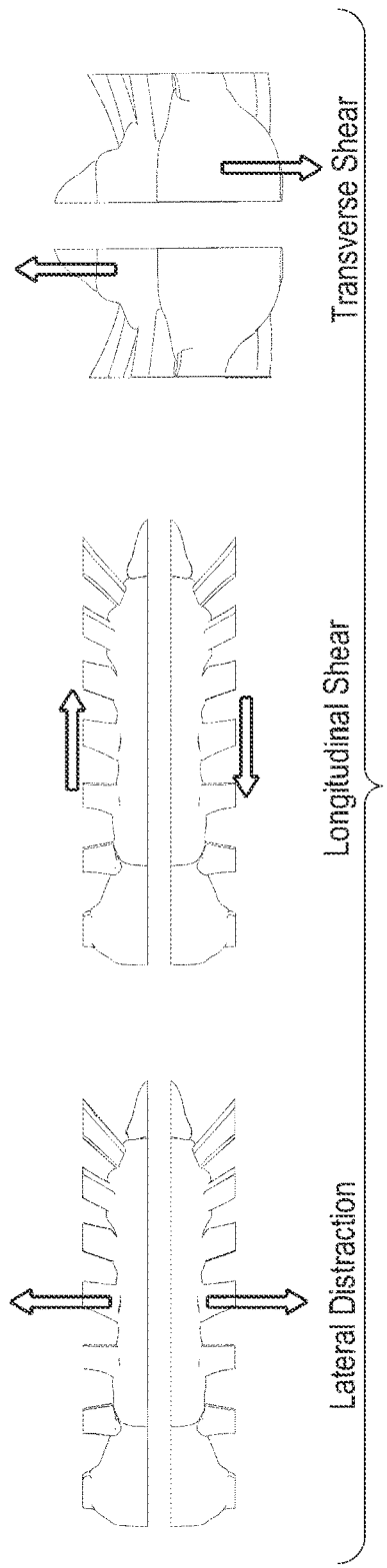
FIG. 86 illustrates, for reference, types of forces discussed herein.
Figure 88:
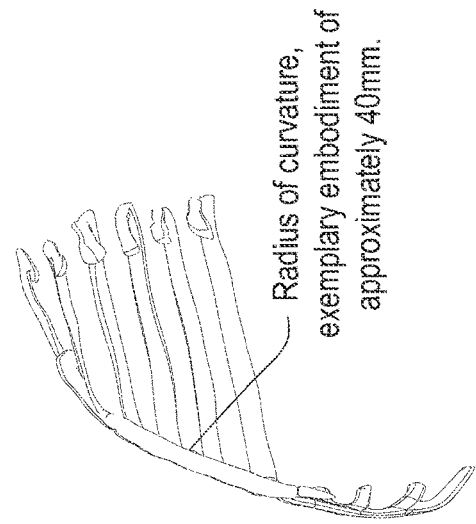
FIG. 88 illustrates a sagittal cross section of a sternum and an approximate radius of curvature.
Figure 87:
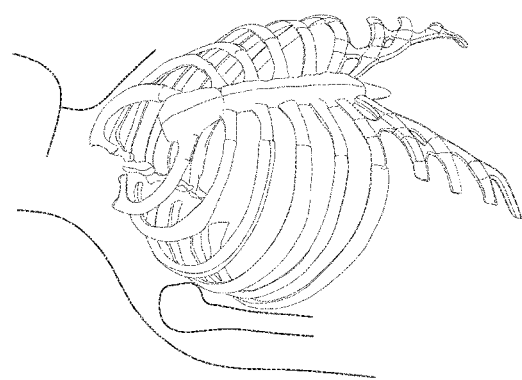
FIG. 87 illustrates a ribcage.

FIGS. 86-88 illustrate various loading terminology as well as anatomical structure useful in considering this disclosure. FIG. 88 illustrates an improvement for anatomic fit of the sternal shear modules to the sternal bone. The radius of curvature generally indicated in this embodiment is a simplification (only discussing a second contour) where some patients will exhibit a tighter (numerically smaller) radius at the cranial portion and some will exhibit a tighter radius at the caudal region. The embodiments described herein can be pre-contoured to fit anatomy either by offering numerous sizes and radii or by preoperatively imaging the patient's anatomy and building the implants from essentially three dimensional imaging.

Although the devices, systems, and methods have been described and illustrated in connection with certain embodiments, many variations and modifications should be evident to those skilled in the art and may be made without departing from the spirit and scope of the disclosure. For example, the components described herein may be made of titanium or other material suitable for surgical procedures. Other materials may also be used depending on the application of use. Similarly, the shapes, sizes, and dimensions of the components may be scaled up or down or altered to suit a particular application. The discourse is thus not to be limited to the precise details of methodology or construction set forth above as such variations and modification are intended to be included within the scope of the disclosure.

What is claimed is:

1. A ratchet fastener, comprising:
a base including a fastening portion including threads and a ratchet portion including teeth that at least partially surround a boss; and
a ratchet wheel including a central aperture that receives the boss to couple the ratchet wheel to the base in mating arrangement with the teeth, the ratchet fastener configured to receive a tether, the ratchet wheel rotatable relative to the ratchet portion of the base for tightening the tether,
wherein the boss includes a protrusion proximal to a top edge of the boss extending radially outward from a center of the boss, wherein the central aperture includes a ledge extending substantially circumferentially around the central aperture and extending radially inward toward a center of the central aperture, wherein a cut-out in the ledge is configured to allow the protrusion to pass through the central aperture when the cut-out and the protrusion are aligned, and wherein the protrusion extends over the ledge when the boss is received in the central aperture and the cut-out and the protrusion are misaligned.

2. The ratchet fastener of claim 1, wherein the boss includes a fastener aperture therein that extends through the boss.

3. The ratchet fastener of claim 2, wherein the fastener aperture of the boss and the central aperture in the ratchet wheel are aligned concentrically when the ratchet wheel is coupled to the base in mating arrangement with the teeth.

4. The ratchet fastener of claim 3, in combination with a bone screw, wherein the bone screw includes a threaded exterior portion, and wherein the fastener aperture of the boss is interiorly threaded for mating with the threaded exterior portion of the bone screw.

5. The ratchet fastener of claim 1, wherein the ratchet wheel includes a pawl configured to engage the teeth and allow the ratchet wheel to rotate in a first direction while preventing rotation in an opposite direction.

6. The ratchet fastener of claim 1, wherein the boss projects from a central portion of a ratchet recess in which the ratchet wheel is received, the teeth positioned along an interior-facing sidewall of the ratchet recess.

7. The ratchet fastener of claim 1, wherein the ratchet wheel includes an open tether slot in an outer surface of the ratchet wheel, the tether receivable in the open tether slot when tightening the tether.

8. The ratchet fastener of claim 1, wherein the base includes an open tether channel in an outer surface of the base, the tether receivable in the open tether channel when tightening the tether.

9. A ratchet fastener, comprising:
a base including a fastening portion including threads and a ratchet recess including teeth,
the ratchet recess including an interior-facing sidewall from which the teeth extend radially inward toward a center of the ratchet recess; and
a ratchet wheel disposed in the ratchet recess in mating arrangement with the teeth, the ratchet fastener configured to receive a tether, the ratchet wheel rotatable relative to the ratchet portion of the base for tightening the tether,
wherein the ratchet recess includes a boss projecting from a central portion of the ratchet recess, the boss receivable in the ratchet wheel when the ratchet wheel is disposed in the ratchet recess in mating arrangement with the teeth,
wherein the boss includes a protrusion proximal to a top edge of the boss extending radially outward from a center of the boss, wherein the central aperture includes a ledge extending substantially circumferentially around the central aperture and extending radially inward toward a center of the central aperture, wherein a cut-out in the ledge is configured to allow the protrusion to pass through the central aperture when the cut-out and the protrusion are aligned, and wherein the protrusion extends over the ledge when the ratchet wheel is disposed in the ratchet recess and the cut-out and the protrusion are misaligned.

10. The ratchet fastener of claim 9, wherein the boss includes a fastener aperture therein that extends through the boss.

11. The ratchet fastener of claim 10, wherein the fastener aperture of the boss and a central aperture in the ratchet wheel are aligned concentrically when the ratchet wheel is disposed in the ratchet recess in mating arrangement with the teeth.

12. The ratchet fastener of claim 11, wherein the fastener aperture of the boss includes a threaded interior portion.

13. The ratchet fastener of claim 12 in combination with a bone screw that includes a threaded exterior portion for mating with the threaded interior portion of the fastener aperture of the boss.

14. The ratchet fastener of claim 9, wherein the ratchet wheel includes a pawl configured to engage the teeth and allow the ratchet wheel to rotate in a first direction while preventing rotation in an opposite direction.

15. The ratchet fastener of claim 9, wherein the ratchet wheel includes an open tether slot in an outer surface of the ratchet wheel, the tether receivable in the open tether slot when tightening the tether.

16. The ratchet fastener of claim 9, wherein the base includes an open tether channel in an outer surface of the base, the tether receivable in the open tether channel when tightening the tether.

* * * * *